United States Patent [19]

Yoshida

[11] Patent Number: 5,194,592
[45] Date of Patent: Mar. 16, 1993

[54] MONOCLONAL ANTIBODIES TO NOVEL POLYPEPTIDE DERIVATIVES OF HUMAN GRANULOCYTE COLONY STIMULATING FACTOR

[75] Inventor: Hajime Yoshida, Kanagawa, Japan

[73] Assignee: Kyowa Hakko Kogyo Co. Ltd., Tokyo, Japan

[21] Appl. No.: 318,527

[22] Filed: Mar. 3, 1989

Related U.S. Application Data

[63] Continuation-in-part of Ser. No. 136,647, Dec. 22, 1987, abandoned.

[30] Foreign Application Priority Data

Dec. 23, 1986 [JP] Japan .................. 61-306799
Mar. 31, 1988 [JP] Japan .................. 63-80088
May 4, 1988 [JP] Japan .................. 63-51357

[51] Int. Cl.⁵ .............................. C07K 15/28
[52] U.S. Cl. ..................... 530/388.23; 530/387.1; 530/387.9; 530/388.1; 530/808; 530/864; 435/70.21; 424/85.8
[58] Field of Search ............... 530/387-388, 530/808, 388.1, 388.23; 424/85.8; 435/70.21

[56] References Cited

U.S. PATENT DOCUMENTS 4,703,008 12/1987 Lin .................. 435/240.2
4,810,643 1/1989 Souza .................. 435/172.3

FOREIGN PATENT DOCUMENTS 0169566 1/1986 European Pat. Off. .
0220520 5/1987 European Pat. Off. .
0225583 6/1987 European Pat. Off. .
0243153 10/1987 European Pat. Off. .
0256843 2/1988 European Pat. Off. .
WO86/04605 8/1986 PCT Int'l Appl. .
WO87/01132 2/1987 PCT Int'l Appl. .

OTHER PUBLICATIONS

Souza et al, *Blood* 66 1985 102(a).
Sevier et al, *Clin Chem* 27/u, 1981, pp. 1797-1806.
Kipps et al., Handbook of Experimental Immunol, ed Weir et al, 1986, pp. 108.1-108.9
*Nature*, vol. 319, Jan. 30, 1986, by S. Nagata, "Molecular Cloning and Expression of cDNA for Human Granulocyte Colony Stimulating Factor" pp. 415-418.
*Science*, vol. 232, No. 4746 Apr. 4, 1986, by Souza et al, "Recombinant Human Granulocyte Colony-Stimulating Factor: Effects on Normal and Leukemic Myeloid Cells", pp. 61-65.

*Primary Examiner*—Garnette D. Draper

[57] ABSTRACT

Novel hG-CSF polypeptide derivatives having an amino acid sequence derived from the amino acid sequence of the human granulocyte colony stimulating factor polypeptide by substitution of at least one amino acid by a different aminoacid and/or deletion of at least one amino acid, recombinant plasmids containing a DNA fragment insert coding for any of these hG-CSF polypeptide derivatives, microorganisms carrying one of such plasmids, and methods of producing the hG-CSF polypeptide derivatives using the microorganisms are described.

1 Claim, 20 Drawing Sheets

```
       27mer   Met Ser  Phe  Leu  Leu  Lys
5'-CGATAAGCT  ATG TCA  TTT  CTT  TTA  AAA   -3'    for
3'-  TATTCGA  TAC AGT  AAA  GAA  AAT  TTT TCGA-5'  pCfTNS 301 or                      29mer
      39mer  Met Ser Leu Pro Gln Ser Phe Leu Leu Lys
5'-CGATAAGCT ATG TCA CTA CCA CAA TCA TTT CTA TTA AAA   -3'    for
3'-  TATTCGA TAC AGT GAT GGT GTT AGT AAA GAT AAT TTTTCGA-5'   pCfTNS401
           41mer
```

MONOCLONAL ANTIBODIES TO NOVEL POLYPEPTIDE DERIVATIVES OF HUMAN GRANULOCYTE COLONY STIMULATING FACTOR

CROSS-REFERENCE TO RELATED APPLICATION

This application is a continuation-in-part of earlier application Ser. No. 07/136,647 filed Dec. 22, 1987, now abandoned.

FIELD OF THE INVENTION

The present invention relates to novel human granulocyte colony stimulating factor (hG-CSF) polypeptide derivatives, recombinant plasmids with a DNA coding for any of said polypeptide derivatives being inserted therein, microorganisms each carrying any of said plasmids, a method of producing said novel hG-CSF polypeptide derivatives a monoclonal antibody binding to said hG-CSF derivative, and chemically modified compounds of said hG-CSF derivatives.

BACKGROUND OF THE INVENTION

The human granulocyte colony stimulating factor (hG-CSF) is a kind of polypeptide which is essential in the formation of various blood cells as a result of proliferation and differentiation of hematopoietic stem cells. Its major effect is to promote the increase in number of granulocytes, in particular neutrophils. Neutrophils play an important part in the protection of the living body from infection.

However, their life spans are short and, therefore, constant supplementation is required by proliferation and differentiation of precursor cells. The therapies widely employed in recent years for proliferative tumors simultaneously inhibit the growth of neutrophil precursors, hence cause a severe side effect, namely a reduction in neutrophilic protection in cancer-bearing patients making them more susceptible to infection. hG-CSF is expected to be effective in alleviating this undesirable side effect through promotion of the increase in the number of neutrophils on one hand and, on the other, in preventing and treating infectious diseases. Furthermore, hG-CSF is active in causing differentiation of leukemic cell lines in vitro and therefore may possibly be useful as a therapeutic agent for leukemia. The hG-CSF polypeptide derivatives according to the invention are superior in hG-CSF activity to the known hG-CSF and are expected to be useful as drugs.

With the recent rapid progress in recombinant DNA technology, genes for proteins involved in the proliferation and differentiation of blood cells have been isolated in succession. Such factors are in production by genetic engineering techniques using microorganisms or animal cells.

A cDNA for hG-CSF was isolated from the human squamous cell carcinoma cell line CHU-II, its base sequence determined and its expression in COS cells reported by Nagata et al. [Nagata et al.: Nature, 319, 415 (1986)]. Souza et al. also isolated a cDNA from the human bladder cancer cell line 5637, determined its base sequence and reported its expression in *Escherichia coli* (*E. coli*) [Souza et al.: Science, 232, 61 (1986)].

The amino acid sequence of the protein encoded by the above two cDNAs is an agreement with the amino acid sequence (Table 1) of the protein encoded by the cDNA isolated from normal human peripheral blood macrophages by the present inventors.

TABLE 1

```
  1        10         20         30         40         50
ACCCCCCTGGGCCCTGCCAGCTCCCTGCCCCAGAGCTTCCTGCTCAAGTGCTTAGAG
Thr Pro Leu Gly Pro Ala Ser Ser Leu Pro Gln Ser Phe Leu Leu Lys Cys Leu Glu
 1

60         70         80         90        100        110
CAAGTGAGGAAGATCCAGGGCGATGGCGCAGCGCTCCAGGAGAAGCTGTGTGCCACC
Gln Val Arg Lys Ile Gln Gly Asp Gly Ala Ala Leu Gln Glu Lys Leu Cys Ala Thr 120        130        140        150        160        170
TACAAGCTGTGCCACCCCGAGGAGCTGGTGCTGCTCGGACACTCTCTGGGCATCCCC
Tyr Lys Leu Cys His Pro Glu Glu Leu Val Leu Leu Gly His Ser Leu Gly Ile Pro 180        190        200        210        220
TGGGCTCCCCTGAGCAGCTGCCCCAGCCAGGCCCTGCAGCTGGCAGGCTGCTTG
Trp Ala Pro Leu Ser Ser Cys Pro Ser Gln Ala Leu Gln Leu Ala Gly Cys Leu 230        240        250        260        270        280
AGCCAACTCCATAGCGGCCTTTTCCTCTACCAGGGGCTCCTGCAGGCCCTGGAAGGG
Ser Gln Leu His Ser Gly Leu Phe Leu Tyr Gln Gly Leu Leu Gln Ala Leu Glu Gly 290        300        310        320        330
ATCTCCCCCGAGTTGGGTCCCACCTTGGACACACTGCAGCTGGACGTCGCCGAC
Ile Ser Pro Glu Leu Gly Pro Thr Leu Asp Thr Leu Gln Leu Asp Val Ala Asp 340        350        360        370        380        390
TTTGCCACCACCATCTGGCAGCAGATGGAAGAACTGGGAATGGCCCCTGCCCTGCAG
Phe Ala Thr Thr Ile Trp Gln Gln Met Glu Glu Leu Gly Met Ala Pro Ala Leu Gln 400        410        420        430        440        450
CCCACCCAGGGTGCCATGCCGGCCTTCGCCTCTGCTTTCCAGCGCCGGGCAGGAGGG
Pro Thr Gln Gly Ala Met Pro Ala Phe Ala Ser Ala Phe Gln Arg Arg Ala Gly Gly 460        470        480        490        500
GTCCTAGTTGCCTCCCATCTGCAGAGCTTCCTGGAGGTGTCGTACCGCGTTCTACGC
Val Leu Val Ala Ser His Leu Gln Ser Phe Leu Glu Val Ser Tyr Arg Val Leu Arg
```

TABLE 1-continued

```
510         520
CACCTTGCCCAGCCCTGA
His Leu Ala Gln Pro ***
                 174
```

SUMMARY OF THE INVENTION

It is an object of the invention to provide a means of producing, at low cost and in large quantities, hG-CSF polypeptide derivatives having high specific activity and high stability in blood.

The present inventors found that hG-CSF polypeptide derivatives having high specific activity can be produced by modifying the cDNA for hG-CSF shown in Table 1 and cultivating a strain of *E. coli* that harbors a plasmid with the modified cDNA inserted therein or by limited polypeptide decomposition using a protease, and they have now completed the present invention.

DETAILED DESCRIPTION OF THE INVENTION

The hG-CSF polypeptide derivatives according to the invention differ in part of the amino acid sequence from the hG-CSF polypeptide having the amino acid sequence shown in Table 1 as a result of substitution and/or deletion. The amino acid or amino acids to be substituted are those amino acids that are located at or in the neighborhood of the N terminus. Preferably, at least one amino acid from among the 1st to 17th amino acids from the N terminus should be the target of substitution. Similarly, the amino acids to be deleted are those amino acids at or in the neighborhood of the N terminus. Preferably, at least one amino acid from among the 1st to 11th amino acids from the N terminus should be deleted.

The recombinant plasmids according to the invention are obtained by inserting a DNA fragment coding for any of the above-mentioned hG-CSF polypeptide derivatives into an appropriate plasmid having a DNA expression function.

Preferred as the DNA fragments coding for the hG-CSF polypeptide derivatives of the invention are those resulting from substitution of at least one base selected from among the 1st to 51st bases of the base sequence shown in Table 1 of the DNA coding for hG-CSF.

Figure 1:
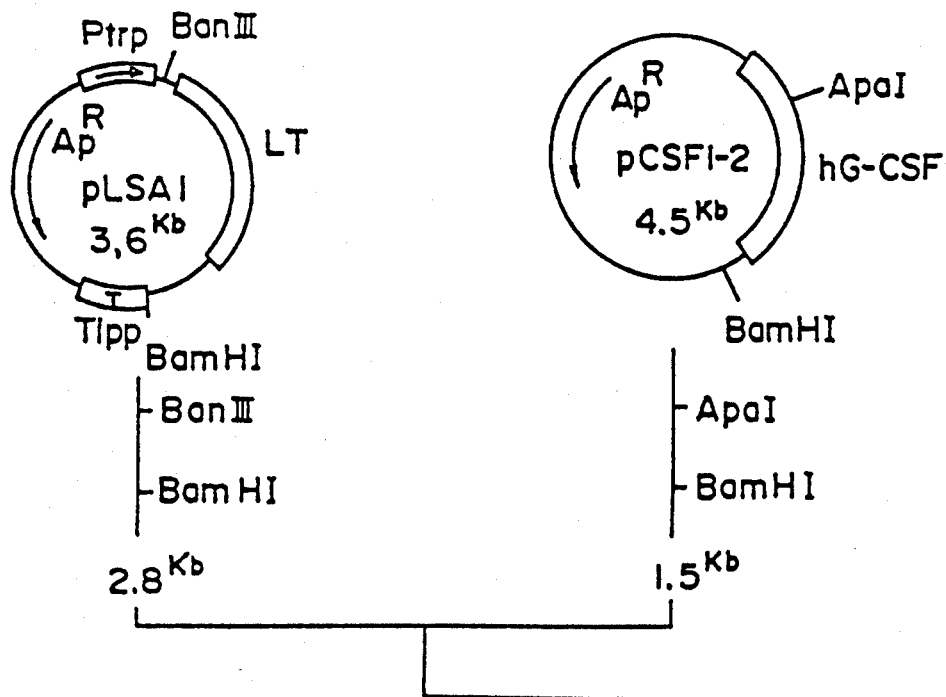
FIG. 1 shows a construction scheme for the plasmid pCfTA1.
Figure 1:
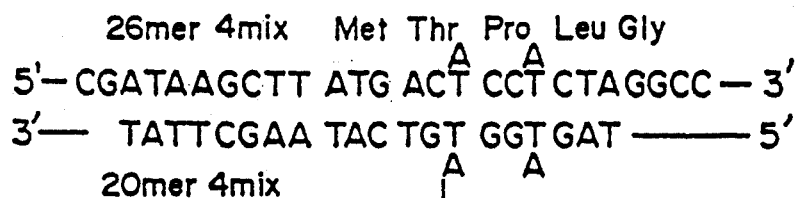
Figure 1:
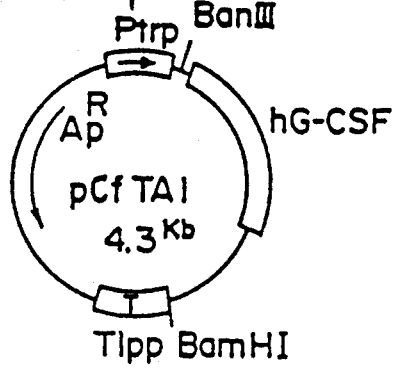

A cDNA (hG-CSF cDNA) obtained by reverse transcription of an hG-CSF-encoding messenger RNA by recombinant DNA technology or an hG-CSF-encoding DNA obtained from chromosomal DNA, for instance, can be used as the hG-CSF-encoding DNA shown in FIG. 1.

Any hG-CSF cDNA may be used provided that it codes for hG-CSF. As an specific example, pCSF1-2, a plasmid produced by the present inventors, can be used. The process for the production of pCSF1-2 is described in Reference Example 1.

The hG-CSF cDNA contained in pCSF1-2 has the base sequence shown in Table 1 as determined by the dideoxy sequencing method using M13 phage [J. Messing et al.: Gene, 19, 269 (1982)].

pCSF1-2 is a plasmid having the restriction enzyme map shown in FIG. 1 and an *E. coli* strain containing it, *E. coli* ECSF 1-2, has been deposited with the Fermentation Research Institute, Agency of Industrial Science and Technology (FRI) since Nov. 27, 1986 under the deposit number FERM BP-1220 in accordance with the Budapest treaty.

Any plasmid may be used for the insertion of an hG-CSF polypeptide derivative-encoding DNA thereinto provided that said DNA can be expressed in *E. coli*.

A plasmid can be used with advantage which allows foreign DNA insertion thereinto at a site downstream from an appropriate promoter, for example, a trp or lac promoter, and has the distance between the Shine-Dalgarono sequence (hereinafter SD sequence) and the initiation codon (ATG) adjusted to an appropriate distance, for example, 6–18 base pairs.

As suitable examples of such plasmid, there may be mentioned pKYP10 (U.S. Pat. No. 4,686,191), pLSA1 (Reference Example 3), pGEL1 Sekine et al.: Proc. Natl. Acad. Sci. USA, 82, 4306 (1985)], pKYP26 [Japanese Patent Application (OPI) No. 48699/87 (the term "OPI" means an unexamined published application)] and pBR322 (Bolivar et al.: Gene, 2, 95 (1977)].

Recombination between a DNA coding for the hG-CSF polypeptide or a derivative thereof and a vector DNA can be effected by recombinant DNA techniques in general use which comprise digesting both DNA with a restriction enzyme or enzymes and the subsequent ligation using T4 DNA ligase. For ligation, the DNA fragment termini resulting from restriction enzyme digestion may be processed, when appropriate, by making use of the filling-in reaction using DNA polymerase I Klenow fragment or the trimming reaction using T4 DNA polymerase; the DNA linker technique is also applicable.

Examples of the construction of recombinant plasmids containing an hG-CSF polypeptide derivative-encoding DNA inserted therein by using pCSF1-2 as the hG-CSF cDNA, pGEL1, pKYP10, pKYP26, pBR322 or pLSA1 as the plasmid for incorporation of the DNA thereinto and, as necessary, a chemically synthesized DNA linker or a technique of site-specific mutagenesis are given in the following.

DETAILED DESCRIPTION OF THE DRAWINGS

Recombination Procedures

As shown in FIG. 1, pCSF1-2 [about 4.5 kilobases (hereinafter kb)] is cleaved with ApaI and BamHI and a DNA fragment of about 1.5 kb is purified by low gelling temperature agarose gel electrophoresis (LGT method) [L. Wieslander: Analytical Biochemistry, 98, 305 (1979)].

Then, pLSA1 is cleaved with BanIII and BamHI, and a DNA fragment of about 2.8 kb is purified by the LGT method. Both the fragments thus obtained and the synthetic DNA shown in FIG. 1 are ligated together using T4 DNA ligase to give pCfTA1.

Figure 2:
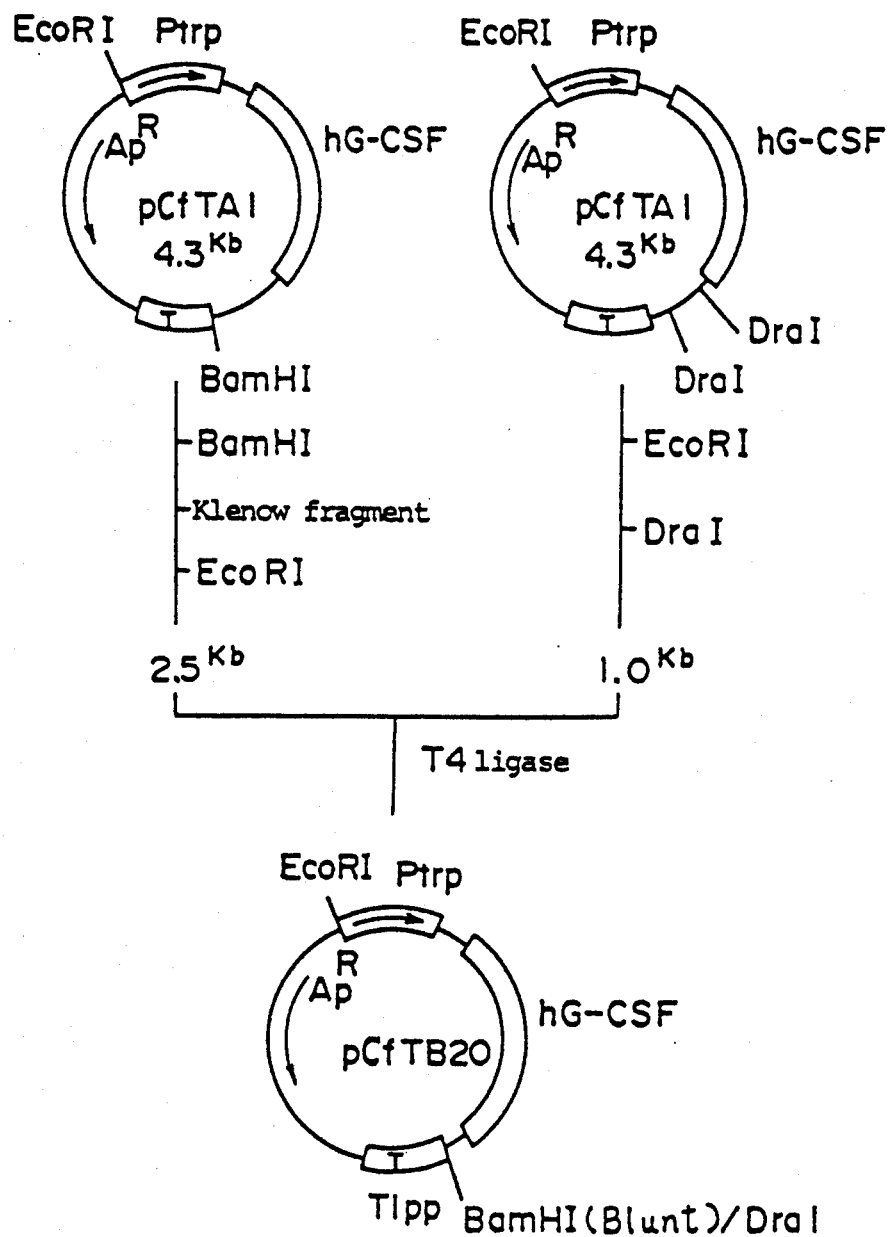
FIG. 2 shows a construction scheme for the plasmid pCfTB20.

Then, as shown in FIG. 2, pCf TA1 is cleaved with BamHI, the protruding ends are converted to blunt ends by treatment with the Klenow fragment and, after further cleavage with EcoRI, a DNA fragment of about 2.5 kb is purified by the LGT method. Separately, pCf TA1 is cleaved with EcoRI and DraI and a DNA fragment of about 1.0 kb is purified by the LGT method. The DNA fragments thus obtained are ligated together using T4 DNA ligase to give pCfTB20.

Figure 3:
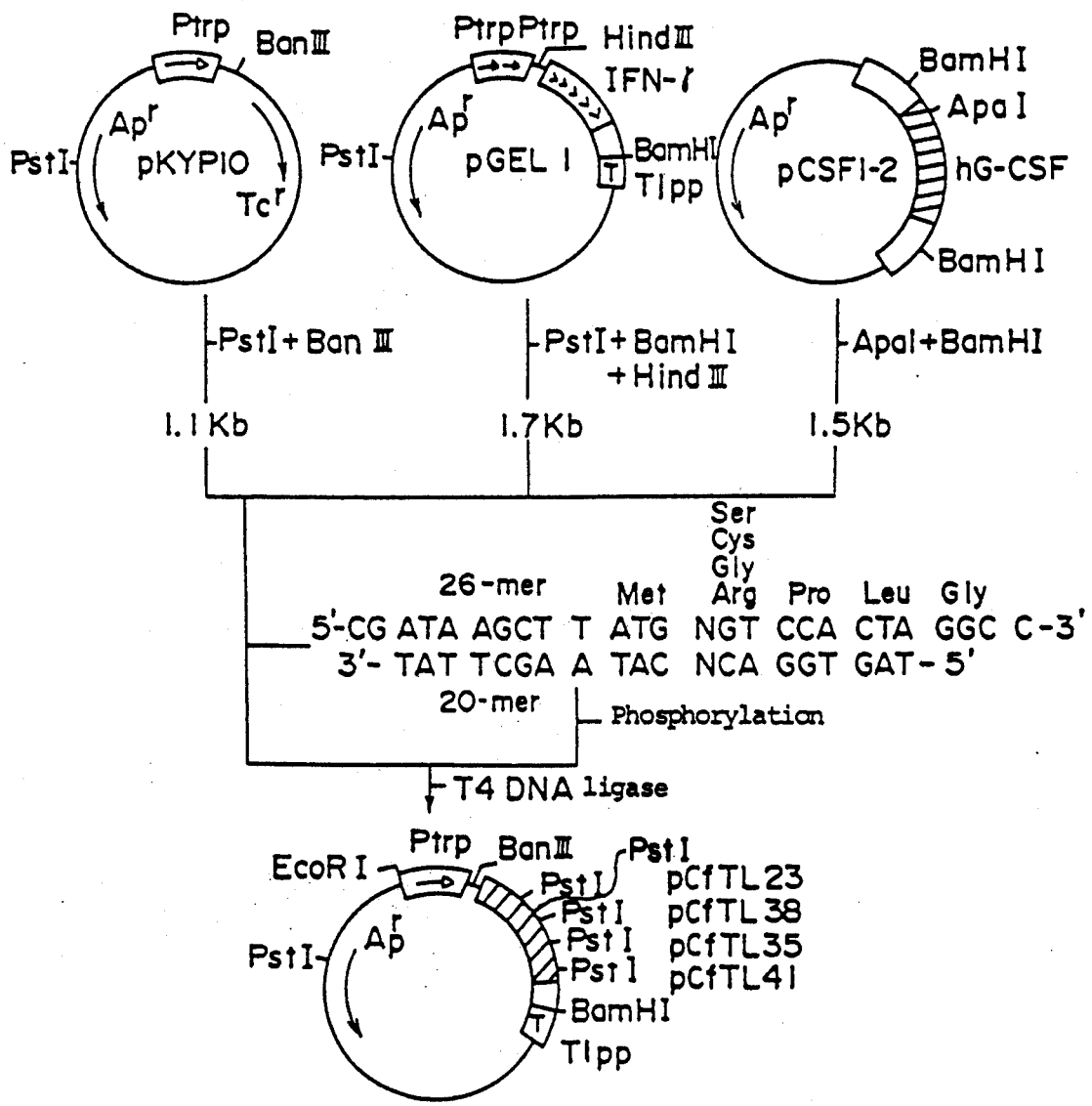
FIG. 3 shows construction schemes for the plasmids pCfTL23, 38, 35 and 41.
Figure 4:
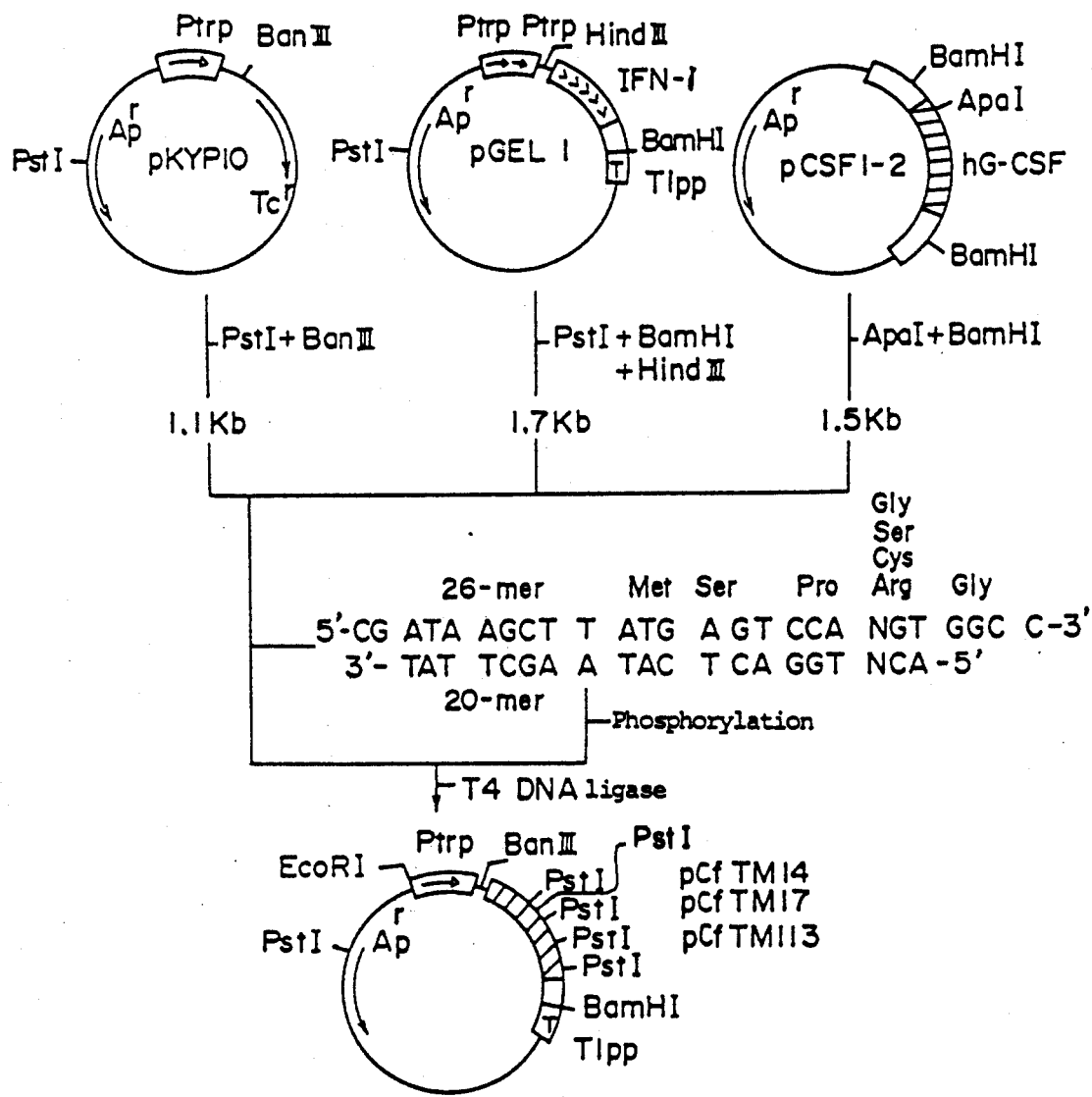
FIG. 4 shows construction schemes for the plasmids pCfTM14, 17 and 113.

Further, as shown in FIG. 3, pCSF1-2 is cleaved with ApaI and BamHI and a DNA fragment of about 1.5 kb is purified by the LGT method. Separately, pGEL1 is cleaved with HindIII, BamHI and PstI and a DNA fragment of about 1.7 kb is purified by the LGT method. Furthermore, pKYP10 is cleaved with PstI and BanIII and a DNA fragment of about 1.1 kb is purified by the LGT method. Ligation of these three DNA fragments and the synthetic DNA shown in FIG. 3 gives pCfTL23, pCfTL38, pCfTL35 and pCfTL41 whereas ligation of these three DNA fragments and the synthetic DNA shown in FIG. 4 gives pCfTM14, pCfTM17 and pCfTM113.

Figure 5:
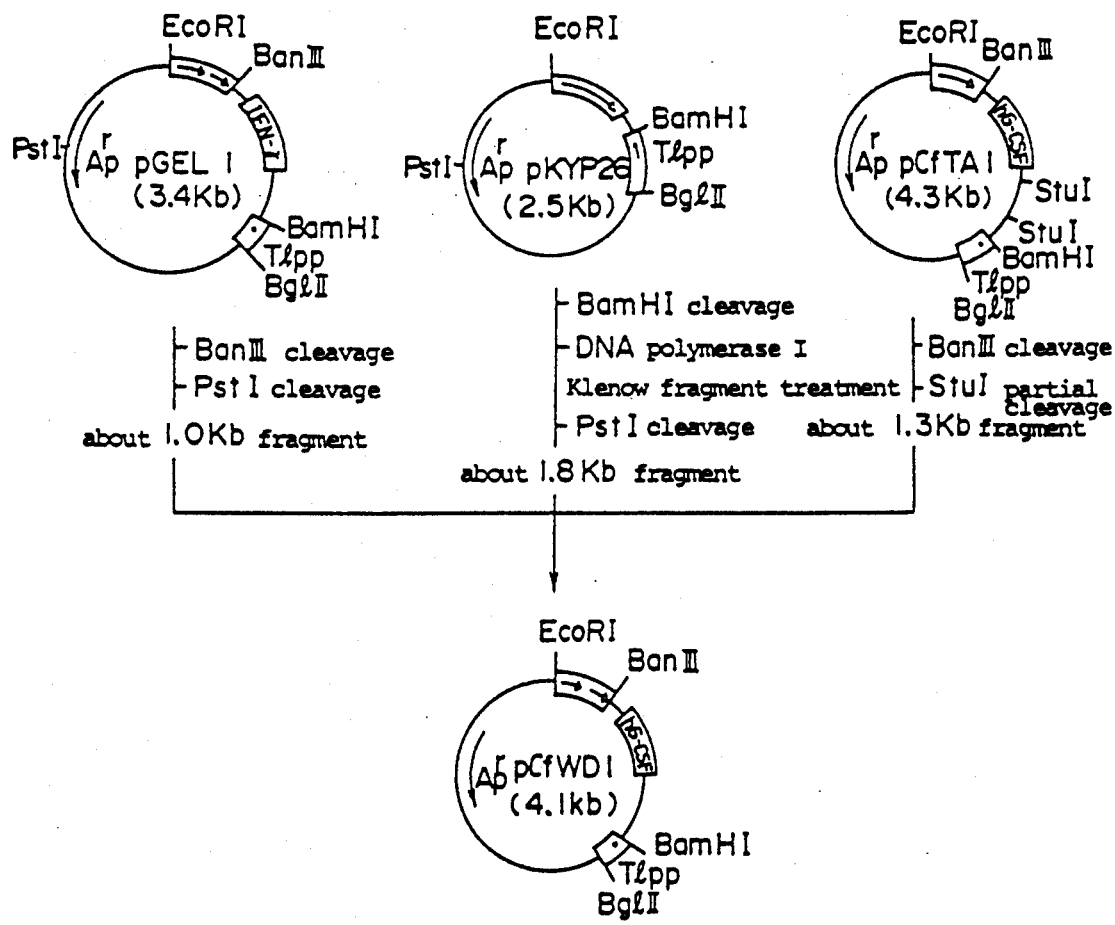
FIG. 5 shows a construction scheme for the plasmid pCfWD1.

Furthermore, as shown in FIG. 5, pCf TA1 is cleaved with BanIII and StuI and an hG-CSF cDNA-containing DNA fragment of about 1.3 kb is purified by the LGT method. Separately, pKY26 is cleaved with BamHI, the protruding ends are converted to blunt ends by treatment with DNA polymerase I Klenow fragment and, after further cleavage with PstI, a DNA of about 1.8 kb is purified by the LGT method. Further, separately, pGEL1 is cleaved with BanIII and PstI and a DNA fragment of about 1.0 kb is purified by the LGT method. The three DNA fragments thus obtained are ligated together using T4 DNA ligase to give pCfWD1.

Figure 6:
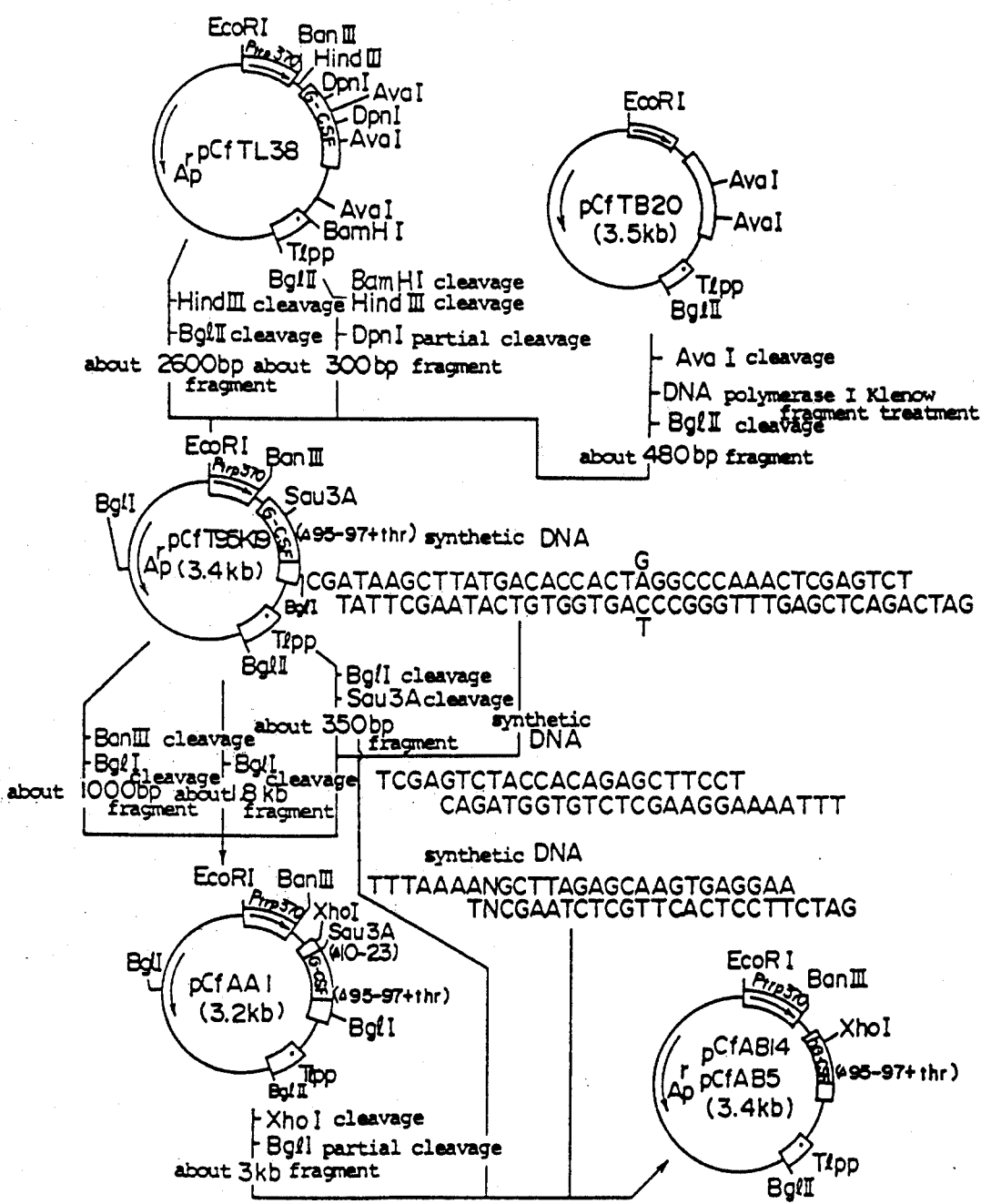
FIG. 6 shows construction schemes for the plasmids pCfT95K19, pCfAA1 and pCfAB5.
Figure 7:
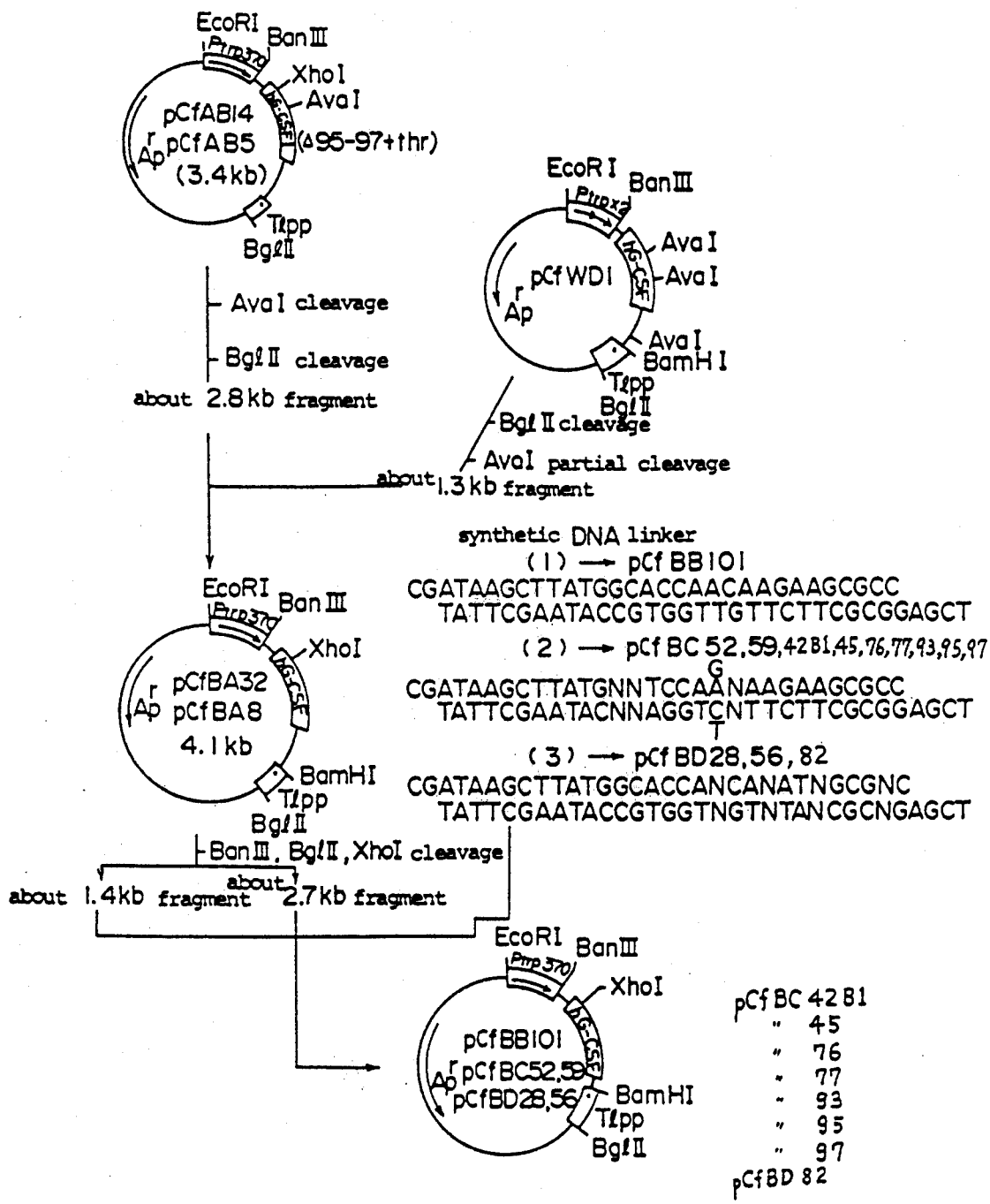
FIG. 7 shows construction schemes for the plasmids pCfBA3, rCfBB101, pCfBC52, 59, 42B1, 45, 76, 77, 93, 95, 97, pCfBD28, 56 and 82.

Further, as shown in FIG. 6, pCfTL38 is cleaved with HindIII and BqlII and a DNA fragment of about 2.6 kb is purified by the LGT method. Separately, pCfTL38 is cleaved with HindIII, BamHI and DpnI and a DNA fragment of about 300 bp (base pairs) is purified by the LGT method. Further, separately, pCfTB20 is cleaved with AvaI, the protruding ends are pared off by treatment with the Klenow fragment and, after further cleavage with BqlII, a DNA fragment of about 480 bp is purified by the LGT method. The three DNA fragments thus obtained are ligated together using T4 DNA ligase to give pCfT95K19. Further, as also shown in FIG. 6, pCfT95K19 is cleaved with BanIII and BglI and a DNA of about 1.0 kb is purified by the LGT method and, separately, pCfT95K19 is cleaved with BqlI alone and a DNA fragment of about 1.8 kb is purified by said method. Further, separately, pCfT95K19 is cleaved with BqlI and Sau3A and a DNA fragment of about 350 bp is purified by the LGT method. The three DNA fragments thus obtained and the synthetic DNA shown in FIG. 6 in the middle thereof (i.e. halfway down) are ligated together to give pCfAA1. Then, as also shown in FIG. 6, pCfAA1 is cleaved with XhoI and BqlI and a DNA fragment of about 3.0 kb is purified by the LGT method. This fragment, the above-mentioned BqlI-Sau 3A fragment (about 350 bp) of pCfT95K19 and the synthetic DNA shown in FIG. 6 at the bottom thereof are ligated together using T4 DNA ligase to give pCfAB5 and pCfAB14. Further, as shown in FIG. 7, pCfAB5 is cleaved with AvaI and BqlII and a DNA fragment of about 2.8 kb is purified by the LGT method. Separately, pCfWD1 is cleaved with BglII and AvaI and the DNA of about 1.3 kb is purified by the LGT method. The two fragments thus obtained are ligated together using T4 DNA ligase to give pCfBA8. On the other hand, pCfAB14 is cleaved with AvaI and BqlII and a DNA fragment of about 2.8 kb is purified by the LGT method, and this fragment is ligated with the above-mentioned 1.3 kb DNA fragment derived from pCfWD1 by cleavage with BqlII and AvaI using T4 DNA ligase, to give pCfBA32. Further, as also shown in FIG. 7, pCfBA8 is cleaved with BanIII, BqlII and XhoI and a DNA fragment of about 1.4 kb and a DNA fragment of about 2.7 kb are purified by the LGT method. Ligation of the two DNA fragments thus obtained and the synthetic DNA linker shown in FIG. 7 using T4 DNA ligase gives pCfBB101, pCfBC52, pCfBC59, pCfBD28, pCfBD56, pCfBC42B1, pCfBC45, pCfBC76, pCfBC77, pCfBC93, pCfBC95, pCfBC97 and pCfBD82.

Figure 8:
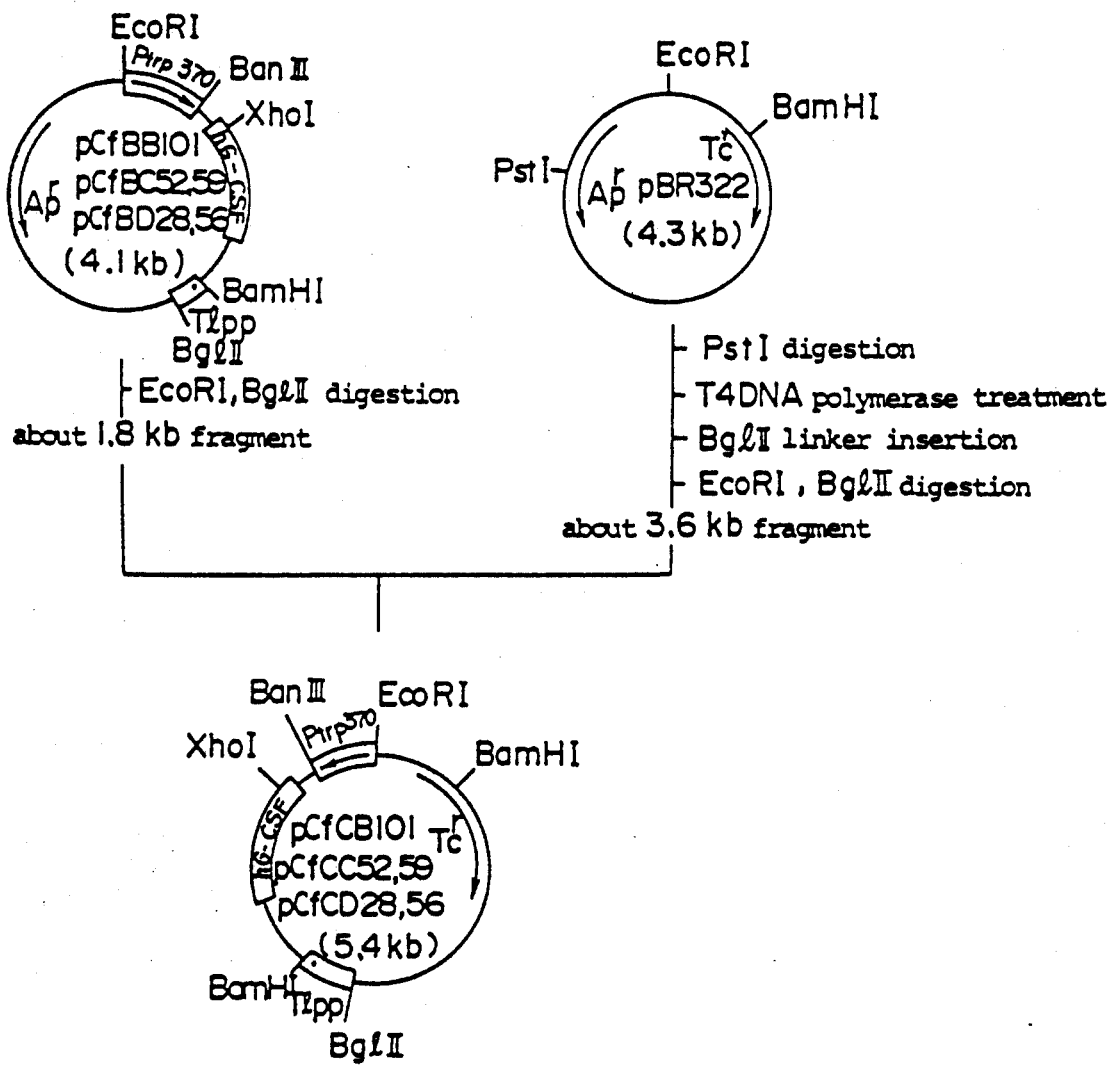
FIG. 8 shows construction schemes for the plasmids pCfCB101, pCfCC52, 59, pCFCD28 and 56.

As shown in FIG. 8, pBR322 is cleaved with PstI, the protruding ends are pared off with T4 DNA polymerase, the BglII linker is inserted using T4 DNA ligase and, after further cleavage with EcoRI and BqlII, a DNA fragment of about 3.6 kb is purified by the LGT method.

The plasmids pCfBB101, pCfBC52, pCfBC59, pCfBD28 and pCfBD56 obtained in the above manner are each cleaved with EcoRI and BqlII and a DNA fragment of about 1.8 kb is purified by the LGT method. Each 1.8 kb DNA fragment is ligated with the pBR322-derived 3.6 kb DNA fragment using T4 DNA ligase. There are thus obtained pCfCB101, pCfCC52, pCfCC59, pCfCD28 and pCfCD56 corresponding to the respective plasmids mentioned above.

Figure 12:
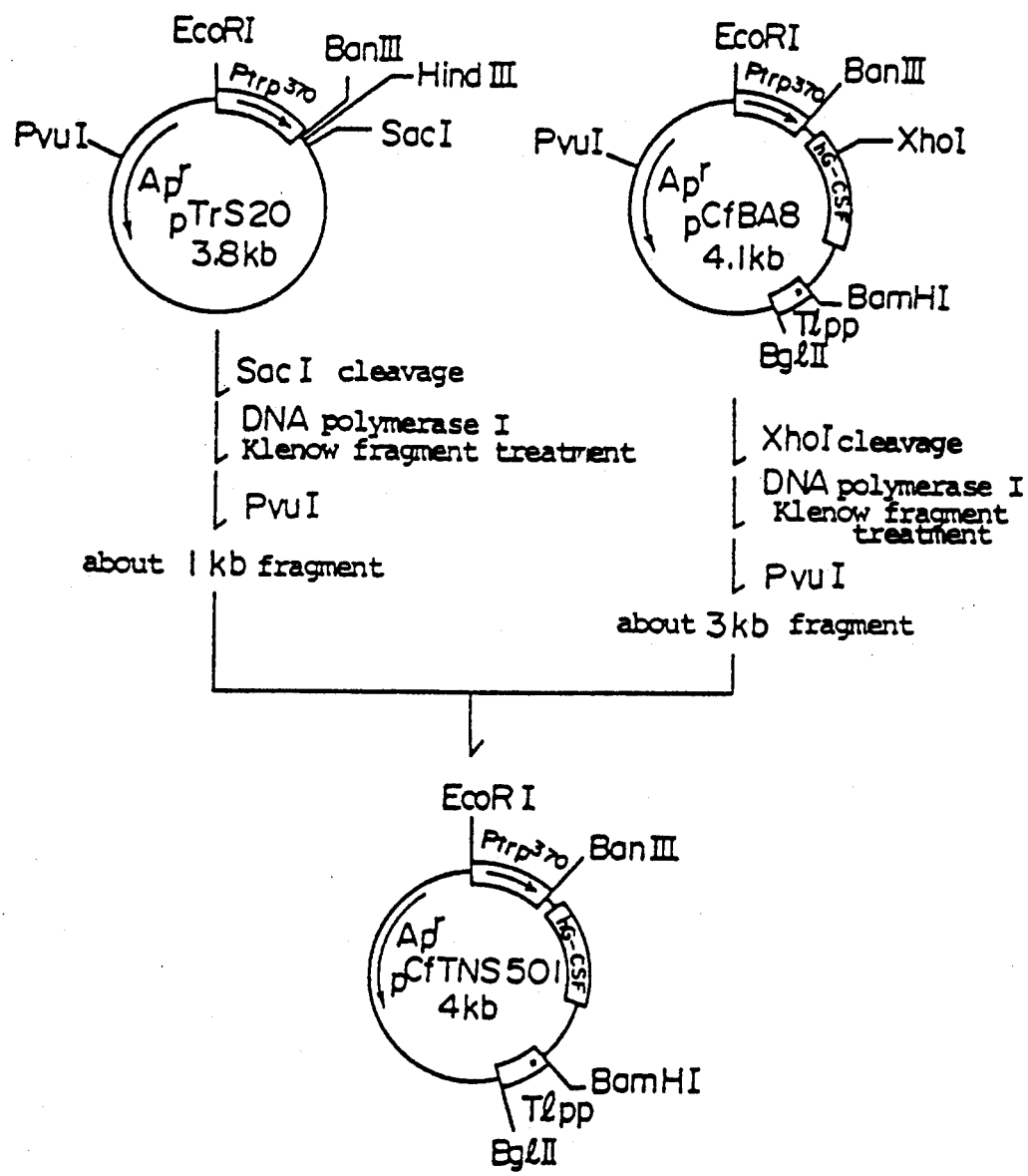
Figure 14:
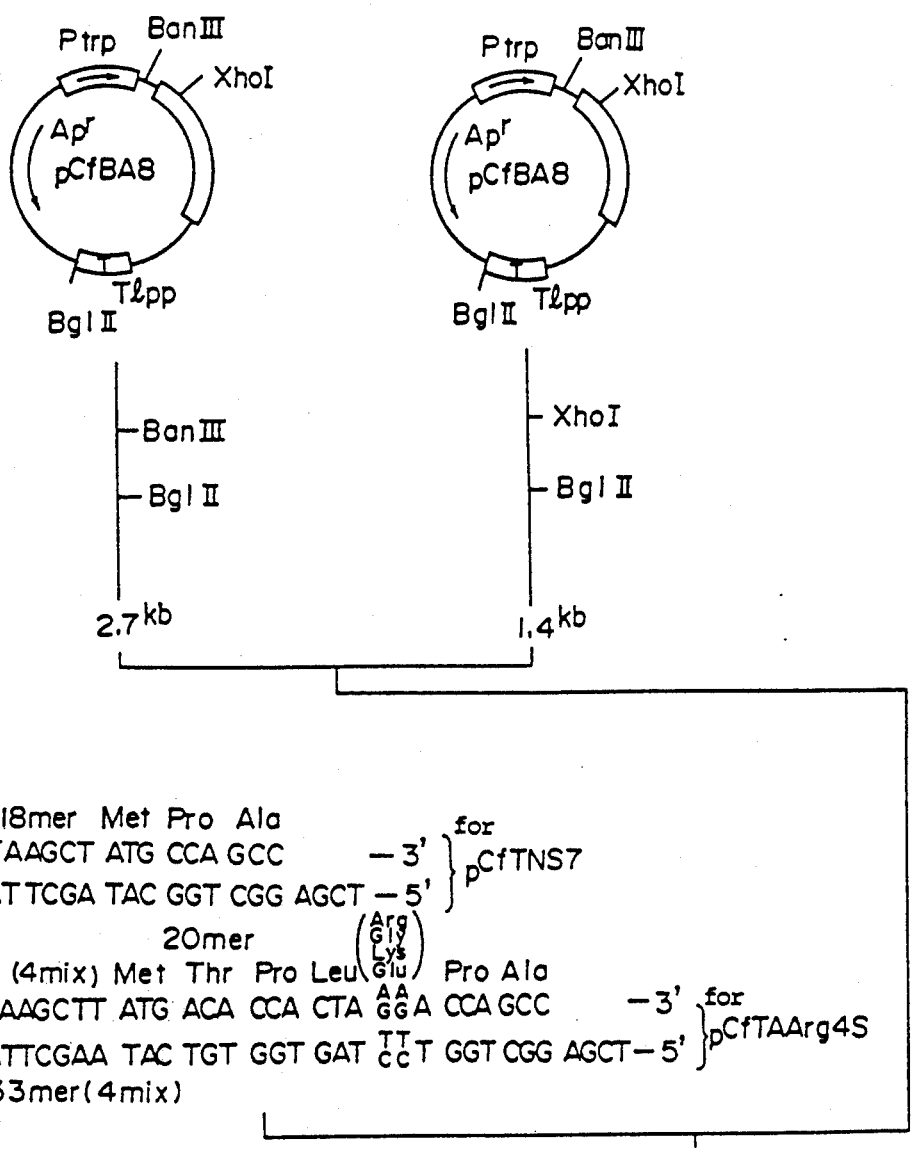
FIG. 14 shows construction schemes for the plasmids pCfTNS7 and pCfTAArg4S.
Figure 15:
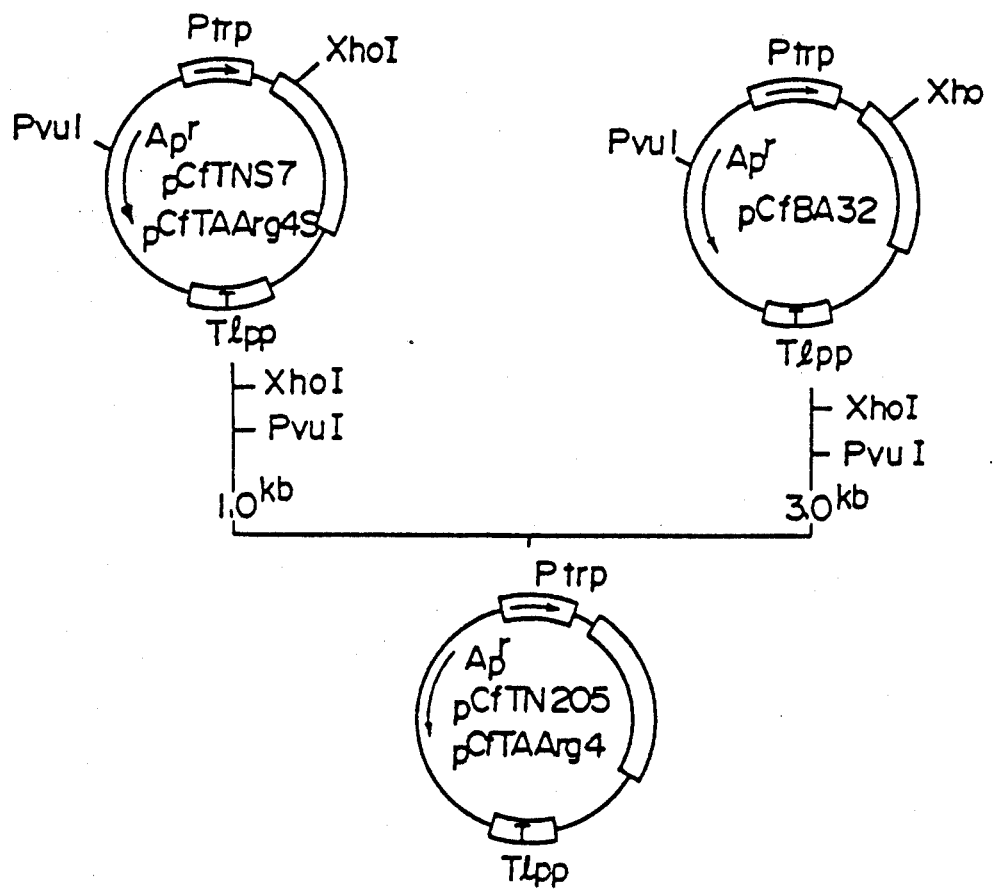
FIG. 15 shows a construction scheme for the plasmid pCfTN205 and pCfTAArg4.
Figure 16:
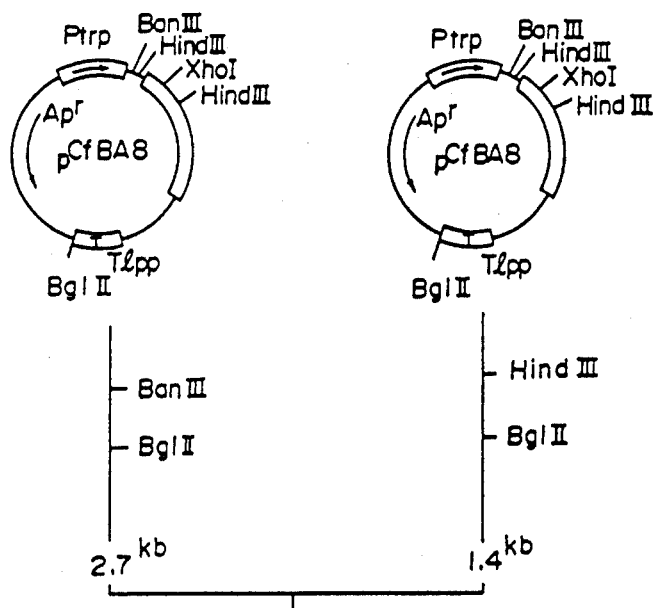
FIG. 16 shows construction schemes for the plasmids pCfTNS301 and pCfTNS401.
Figure 16:
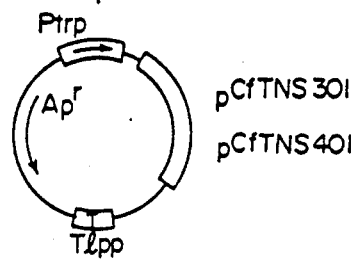

On the other hand, pCfBA8 is cleaved with BanIII, BqlII and a DNA fragment of about 2.7 kb is purified by the LGT method. Separately, pCfBA8 is cleaved with XhoI and BqlII and a DNA fragment of about 1.4 kb is purified by the LGT method. Ligation of the two fragments thus obtained and the synthetic DNA linker shown in FIG. 14 gives pCfTNS7 and pCfTAArg4S. In addition, as shown in FIG. 15, pCfTNS7 is cleaved with PvuI and XhoI and a DNA fragment of about 1 kb is purified by the LGT method. Separately, pCfBA32 is cleaved with PvuI and XhoI and a DNA fragment of about 3 kb is purified by the LGT method. The two fragments thus obtained are ligated together using T4 DNA ligase to give pCfTN205. Similarly, pCfTAArg4S is cleaved with PvuI and XhoI, a fragment of about 1 kb is purified by the LGT method and this fragment is ligated with a DNA fragment of about 3 kb derived from the above-mentioned plasmid pCfBA32 by cleavage with PvuI and XhoI, using T4 DNA ligase to give pCfTAArg4. Further, pCfBA8 is cleaved with BanIII and BqlII and a DNA fragment of about 2.7 kb is purified by the LGT method. Separately, pCfBA8 is cleaved with XhoI and BqlII and a DNA fragment of about 1.4 kb is purified by the LGT method. The two fragments thus-obtained and the synthetic linker shown in FIG. 16 are ligated together using T4 DNA ligase to give pCfTNS301 and pCfTNS401. Furthermore, as shown in FIG. 12, pCfBA8 is cleaved with XhoI, the protruding ends are converted to blunt ends by Klenow fragment treatment and, after further cleavage with PvuI, a DNA fragment of about 3 kb is purified by the LGT method. Separately, the ATG vector pTrS20 (reference Example 4) is cleaved with SacI, followed by conversion of the protruding ends to blunt ends by Klenow fragment treatment. After further cleavage with PvuI, a DNA fragment of about 1 kb is purified by the LGT method. The thus-obtained two fragments are ligated together using T4 DNA ligase to give pCfTNS501.

Figure 17:
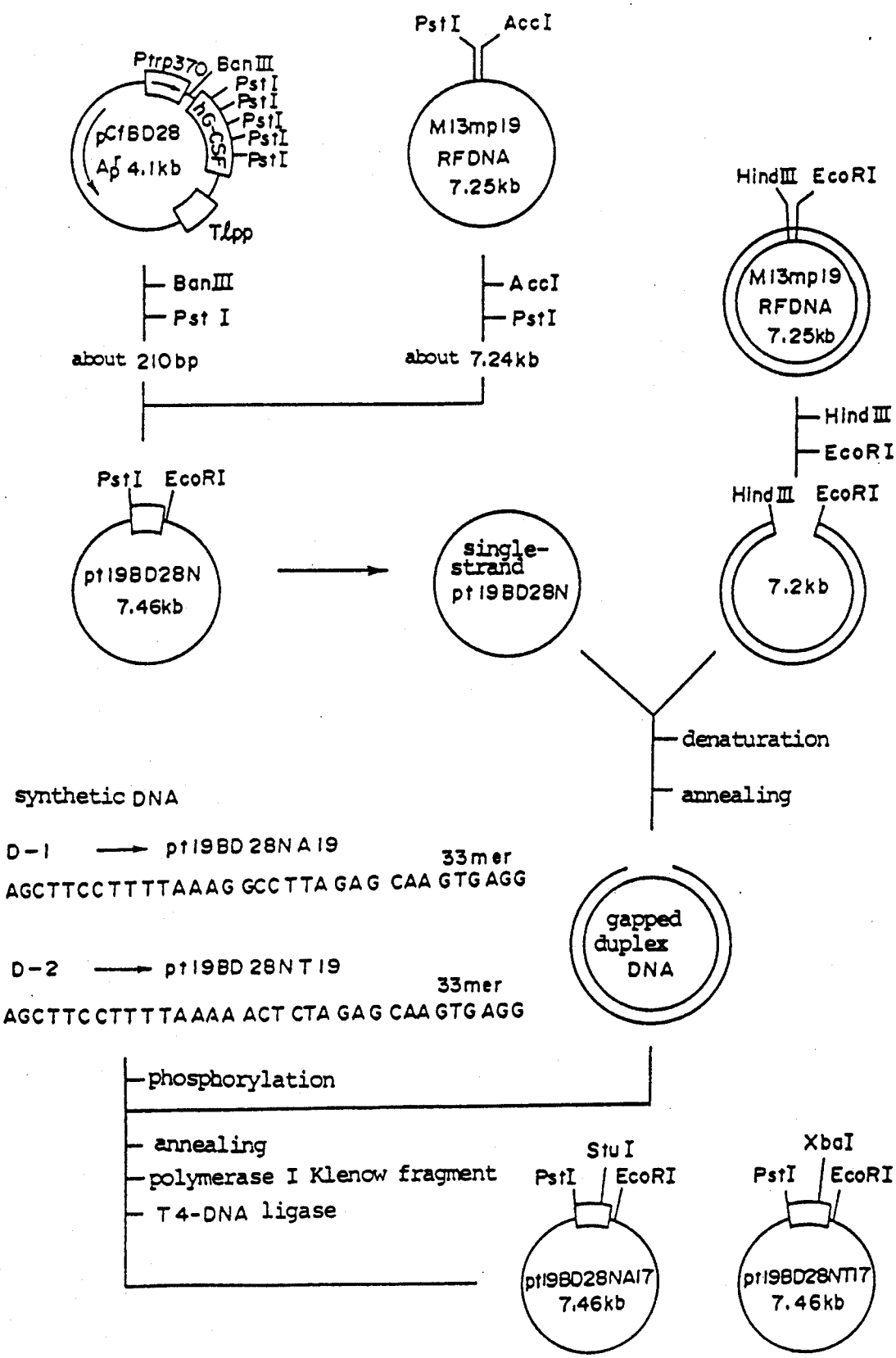
FIG. 17 (1) and (2) show construction schemes for the plasmids pCfBD28A17 and pCfBD28T17.
Figure 17:
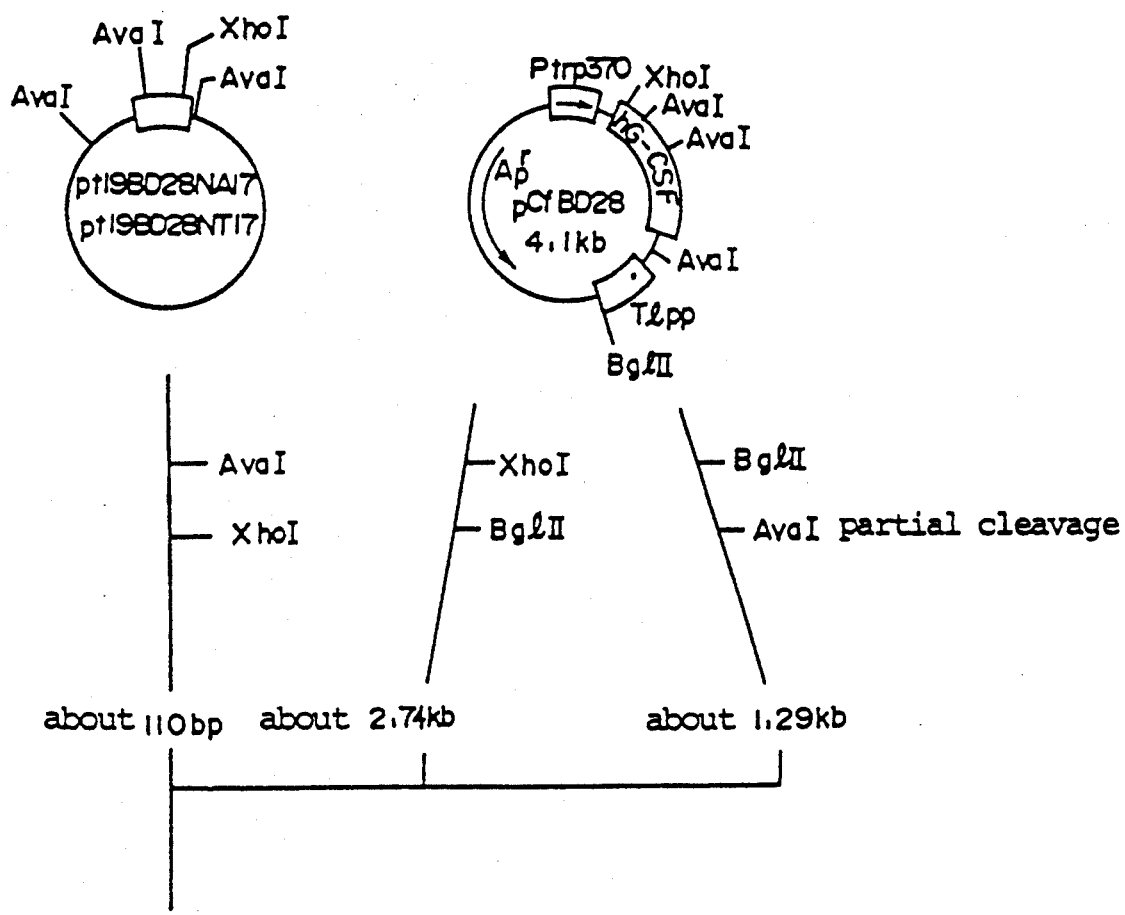
Figure 17:
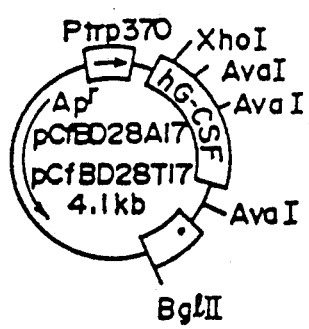

In an example where site-specific mutagenesis is utilized, pCfBD28 is cleaved with BanIII and PstI, as shown in FIG. 17, and a DNA fragment of about 210 bp is purified by the LGT method. Separately, the M13 phage vector M13mp19RF DNA is cleaved with AccI and PstI and a DNA fragment of about 7.24 kb is purified by the LGT method. The thus-obtained two DNA fragments are ligated together using T4 DNA ligase to give pt19BD28N. Then, this pt19BD28N is used to transfect E. coli JM105, and single-stranded pt19BD28N is recovered from the phase obtained. Similarly, as also shown in FIG. 17, the M13mp19RF DNA is cleaved with HindIII and EcoRI and a DNA fragment of about 7.2 kb is purified by the LGT method. After this 7.2 kb DNA fragment is mixed with the single-strand pt19BD28N obtained in the above manner, gapped duplex DNA formation is caused by denaturation treatment followed by annealing and the resultant gapped duplex DNA is purified by the LGT method. Then, this DNA is annealed with the synthetic DNA shown in FIG. 17 and thereafter circularized using the Klenow fragment and T4 DNA ligase. This circularized DNA is used to transfect E. coli JM105, whereby pt19BD28NA17 and pt19BD28NT17 with site-specific mutagenesis introduced therein are obtained. Further, as also shown in FIG. 17, pt19BD28NA17 and pt19BD27NT17 are cleaved with AvaI and XhoI and each DNA fragment of about 110 bp is purified by the LGT method. Separately, pCfBD28 is cleaved with XhoI and BglII and a DNA fragment of about 2.74 kb is purified by the LGT method. Further, separately, pCfBD28 is cleaved with BqlII and AvaI and a DNA fragment of about 1.29 kb is purified by the LGT method. Ligation of the thus-obtained DNA fragments of about 110 bp, about 2.74 kb and 1.29 kb using T4 DNA ligase gives pCfBD28A17 and pCfBD28T17, respectively.

The reaction conditions of the above recombination procedures are generally as follows:

The DNA digestion reaction in the presence of a restriction enzyme or enzymes is generally carried out using 0.1-20 μg of DNA in a reaction medium containing 2-200 mM (preferably 10-40 mM) Tris-HCl (pH 6.0-9.5, preferably 7.8-8.0), 0-200 mM NaCl and 2-20 mM (preferably 5-10 mM) MgCl$_2$ at 20°-70° C. (the optimal temperature varying depending on the restriction enzyme(s) used) for 15 minutes to 24 hours. The restriction enzymes are each used in an amount of 0.1-100 units (preferably 1-3 units) per microgram of DNA. Termination of the reaction is generally effected by heating at 55°-75° C. for 5-30 minutes. It is also possible to inactivate the restriction enzymes with a reagent such as phenol or diethyl pyrocarbonate.

The DNA fragments formed by the restriction enzyme digestion or the gapped duplex DNAs can be purified by the LGT method or by polyacrylamide gel electrophoresis [A. M. Maxam et al.: Proc. Natl. Acad. Sci. USA, 74, 560 (1977)], among others.

The DNA fragment ligation reaction is carried out in a reaction medium containing 2-200 mM (preferably 10-40 mM) Tris-HCl (pH 6.1-9.5, preferably 7.8-8.0), 2-20 mM (preferably 5-10 mM) MgCl$_2$, 0.1-10 mM (preferably 0.5-2.0 mM) ATP and 1-50 mM (preferably 5-10 mM) dithiothreitol at 1°-37° C. (preferably 3°-20° C.) for 15 minutes to 72 hours (preferably 2-20 hours), using 0.3-10 units of T4 DNA ligase.

The recombinant plasmid DNA obtained by ligation reaction may be introduced into E. coli according to the transformation method of Cohen et al. [S. N. Cohen et al.: Proc. Natl. Acad. Sci. USA, 69, 2110 (1972)], if desired.

The recombinant M13 phage RF DNAs formed by the ligation reaction are introduced into E. coli JM105 [J. Messing et al.: Gene, 33, 103 (1985)], using the known method of transfection [Yoshiyuki Kuchino et al.: Tanpakushitsu, Kakusan, Koso (Protein, Nucleic Acid and Enzyme), 29, 294 (1984)], as necessary.

The recombinant plasmid DNAs and recombinant M13 phage RF DNAs can be isolated from the respective E. coli transformants by the method of Birnboim et al. [H. C. Birnboim et al.: Nucleic Acids Res., 7, 1513 (1973)], for example.

The isolation of the single-strand DNA from the recombinant M13 phage is carried out by the known method [Yoshiyuki Kuchino et al.: Tanpakushitsu, Kakusan, Koso, 29, 294 (1984)].

The plasmid DNAs are examined for cleavage sites by agarose gel electrophoresis or polyacrylamide gel electrophoresis following cleavage with 1-10 restriction enzymes. Further DNA base sequence determination is performed, if necessary, by the dideoxy sequencing method using M13 phase [J. Messing et al.: Gene, 19, 269 (1982)].

The desired recombinant plasmid DNAs can be produced under the conditions such as mentioned above.

The hG-CSF polypeptide derivatives of the invention can be produced in the following manner.

Thus, E. coli K-12 HB101 is transformed with a suitable plasmid (e.g. pCfBD28), and a plasmid (e.g.

pCfBD28)-carrying transformant of E. coli is selected from among ampicillin resistant (hereinafter, Ap$^r$) colonies. Growing the plasmid (e.g. pCfBD28)-bearing strain of E. coli in a medium can lead to formation of an hG-CSF polypeptide derivative in the culture.

Any medium, whether synthetic or natural, may be used provided that it is suited for the growth of E. coli and for the production of the hG-CSF polypeptide derivative.

Usable carbon sources include glucose, fructose, lactose, glycerol, mannitol and sorbitol, among others, and usable nitrogen sources are $NH_4Cl$, $(NH_4)_2SO_4$, casamino acids, yeast extract, polypeptone, meat extract, Bactotryptone, corn steep liquor, etc. $K_2HPO_4$, $KH_2PO_4$, NaCl, $MgSO_4$, vitamin $B_1$, $MgCl_2$ and so forth may be used as other nutrient sources. The cultivation is carried out with aeration and stirring at a pH of 5.5–8.5 and a temperature of 18°–40° C. Cultivation for 5–90 hours leads to accumulation of an hG-CSF polypeptide derivative in cultured cells. The cells are then harvested from the culture and disrupted by ultra sonication. Centrifugation gives cell residues. The hG-CSF polypeptide derivative is extracted from the cell residues, purified, solubilized and regenerated by the method of Marston et al. [F. A. O. Marston et al.: BIO/TECHNOLOGY, 2, 800 (1984)]. Mouse bone marrow cells are treated with said derivative, and the hG-CSF polypeptide derivative is assayed by the method using the number of colonies formed in soft agar as an index.

In the practice of the invention, the hG-CSF activity is determined in the following manner. Bone marrow cells are aseptically collected from the femur of male C3H/He mice of 8–12 weeks of age (Shizuoka Laboratory Animal Center) and suspended in α-Minimum Essential Medium (Flow Laboratories; hereinafter referred to as α-MEM) supplemented with 10% of fetal bovine serum (FBS). Nylon wool (0.3 g; Wako Pure Chemical Industries' Nylon Fiber 146-04231) packed in a column is impregnated with 1.5 ml of the above cell suspension (about $5 \times 10^7$ cells), and the reaction is allowed to proceed in a 5% $CO_2$ incubator at 37° C. for 90 minutes. Then, α-MEM warmed to 37° C. in advance is passed through the column, and bone marrow cells unadsorbed on the nylon wool are collected as an effluent fraction. The cells are washed once with α-MEM and the cell concentration is adjusted to a predetermined one.

Thereafter, the myelopoietic stem cell colony-forming ability is determined by the method of Okabe et al. [T. Okabe, et al.: Cancer Research, 44, 4503–4506 (1986)]. Thus, 0.2 ml of the bone marrow cell suspension ($2 \times 10^6$ cells/ml) prepared in the above manner is admixed with a mixture of 0.2 ml of α-MEM, 0.4 ml of FBS and 0.2 ml of each 2-fold diluted sample. An equal volume (1.0 ml) of 0.6% agar (Difco, Agar purified 0506-01) solution maintained at 42° C. is admixed with the above mixture, and the resulting mixture is distributed in 0.5-ml portions onto a 24-well microtiter plate (Nunc' Multidisnh #143982) ($5 \times 10^4$ cells/well, n=3). After 7 days of incubation at 37° C. in a 5% $CO_2$ incubator, colonies comprising not less than 40 cells are counted under a microscope (Olympus X40). After counting, each colony is transferred onto a slide glass with care, fixed there with an acetone-formalin mixed solution for 30 minutes and subjected to esterase double stain by the method of Kubota et al. [K. Kubota, et al.: Exp. Mematology, 8, 339–344 (1980)] for indentification of the colony.

The potency of each sample is calculated based on the result of counting in the colony formation test for the 2-fold dilution as follows. The activity giving half of the maximum colony formation value obtained with intact G-CSF used as a standard is defined as 50 units. The potency (in units) is calculated according to this definition and using the factor 20 for multiplication for conversion to the activity per milliliter also in view of the dilution factor for the sample. The specific activity is expressed in terms of potency (units/mg) per unit weight (mg) of protein.

The hG-CSF polypeptide derivatives lacking one or more amino acids on the N-terminal side of the hG-CSF polypeptide can also be produced by enzymatic degradation.

The derivatives can, of course, be produced by enzymatic degradation of natural hG-CSF as the starting material. However, since natural hG-CSF is low in reactivity with the enzyme (protease), the use of a modified hG-CSF having increased reactivity against protease is preferable for producing such derivatives having high activity in good yields.

Preferably used as such starting materials are the modified hG-CSFs (a), (b), (c) and (d) shown in Table 2 as resulting from substitution of one or more amino acids on the N-terminal side of the hG-CSF polypeptide. Modifications (a), (b), (c) and (d) can be obtained by cultivating bacterial strains harboring the plasmids having the corresponding base sequences, namely pCfBC59 (NC59), pCfBD28 (ND28), pCfBC95 (NC95) and pCfTAArg4S (Arg 4S), respectively, followed by isolation and purification by known methods.

Suitably used as the enzyme are endoproteases such as serine protease and thiol protease. More specifically, there may be mentioned, for example, subtilisin A, subtilisin BPN', subtilisin Carlsberg, subtilisin novo, proteinase K, nagase, thermolysin, endoproteinase Arg-C, trypsin and α-chymotrypsin. The enzyme is used is an amount of $3.4 \times 10^{-6}$ to $8.5 \times 10^{-3}$ units per milligram of the starting material.

TABLE 2

Examples of N-terminally protease-susceptible hG-CSF derivatives

| Modified hG-CSF | Substituent amino acids | Plasmid* |
|---|---|---|
| a | $Tyr^1$, $Ile^3$, $Arg^4$, $Ser^5$ ... $Ser^{17}$ | NC59 |
| b | $Ala^1$, $Thr^3$, $Tyr^4$, $Arg^5$ ... $Ser^{17}$ | ND28 |
| c | $Ile^1$, $thr^3$, $Arg^4$, $Ser^5$ ... $Ser^{17}$ | NC95 |
| d | $Arg^4$, ... $Ser^{17}$ | Arg4S |

*Amino acids after substitution. The superscripts indicate the position numbers of the relevant amino acids from the N terminus.

Following dissolution of the starting material in an aqueous solution such as Tris hydrochloride buffer or phosphate buffer and addition of an enzyme, the enzymatic reaction is carried out at 10°–37° C. for 30 minutes to 3 days.

The total protein quantity and the protein quantity are determined by the following methods:

The total protein determination is performed by the method of M. M. Bradford [M. M. Bradfor: Anal. Biochem., 72, 248 (1976)].

The protein quantity is determined by SDS-polyacrylamide gel electrophoresis by the method of Laemmli [U. K. Laemmli: Nature, 227, 680 (1970)] followed by measurement on a chromatoscanner (Shimadzu CS-930).

The N-terminal amino acid sequence of the peptide obtained after enzymatic cleavage is determined using an automatic amino acid sequencer "Gas-Phase Protein Sequencer Model 470A" (Applied Biosystems) in combination with a Spectra Physics high-performance liquid chromatograph.

The hG-CSF derivative of the present invention can be purified by using a monoclonal antibody binding to said derivative.

A monoclonal antibody binding to the hG-CSF derivative of the present invention, for example, ND28 having the following amino acid sequence as described above, can be prepared as follows.

TABLE 3

| | | | | | | | | | | | | | | | | | | | |
|---|---|---|---|---|---|---|---|---|---|---|---|---|---|---|---|---|---|---|---|
| Ala | Pro | Thr | Tyr | Arg | Ala | Ser | Ser | Leu | Pro | Gln | Ser | Phe | Leu | Leu | Lys | Ser | Leu | Glu | Gln |
| | | | | | | | | | 10 | | | | | | | | | | 20 |
| Val | Arg | Lys | Ile | Gln | Gly | Asp | Gly | Ala | Ala | Leu | Gln | Glu | Lys | Leu | Cys | Ala | Thr | Tyr | Lys | Leu | Cys | His | Pro | Glu | Glu | Leu | Val | Leu | Leu |
| | | | | | | | 30 | | | | | | | | 40 | | | | | | | | | | 50 |
| Gly | His | Ser | Leu | Gly | Ile | Pro | Trp | Ala | Pro | Leu | Ser | Ser | Cys | Pro | Ser | Gln | Ala | Leu | Gln | Leu | Ala | Gly | Cys | Leu | Ser | Gln | Leu | His | Ser |
| | | | | | | | 60 | | | | | | | | 70 | | | | | | | | | | 80 |
| Gly | Leu | Phe | Leu | Tyr | Gln | Gly | Leu | Leu | Gln | Ala | Leu | Glu | Gly | Ile | Ser | Pro | Glu | Leu | Gly | Pro | Thr | Leu | Asp | Thr | Leu | Gln | Leu | Asp | Val |
| | | | | | | | 90 | | | | | | | | 100 | | | | | | | | | | 110 |
| Ala | Asp | Phe | Ala | Thr | Thr | Ile | Trp | Gln | Gln | Met | Glu | Glu | Leu | Gly | Met | Ala | Pro | Ala | Leu | Gln | Pro | Thr | Gln | Gly | Ala | Met | Pro | Ala | Phe |
| | | | | | | | 120 | | | | | | | | 130 | | | | | | | | | | 140 |
| Ala | Ser | Ala | Phe | Gln | Arg | Arg | Ala | Gly | Gly | Val | Leu | Val | Ala | Ser | His | Leu | Gln | Ser | Phe | Leu | Glu | Val | Ser | Tyr | Arg | Val | Leu | Arg | His |
| | | | | | | | 150 | | | | | | | | 160 | | | | | | | | | | 170 |
| Leu | Ala | Gln | Pro | | | | | | | | | | | | | | | | |
| | | | 174 | | | | | | | | | | | | | | | | |

(1) Preparation of immunized animal cells

Mice (or rats) are immunized with ND28, produced by *Escherichia coli* based on DNA recombination techniques (Example 8), and the splenic cells are taken out from the immunized animals.

The immunization is carried out by administering ND28 (10 to 100 μg/head) subcutaneously, intravenously or intraperitoneally to mice of 8- to 10-week age, together with a suitable adjuvant (for example, Complete Freund's Adjuvant, or aluminum hydroxide gel and purtussis vaccine), 2 to 10 times at intervals of one to two weeks; taking blood samples from the venous plexus at the eyeground one week after each administration; and measuring the anti-ND28 antibody titer of the serum by the solid-phase immunoassay as explained below.

The antibody titer is measured by the solid-phase enzyme immunoassay described in "Enzyme Immunoassay" (published from Igaku-shoin in 1978).

100 μl of a specific antigen solution [a 10 μg/ml ND28 solution in a phosphate-buffered saline (PBS) (solution containing 1.83 g disodium phosphate, 0.21 g monopotassium phosphate and 7.65 g sodium chloride in 1 liter of distilled water; pH 7.2); or a solution of another antigen or BSA in PBS when checking for cross reaction] is dispensed in each well of a 96-well EIA plate (Flow Laboratories, U.S.A.), and the plate is allowed to stand for 12 to 19 hours at 4° C. to coat the bottom of each well with antigen. 1% BSA/PBS solution (200 μl/well) is then dispensed, and the plate is allowed to stand for 12 to 19 hours at 4° C. to coat the protein-binding residues on the bottom of each well with BSA. After thorough washing with PBS, serial dilutions of a sample (mouse antiserum, hybridoma culture supernatant, or purified antibody) are dispensed as the first antibody in amount of 50 μ/well and allowed to stand at 4° C. for 12 to 19 hours or at 22° to 26° C. for three to four hours. After washing six times with PBS, a 1:400 dilution of rabbit antimouse-immunoglobulin/peroxidase conjugate (produced by DAKO and supplied from Kyowa Medex) is then dispensed as the second antibody in amounts of 100 μl/well and allowed to stand at 22° to 26° C. for two hours. After washing with PBS, 100 μl of an ABTS substrate solution [prepared by adding, immediately before use, 1 μl/ml hydrogen peroxide to a solution of 550 mg diammonium 2,2'-azino-bis(3-ethylbenzothiazoline-6-sulfonate) in 1 liter of 0.1 M citrate buffer (pH 4.2)] is added to each well, and the color thus developed is measured (at $OD_{415nm}$).

The mice in which the anti-ND28 antibody titer ($OD_{415nm}$) is more than $10^3$ times as high as that of normal mouse serum are used as the suppliers for the immunized animal cells.

ND28 is intraperitoneally administered to these immunized mice (100 μg/head) three to four days before cell fusion to effect the last immunization, and the spleen is removed from each mouse to prepare the splenic cells to be used for cell fusion.

(2) Preparation of myeloma cells

A mouse-derived cell line is used as the myeloma cells in this invention. Illustrative examples include 8-azaguanine resistant mouse (derived from BALB/c) myeloma cell lines, such as P3-X63 Ag8-U1 (P3-U1) [Current topics in Microbiology and Immunology, 81, 1–7 (1978)], P3-NSI/1-Ag4.1 (NS-1) [European J. Immunology, 6, 511–519 (1976)], SP2/0-Ag14 (SP-2) [Nature, 276, 269–270 (1978)], P3-X63-Ag8.653 (653) [J. Immunology, 123, 1548–1550 (1979)], and P3-X63-Ag8 (X63) [Nature, 256, 495–497 (1975)]. These cells lines, subcultured in 8-azaguanine medium [prepared by adding 1.5 mM glutamine, $5 \times 10^{-5}$ M 2-mercaptoethanol, 10 μg/ml gentamycin and 10% fetal calf serum (FCS) to RPMI-1640 medium, and further adding, to the normal medium thus obtained, 15 μg/ml 8-azaguanine], are changed to the normal medium three to four days before cell fusion to secure more than $2 \times 10^7$ cells on the day of cell fusion.

(3) Cell fusion

ND28 is intraperitoneally administered (100 μl/head) to the mice immunized in Step (1) above, and the spleen is removed from each mouse three to four days later to prepare splenic cells. These splenic cells and the myeloma cells obtained in Step (2), both thoroughly washed with MEM medium (product of Nissui Seiyaku) or PBS, are mixed together at a cell number ratio of 5~10:1, and the mixture is subjected to centrifugation. After discarding the supernatant, the cell pellet is thoroughly loosened, a mixed solution of 1 to 4 g polyethylene glycol (PEG-1000~4000, product of Wako Pure Chemical Industries), 1 to 4 ml MEM medium and 0.5 to 1.0 ml dimethyl sulfoxide was added with stirring in an amount of 0.1 to 1.0 ml/$10^8$ (splenic cell), and the mixture is allowed to stand for 0.5 to 10 minutes. MEM medium (0.5 to 3 ml) is then added several times at intervals of 0.5 to 2 minutes, and 30 to 60 ml MEM medium is finally added. The resulting mixture is centrifuged, the supernatant is discarded, the cell pellet thus obtained is gently loosened, 50 to 200 ml of the normal medium is added, and the mixture is gently treated with a measuring pipette to suspend the cells. This suspension is dispensed on a culture plate (half the volume of each cell) and incubated at 37° C. for 10 to 30 hours in a 3~7%-$CO_2$ incubator. HAT medium (the normal medium supplemented with $10^{-5}$ to $10^{-3}$ M hypoxanthine, $10^{-6}$ to $10^{-4}$ M thymidine and $10^{-8}$ to $10^{-7}$ M aminopterin) is then added to the culture plate (half the volume of each well), and incubation is continued for an additional 10 to 30 hours. After that, half the volume of supernatant in each well is discarded and the same volume of HAT medium is supplied at intervals of 10 to 30 hours over a period of one to three days, and incubation is continued at 37° C. for 10 to 14 days.

With the wells in which growth of fused cell colonies is observed, half the volume of supernatant is discarded, the same volume of HT medium (HAT medium with aminopterin removed therefrom) is added, and this medium replacement is repeated at intervals of 10 to 30 hours over a period of one to three days.

After incubation in HT medium for three to four days, a part of culture supernatant is taken out and measured for the anti-ND28 antibody titer by the enzyme immunoassay described above.

With the wells in which an appreciable magnitude of antibody titer is observed, cloning is repeated two to four times by the limiting dilution method, and the cells that show consistent values of antibody titer are selected as a hybridoma cell capable of producing anti-ND28 monoclonal antibody.

(4) Preparation of monoclonal antibody

The monoclonal-antibody producing hybridoma obtained in Step (3) is intraperitoneally administered to pristane-treated BALB/c female mice of 8- to 10-week age (2 to $4 \times 10^6$ cell/head). The hybridoma will cause ascites carcinoma in 10 to 21 days. The ascites is taken out of the mice, centrifuged to remove the solid matter, and subjected to ammonium sulfate precipitation (50% and 40% saturation), followed by dialysis against PBS (pH 7.2) for one to two days. The dialyzate thus obtained may be submitted to quantitative analysis of ND28 as crude monoclonal antibody.

This crude product can be purified, when required, by passing it through a DEAE-cellulose column or a Protein A-Sepharose column and collecting the IgG fraction.

The isotype and subclass of the monoclonal antibody is determined according to the Ouchterlony method (Biochemical Experiment No. 15 (p74) in "A Guide to Experimental Immunology" published from Gakkai Shuppan Center in 1981).

The monoclonal-antibody producing hybridoma of this invention was named KM-498, and the monoclonal antibody KM-498 produced by this hybridoma cell was identified as belonging to the $IgG_1$ isotype.

The antigen specificity of the monoclonal antibody KM-498 is shown in Example 23 given below.

Described below is an example of a ND28 purification procedure using the monoclonal antibody of this invention.

A solution of 10 mg of the monoclonal antibody of this invention in 1 ml of PBS is allowed to react with 1 ml of CNBr-activated Sepharose-4B (Pharmacia Fine Chemicals) to give immobilized monoclonal antibody. This is charged in a column, and a solution containing ND28 (3 mg or less) prepared by DNA recombination techniques is passed through that column. As a result, 95 to 100% of the ND28 can be adsorbed on the column. Elution with an aqueous solution containing 7 M urea and 1 M NaCl (pH 7.0) yields about 80% of the adsorbed ND28 as a fraction. Approximately 5000-fold purification can thus be achieved by a single column treatment. In contrast, natural G-CSF is not adsorbed at all on the above column.

The monoclonal antibody of this invention can be used for the quantitative analysis of ND28 by the enzyme immunoassay using a solid-phase sandwich assay technique.

In using hG-CSF as a therapeutic agent, it is desirable that hG-CSF be stable and stay long in the blood after administration and its antigenecity be attenuated.

The present invention have further found that when at least one amino group in hG-CSF or derivatives thereof is chemically modified, the resulting polypeptide stays longer in blood than the unmodified polypeptide.

The chemical modification of hG-CSF or derivatives thereof can be effected by substitution of at least one amino group of a polypeptide having hG-CSF activity with a group of the formula

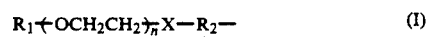

$$R_1 \!+\! OCH_2CH_2 \!\!\rightarrow_{\overline{n}}\!\! X \!-\! R_2 \!-\! \tag{I}$$

wherein $R_1$ is an alkyl or alkanoyl group; n is an optionally variable positive integer; X is O, NH or S; $R_2$ is

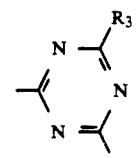

where $R_3$ is OH, Cl, O—$(CH_2CH_2O)_n$—$R_1$ (where $R_1$ and n are as defined above) or $(CO)_m$—$(CH_2)_l$CO (where m is 0 or 1; l is optionally variable positive integer).

The starting polypeptide having hG-CSF activity may be any polypeptide having hG-CSF activity such as a polypeptide having the amino acid sequence shown in Table 1, a polypeptide available upon replacement of at least one amino acid residue of the amino acid sequence shown in Table 1 with another kind of amino acid, e.g. The hG-CSF derivatives shown in Table 3, or a polypeptide deficient in 1 to 11 amino acid residues at the N-terminus of the amino acid sequence shown in Table 1. Aside from the above polypeptides, the hG-CSF derivatives described in EP-A-243153, EP-A-237545 and WO-A-8701132 can also be employed.

Referring to the chemically modifying group to be used in accordance with this invention, the alkyl and alkanoyl groups mentioned as protective groups for the terminal oxygen atom are $C_{1-18}$ alkyl groups (for example, methyl, ethyl, propyl, etc.) and $C_{1-18}$ alkanoyl groups (for example, formyl, acetyl, propionyl, etc.).

The positive integer n is not more than 500 and preferably 7 to 230.

The positive integer l is not more than 100 and preferably 0 to 6. The molecular weight of said chemically modifying group is not more than 30,000 and preferably in the range of 300 to 10,000.

The chemically modified hG-CSF of this invention is produced, for example, by condensation of hG-CSF with a halide of the formula

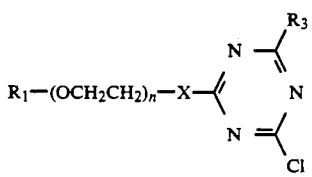

wherein $R_1$, n, X and $R_3$ are as defined hereinbefore or by condensation of hG-CSF with a carboxylic acid of the formula

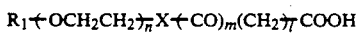

wherein $R_1$, n, X, m and l are as defined hereinbefore.

The halide mentioned above can be prepared by condensing

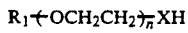

(wherein $R_1$, n and X are as defined above) with cyanuric chloride [Matsushima, A. et al.: Chemistry Letters, 773–776, 1980); Abuchowski, A. et al.: Journal of Biological Chemistry 252 (12) 3575–3581, 1977]. This halide is reactive and can therefore by directly reacted with a polypeptide having hG-CSF activity.

The carboxylic acid mentioned above can be prepared by subjecting

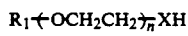

wherein $R_1$, n and X are as defined hereinbefore, to dehydrative condensation with a carboxyl group of an alkanedicarboxylic acid or reaction with a halogenated monocarboxylic acid so as to introduce a carboxylic group or to an oxidation reaction of its terminal hydroxyl group to convert the latter to a carboxyl group. This carboxylic acid is not reactive and must, therefore, be activated before use. This activation of the carboxylic acid can for example be accomplished by converting it to an acitve ester with, for example, N-hydroxysuccinimide, N-hydroxyphthalimide, 1-hydroxybenzotriazole, p-nitrophenol or the like, a mixed acid anhydride with isobutyl chloroformate, ethyl chloroformate or the like, or to be an acid halide using a halogenating agent such as thionyl chloride. [All of the above methods are described, for example, in Peptide Gosei (Peptide Synthesis) (Nobuo Izumiya et al., Maruzen)].

To this polypeptide having hG-CSF activity is added the above-mentioned halide or acitve carboxylic acid compound in a proportion (mole ratio) of 2 to 100 times the amount of amino groups present in the polypeptide molecule and the mixture is allowed to react at a temperature of 4° to 37° C., preferably 4° to 10° C., and pH 7 to 10 for 1 hour to 2 days, preferably 1 to 24 hours, whereby the desired chemically modified hG-CSF is produced.

The degree of chemical modification can be ascertained by quantitating the amount of decrease in free amino groups with trinitrobenzenesulfonic acid or monitoring a change in mobility of chemically modified hG-CSF by sodium dodecylsulfate (SDS)-polyacrylamide gel electrophoresis.

The determination of protein quantity of chemically modified hG-CSF is carried out by one of the following test methods.

Test Method 1

The method of Lowry (Lowry, O. H. et al.: Journal of Biological Chemistry 193, 265, 1951).

Test Method 2

The method of Laemmli (Laemmli, U.K.: Nature 227, 680, 1970) in which SDS-polyacrylamide gel electrophoresis is followed by determination with a chromatoscanner (CS-930, Shimadzu).

DESCRIPTION OF THE PREFERRED EMBODIMENTS

The following examples are illustrative of the invention.

EXAMPLE 1

Construction of the hG-CSF expression plasmid pCfTA1 (cf. FIG. 1)

A 2-μg portion of the pCSF1-2 DNA obtained in Reference Example 1 was dissolved in a total amount of 20 μl of a solution (hereinafter referred to as "Y-100 buffer") containing 10 mM Tris-HCl (pH 7.5), 7 mM MgCl₂, 6 mM 2-mercaptoethanol and 100 mM NaCl, 10 units each of the restriction enzymes ApaI (Boehringer Mannheim) and BamHI (Takara Shuzo; hereinafter, unless otherwise specified, all the restriction enzymes used were obtained from Takara Shuzo) were added, and the reaction was carried out at 37° C. for 4 hours. From the reaction mixture, there was purified and recovered 0.4 μg of a 1.5 kb DNA fragment by the LGT method.

Separately, 2 μg of the plasmid pLSA1 prepared by the method of Reference Example 3 was dissolved in 20 μl of Y-100 buffer, 10 units each of the restriction enzymes BanIII (Toyobo) and BamHI were added, and the reaction was carried out at 37° C. for 4 hours. From this reaction mixture, there was purified and recovered 0.8 μg of a 2.8 kb DNA fragment by the LGT method.

On the other hand, the following DNA linker was synthesized to provide the codons coding for the first to fifth N-terminal amino acids of the mature hG-CSF polypeptide [threonine[1] (ACA or ACT), proline[2] (CCA or CCT), leucine[3] (CTA), glycine[4] (GGC) and proline[5] (CCC)] and the initiation codon (ATG) required for the expression and for adjusting the distance between the SD sequence and ATG downstream from the tryptophan promoter (Ptrp) to an appropriate length between 6-18 bp:

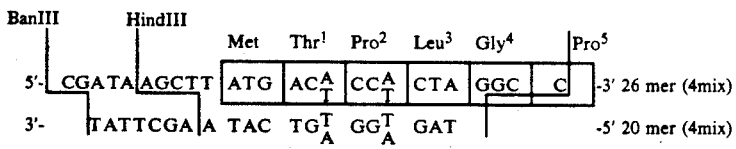

First, the 26-mer and 20-mer single-strand DNAs were synthesized by the phosphotriester method [R. Crea et al.: Proc. Nat. Acad. Sci. USA, 75, 5765 (1978)]. The 26-mer and 20-mer (each 2 μg) were dissolved in 40 μl of a buffer (hereinafter referred to as "T4 kinase buffer") containing 50 mM Tris-HCl (pH 7.5), 10 mM MgCl₂, 5 mM dithiothreitol, 0.1 mM EDTA and 1 mM ATP, 30 units of T4 polynucleotide kinase (Takara Shuzo; hereinafter the same shall apply) was added, and the phosphorylation reaction was carried out at 37° C. for 60 minutes.

In 25 μl of a buffer (hereinafter referred to as "T4 ligase buffer") containing 20 mM Tris-HCl (pH 7.6), 10 mM MgCl₂, 10 mM dithiothreitol and 1 mM ATP, there were dissolved 0.4 μg of the pCSF1-2-derived ApaI BamHI fragment (1.5 kb) obtained in the above manner and 0.2 μg of the pLSA1-derived BanIII-BamHI fragment (2.8 kb) obtained in the above manner; 0.1 μg of the above-mentioned DNA linker was added to the mixture. To this mixed solution, there was further added 6 units of T4 DNA ligase (obtained from Takara Shuzo; hereinafter the same shall apply), and the ligation reaction was carried out at 4° C. for 18 hours.

The thus-obtained recombinant plasmid mixture was used to transform *E. coli* HB101 [Bolivar et al.: Gene, 2, 75 (1977)] by the method of Cohen at al. [S. N. Cohen et al.: Proc. Natl. Acad. Aci. USA, 69, 2110 (1972)] (hereinafter, this method was used for transforming *E. coli*), and an Ap$^r$ colony was obtained. The plasmid DNA was recovered from the cultured cells of this colony by the known method [H. C. Birnboim et al.: Nucleic Acids Res., 7, 1513 (1979)] (hereinafter, this method was used for plasmid DNA separation). The structure of the plasmid obtained was confirmed by cleavage with BanIII, RsaI, PstI HindIII and BglII followed by agarose gel electrophoresis. This plasmid is called pCfTA1. The base sequence of pCf TA1 in the neighborhood of the BanIII and HindIII sites was confirmed to be as follows by the dideoxy sequencing method using M13 phage:

EXAMPLE 2

Construction of the plasmid pCfTB20 lacking in part of the 3'-nontranslational region of the hG-CSF cDNA In 20 μl of Y-100 buffer, there was dissolved 2 μg of the hG-CSF expression plasmid pCf TA1 (4.3 kb) obtained in Example 1, 4 units of the restriction enzyme BamHI was added, and the digestion reaction was carried out at 37° C. for 4 hours. After extraction with a mixture of an equal volume of phenol and chloroform (hereinafter referred to as phenol-chloroform extraction), 1.8 μg of a DNA fragment was recovered by precipitation with ethanol. This DNA fragment was dissolved in 20 μl of a buffer (hereinafter referred to as "Klenow buffer") containing 50 mM Tris-HCl (pH 7.8), 7 mM MgCl₂ and 6 mM mercaptoethanol, then dATP, dTTP, dCTP and dGTP were added each to a concentration of 1 mM and, after further addition of 4 units of DNA polymerase I Klenow fragment (obtained from Takara Shuzo; hereinafter the same shall apply), and the reaction was carried out at room temperature for 1 hour to thereby convert the protruding ends to blunt ends. After phenol-chloroform extraction, 1.6 μg of a DNA fragment was recovered by ethanol precipitation. This DNA fragment was dissolved in 20 μl of Y-100 buffer, 10 units of EcoRI was added, and the cleavage reaction was carried out at 37° C. for 4 hours. From the reaction mixture, there was obtained 1 μg of a 2.5 kb DNA fragment [BamHI(blunt)-EcoRI fragment] by the LGT method.

Separately, 2 μg of pCf TA1 was dissolved in 20 μl of Y-100 buffer, 10 units of EcoRI was added, and the cleavage reaction was carried out at 37° C. for 4 hours. Thereafter, NaCl was added to an NaCl concentration of 150 mM, then 10 units of DraI was added, and the cleavage reaction was carried out at 37° C. for 4 hours. After confirmation of complete cleavage by agarose gel electrophoresis, 0.2 μg of an hG-CSF cDNA-containing 1.0 kb DNA fragment (EcoRI-DraI fragment) was purified and recovered by the LGT method.

In 25 μl of T4 ligase buffer, there were dissolved 0.2 μg of the BamHI (blunt)-EcoRI fragment (2.5 kb) and 0.2 μg of the EcoRI-DraI fragment (1.0 kb) each obtained in the above manner, 6 units of T4 DNA ligase was added to the resultant mixture, and the ligation reaction was carried out at 4° C. for 18 hours.

The thus-obtained recombinant plasmid mixture was used to transform *E. coli* HB101, and an Ap$^r$ colony was obtained. From cultured cells derived from this colony, a plasmid DNA was recovered. The structure of the plasmid obtained was confirmed by agarose gel electrophoresis following cleavage with HindIII and PstI. This plasmid is called pCfTB20.

EXAMPLE 3

Construction of the plasmids coding for polypeptides resulting from substitution of the N-terminal amino acid of hG-CSF, namely pCfTL23, pCfTL38, pCfTL35 and pCfTL41 (cf. FIG. 3)

In 60 μl of Y-100 buffer, there was dissolved 3 μg of pCSF1-2 (4.5 kb) obtained by the method of Reference Example 1, 8 units each of the restriction enzymes ApaI (Boehringer Mannheim) and BamHI were added, and the cleavage reaction was carried out at 37° C. for 3 hours. From this reaction mixture, there was obtained about 0.4 μg of a DNA fragment of about 1.5 kb (ApaI-BamI fragment) containing most of the hG-CSF gene.

Separately, 2 μg of pGEL1 [Sekine et al.: Proc. Natl. Acad. Sci. USA, 82, 4306 (1985)] (obtained from a culture of *E. coli* IGEL1 FERM BP-629 by the conventional method) (3.4 kb) was dissolved in 40 μl of Y-100 buffer, 4 units each of the restriction enzymes HindIII, BamHI and PstI were added, and the cleavage reaction was carried out at 37° C. for 3 hours. From the reaction mixture, there was obtained about 0.5 µg of a DNA fragment of about 1.7 kb (PstI BamHI fragment) containing the lipoprotein-derived terminator by the LGT method.

Separately, 3 µg of pKYP10 prepared by the method described in U.S. Pat. No. 4,686,191 was dissolved in 60 µl of Y-100 buffer, 6 units each of the restriction enzymes BanIII (Toyobo) and PstI were added, and the cleavage reaction was carried out at 37° C. for 3 hours. From the reaction mixture, there was obtained about 0.5 µg of a DNA fragment of about 1.1 kb (BanIII-PstI fragment) containing the tryptophan promoter (Ptrp) by the LGT method.

On the other hand, in view of the necessity of substituting the N-terminal amino acid of mature hG-CSF, namely Thr, with Ser, Cys, Arg or Gly and providing the initiation codon (ATG) required for expression and also in view of adjusting the distance between the SD sequence and ATG downstream from Ptrp to an appropriate length of 6–18 bp, and for other reasons, the following DNA linker was synthesized:

| pCfTL23 | Met Gly Pro Leu Gly Pro Ala |
|---|---|
|  | ATG GGT CCA CTA GGC CCT GCC |
| pCfTL38 | Met Ser Pro Leu Gly Pro Ala |
|  | ATG AGT CCA CTA GGC CCT GCC |
| pCfTL35 | Met Cys Pro Leu Gly Pro Ala |
|  | ATG TGT CCA CTA GGC CCT GCC |
| pCfTL41 | Met Arg Pro Leu Gly Pro Ala |
|  | ATG CGT CCA CTA GGC CCT GCC |

The substitution of the N-terminal Thr of mature hG-CSF was confirmed in the pCfTL23-encoded hG-CSF derivative, which is called hG-CSF[Gly$^1$]. Similarly, N-terminal amino acid substitution by Ser was confirmed in CSF[Ser$^1$], substitution by Cys in the pCfTL35-encoded hG-CSF derivative, which is called hG-CSF[Cys$^1$], and substitution by Arg in the pCfTL41-encoded hG-CSF derivative, which is called hG CSF[Arg$^1$].

EXAMPLE 4

Construction of plasmids, pCfTM14, pCfTM17 and pCfTM113, which code for polypeptides resulting from

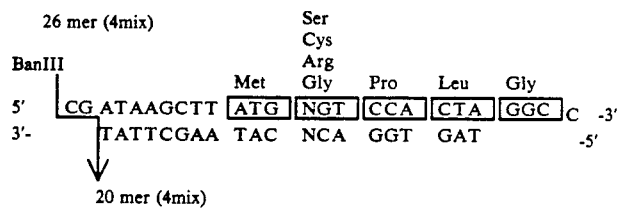

In the above formula, N is one of the bases G, A, T and C.

First, the 26-mer and 20-mer single-strand DNAs were synthesized by the ordinary phosphotriester method. The 26-mer and 20-mer (each 20 picomoles) were dissolved in 40 µl of T4 kinase buffer, 6 units of T4 polynucleotide kinase (Takara Shuzo) was added, and the phosphorylation reaction was carried out at 37° C. for 60 minutes.

Then, 0.3 µg of the pCSF1-2-derived ApaI-BamHI fragment (about 1.5 kb), 0.2 µg of the pGEL1-derived PstI-BamHI fragment (about 1.7 kb) and 0.2 µg of the expression vector pKY10-derived BanIII-PstI fragment (about 1.1 kb), each obtained in the above manner, were dissolved in a total of 30 µl of T4 ligase buffer, and about 1 picomole of the above DNA linker was added to the mixture solution. After further addition of 6 units of T4 DNA ligase to the solution, the ligation reaction was carried out at 4° C. for 18 hours.

The recombinant plasmid-containing reaction mixture was used to transform E. coli C600SF8 (FERM BP-1070) [Cameron et al.: Proc. Natl. Acad. Sci. USA, 72, 3416 (1975)], and Ap$^r$ colonies were obtained. From these transformants, there were separated and purified the plasmid DNAs by known methods. The structure of each of the plasmid DNAs was confirmed by cleavage with PstI, EcoRI and BanIII, followed by polyacrylamide gel electrophoresis. The plasmids obtained in this way are called pCfTL23, pCfTL38, pCfTL35 and pCfTL41, as shown in FIG. 3. The sequences in the vicinity of the N terminus of the hG-CSF derivative genes in said plasmids were confirmed by the dideoxy sequencing method using M13 phage to be as follows:

substitution of the N-terminal and third amino acids of hG-CSF (cf. FIG. 4)

In 60 µl of Y-100 buffer, there was dissolved 3 µg of pCSF1-2 (4.5 kb) obtained by the procedure of Reference Example 1, 8 units each of ApaI and BamHI were added, and the cleavage reaction was carried out at 37° C. for 3 hours. From this reaction mixture, there was obtained about 0.4 µg of a DNA fragment of about 1.5 kb (ApaI-BamHI fragment) containing most of the hG-CSF gene by the LGT method.

Separately, 2 µg of pGEL1 (3.4 kb) was dissolved in 40 µl of Y-100 buffer, 4 units each of the restriction enzymes HindIII, BamHI and PstI were added, and the cleavage reaction was carried out at 37° C. for 3 hours. From this reaction mixture, there was obtained about 0.5 µg of a DNA fragment of about 1.7 kb (PstI-BamHI fragment) containing the lipoprotein terminator by the LGT method.

Further, separately, 3 µg of pKYP10 prepared by the procedure described in Japanese Patent Application (OPI) No. 110600/83 was dissolved in 60 µl of Y-100 buffer, 6 units each of the restriction enzymes BanIII and PstI were added, and the cleavage reaction was conducted at 37° C. for 3 hours. From this reaction mixture, there was obtained, by the LGT method, about 0.5 µg of a Ptrp-containing DNA fragment of about 1.1 kb (BanIII-PstI fragment.

In view of the necessity of substituting the N-terminal amino acid Thr of mature hG-CSF with Ser and the third amino acid Leu of Mature hG-CSF with one of Gly, Ser, Cys and Arg and providing the initiation codon (ATG) required for expression and also in view of the necessity of adjusting the distance between the SD sequence and ATG downstream from Ptrp and appropriate length of 6–18 bp and for other reasons, the following DNA linker was synthesized: In the above formula, N is one of the bases G, A, T and C.

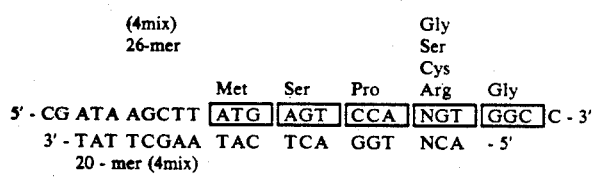

First, the 26-mer and 20-mer single-strand DNAs were synthesized by the ordinary phosphotriester method. The 26-mer and 20-mer (each 20 picomoles) were dissolved in 40 μl of T4 kinase buffer, 6 units of T4 polynucleotide kinase was added, and the phosphorylation reaction was carried out at 37° C. for 60 minutes.

Then, 0.3 μg of the pCSF1-2-derived ApaI-BamHI fragment (about 1.5 kb), 0.2 μg of the pGEL1-derived PstI-BamHI fragment (about 1.7 kb) and 0.2 μg of the BanIII-PstI fragment (about 1.1 kb) of the expression vector pKYP10, each obtained in the above manner, were dissolved in 30 μl of T4 ligase buffer, and about 1 picomole of the above DNA linker was added to the mixture solution. After further addition of 6 units of T4 DNA ligase to the solution, the ligation reaction was carried out at 4° C. for 18 hours.

The recombinant plasmid-containing reaction mixture was used to transform E. coli C600SF8 (FERM BP-1070) by the method of Cohen et al. and Ap$^r$ colonies were obtained. The plasmid DNAs were separated and purified from these transformants by known methods. The structure of each of said plasmid DNAs was confirmed by cleavage with PstI, EcoRI and BanIII, followed by polyacrylamide gel electrophoresis. The plasmids obtained in the above manner are called pCfTM14, pCfTM17 and pCfTM113, as shown in FIG. 4. The sequences in the vicinity of the N terminus of the hG-CSF derivative-encoding genes were confirmed by the dideoxy sequencing method using M13 phage to be as follows:

| pCfTM14 | Met Ser Pro Cys Gly Pro Ala |
| | ATG AGT CCA TGT GGC CCT GCC |
| pCfTM17 | Met Ser Pro Arg Gly Pro Ala |
| | ATG AGT CCA CGT GGC CCT GCC |
| pCfTM113 | Met Ser Pro Ser Gly Pro Ala |
| | ATG AGT CCA AGT GGC CCT GCC |

The substitution of the N-terminal Thr and third amino acid Leu of mature hG-CSF by Ser and Cys, respectively was confirmed in the pCfTM14-encoded derivative, which is called hG-CSF[Ser$^1$, Cys$^3$]. Similarly, the substitution of the N-terminal Thr and third amino acid Leu by Ser and Arg, respectively was confirmed in the pCfTM17-encoded derivative, which is called hG-CSF[Ser$^1$, Arg$^3$], and the substitution of the N-terminal Thr and third amino acid Leu by Ser and Ser, respectively in the pCfTM113-encoded derivative, which is Called hG-CSF[Ser$^1$, Ser$^3$].

EXAMPLE 5

(1) Construction of the recombinant plasmid pCfWD1 (cf. FIG. 5)

In 50 μl of Y-100 buffer, there was dissolved 5 μg of pCf TA1 obtained by the procedure of Example 1, 10 units of the restriction enzyme StuI and 10 units of the restriction enzyme BanIII (Toyobo) were added, and the digestion reaction is carried out at 37° C. for 1 hour. From the reaction mixture, there was obtained about 0.5 μg of an hG-CSF cDNA-containing DNA fragment of about 1.3 kb (BanIII-StuI fragment). Separately, 3 μg of pKYP26 produced by the procedure of Reference Example 2 was dissolved in 50 μl of Y-100 buffer, 6 units of BamHI was added, and the digestion reaction was carried out at 30° C. for 1 hour.

To this was added an equal volume of phenol saturated with 10 mM Tirs-HCl (pH 7.5) and 1 mM EDTA. After vigorous stirring, the aqueous layer was collected by low-speed centrifugation (3,300 rpm, 10 minutes; hereinafter, the same conditions were used). An equal volume of chloroform was added and, after vigorous stirring, the aqueous layer was collected by low-speed centrifugation. A 1/10 volume of 3 M sodium acetate was added, 2.5 volumes of ethanol was then added, and the mixture was allowed to stand at −20° C. for 1 hour. The 11,000 rpm, 10 minutes). This precipitate was dissolved in 30 μl of Klenow buffer, dATP, dTTP, dCTP and dGTP were added each to a concentration of 100 μM, 2 units of DNA polymerase I Klenow fragment was added, and the reaction was carried out at 17° C. for 15 minutes. The DNA polymerase I Klenow fragment was inactivated by treating at 68° C. for 10 minutes, thereafter NaCl was added to a concentration of 100 mM, 5 units of the restriction enzyme PstI was added, and the digestion reaction was carried out at 37° C. for 1 hour. From the reaction mixture, there was obtained, by the LGT method, about 0.6 μg of an lpp terminator-containing DNA fragment of about 1.8 kb [BamHI (blunt)-PstI fragment]. Separately, 4 μg of pGEL1 was dissolved in 40 μl of Y-100 buffer, 10 units each of the restriction enzymes BanIII (Toyobo) and PstI were added, and the digestion reaction was conducted at 37° C. for 1 hour, and 0.4 μg of tryptophan promoter-containing DNA fragment of about 1 kb (BanIII-PstI fragment) was obtained from the reaction mixture by the LGT method.

About 0.2 μg of the pCfTA1-derived BanIII-StuI fragment (about 1.3 kb), about 0.1 μg of the pKYP26-derived BamHI(blunt)-PstI fragment (about 1.8 kb) and about 0.1 μg of the pGEL1-derived BanIII-PstI fragment (about 1 kb) were dissolved in 30 μl of T4 DNA ligase ligation reaction was performed at 4° C. for 18 hours.

The reaction mixture was used to transform E. coli HB101 and an Ap$^r$ colony was obtained, and the plasmid DNA was recovered from this colony by the above-mentioned method of Birnboim et al. Thus was obtained pCfWD1 shown in FIG. 5.

(2) Construction of pCfT95K19 (cf. FIG. 6)

In 50 μl of Y 100 buffer, there was dissolved 5 μg of the pCfTL38 obtained by the procedure of Example 3, 10 units each of the restriction enzymes HindIII and BglIII were added, and the digestion reaction was carried out at 37° C. for 1 hour. About 0.7 μg of a tryptophan promoter-containing DNA fragment of about 2.6 kb (HindIII-BalII fragment) was obtained from the reaction mixture by the LGT method. Separately, 100 µg of pCfTL38 was dissolved in 1.5 ml of Y-100 buffer, 80 units each of the restriction enzymes BamHI and HindIII were added, and the digestion reaction was conducted at 37° C. for 6 hours. An hG-CSF cDNA-containing DNA fragment was recovered from the reaction mixture by the LGT method and purified using ELUTIP ™ -d (Schleicher & Schuell). This DNA fragment was dissolved in a total volume of 90 µl of a solution containing 10 mM Tris-HCl (pH 7.5), 7 mM MgCl₂, 150 mM NaCl and 6 mM 2-mercaptoethanol (hereinafter referred to as "Y-150 buffer"), 3 units of the restriction enzyme DpnI (Boehringer Mannheim) was added, and the digestion reaction was carried out at 37° C. for 15 minutes. About 1 µg of an hG-CSF cDNA-containing DNA fragment of about 300 bp (HindIII-DpnI fragment) was obtained from the reaction mixture by polyacrylamide gel electrophoresis.

Separately, 10 µg of pCfTB20 obtained by the procedure of Example 2 was dissolved in 100 µl of Y-100 buffer, 10 units of the restriction enzyme AvaI was added, and the digestion reaction was performed at 37° C. for 1 hour. The DNA recovered from the digest by phenol-chloroform extraction and ethanol precipitation was dissolved in 30 µl of Klenow buffer, 2 units of DNA polymerase I Klenow fragment was added, and the reaction was carried out at 17° C. for 30 minutes. The DNA polymerase I Klenow fragment was inactivated by treating at 68° C. for 10 minutes, NaCl was added to 100 mM, 10 units of the restriction enzyme BglII was added, an the digestion reaction was conducted at 37° C. for 1 hour. About 0.3 µg of an lpp terminator portion-containing DNA fragment of about 480 bp [AvaI(blunt)-BglII fragment] was obtained from the reaction mixture by the LGT method.

In 30 µl of T4 DNA ligase buffer, there were dissolved about 0.1 µg of the pCfTL38-derived HindIII-BglII fragment (about 2.6 kb), about 0.2 µg of the pCfTL38-derived HindIII-DpnI fragment (about 300 bp) and about 0.15 µg of the pCfTB20-derived AvaI(blunt)-BglII fragment (about 480 bp), each obtained in the above manner, and, after addition of 4 units of T4 DNA ligase, the ligation reaction was carried out at 4° C. for 18 hours. The reaction mixture was used to transform E. coli HB101 and an Ap' colony was obtained. From this colony, there was recovered the plasmid DNA by the above-mentioned method of Birnboim et al. Thus was obtained pCfT95K19 shown in FIG. 6.

(3) Construction of pCfAA1 (cf. FIG. 6)

In 50 µl of Y-100 buffer was dissolved 5 µg of pCfT95K19 obtained as described in the preceding section. Thereto were added 7 units of the restriction enzyme BanIII (Toyobo) and 2 units of BglI (Nippon Gene), and the digestion reaction was conducted at 37° C. for 1 hour. From the reaction mixture, there were obtained, by the LGT method, about 0.6 µg of trypto-phan promoter portion-containing DNA fragment of about 1 kb ( BanIII-BglI fragment) and about 1 µg of an lpp terminator portion-containing DNA fragment of about 1.8 kb (BglI-BglI fragment).

Separately, 15 µg of pCfT95K19 was dissolved in 150 µl of Y-100 buffer, 6 units of the restriction enzyme BglI (Nippon Gene) and 10 units of Sau3A were added, and the digestion reaction was carried out at 37° C. for 1 hour. Polyacrylamide gel electrophoresis of the reaction mixture gave about 0.3 µg of an hG-CSF cDNA portion-containing DNA fragment of about 350 bp (BglI-Sau3A fragment).

Further, separately, the following DNA linker was synthesized:

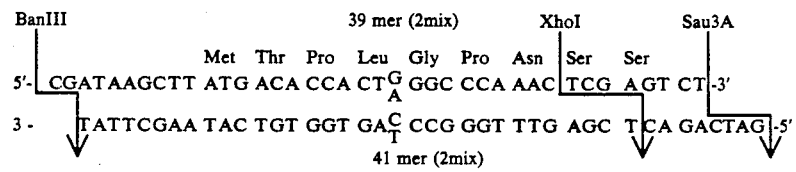

First, the 39-mer and 41-mer single-strand DNAs were synthesized by the ordinary phosphotriester method. The 39-mer and 41-mer (each 20 picomoles) were dissolved in a total volume of 40 µl of T4 DNA kinase buffer, 6 units of T4 polynucleotide kinase (Takara Shuzo) was added, and the phosphorylation reaction was carried out at 37° C. for 60 minutes.

Then, 0.1 µg of the pCfT95K19-derived BanIII-BglI fragment (about 1 kb), 0.05 µg of the BglI-BglI fragment (about 1.8 kb) and 0.1 µg of the BglI-Sau3A fragment (about 350 bp), each obtained in the above manner, were dissolved in 25 µl of T4 DNA ligase buffer, followed by addition of about 2 picomoles of the above DNA linker. After further addition of 6 units of T4 DNA ligase, the ligation reaction was conducted at 4° C. for 18 hours.

The reaction mixture was used to transform E. coli HB101, an Ap' colony was obtained, and the plasmid DNA was recovered from this colony by the above mentioned method of Birnboim et al. Thus was obtained pCfAA1 shown in FIG. 6. Determination of the base sequence of the linker portion of pCfAA1 by the above-mentioned dideoxy sequencing method revealed that the third base of the codon coding for the fourth amino acid Leu is A. In this the DNA portion coding for the 14 amino acids from the 10th amino acid Pro to the 23rd amino acid Lys of hG-CSF is missing. Furthermore, such mutation has been introduced as to change the 6th amino acid of hG-CSF from Ala to Asn, and there is now a new XhoI site.

(4) Construction of pCfAB5 (cf. FIG. 6)

In 30 µl of Y-100 buffer was dissolved 3 µg of pCfAA1 obtained as described in the previous section, 5 units of the restriction enzyme XhoI was added, and the digestion reaction was carried out at 37° C. for 1 hour. After confirmation of complete XhoI cleavage by agarose gel electrophoresis, 1 unit of the restriction enzyme BglI (Nippon Gene) was added, and partial digestion was effected at 37° C. for 25 minutes. From the reaction mixture, there was obtained, by the LGT method, about 1 µg of a tryptophan promoter portion- and lpp terminator portion-containing DNA fragment of about 3 kb (XhoI-BglI fragment). Separately, the following DNA linker was synthesized:

```
XhoI
    Ser Ser Leu Pro Gln Ser Phe Leu
    TCG AGT CTA CCA CAG AGC TTC CT      23 mer
       CA GAT GGT GTC TCG AAG GAAAATTT  25 mer
```

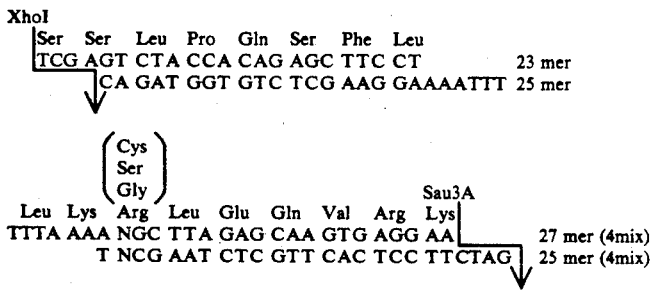

```
           ⎛ Cys ⎞
           ⎜ Ser ⎟
           ⎝ Gly ⎠                    Sau3A
Leu Lys  Arg  Leu Glu Gln Val Arg Lys
TTTA AAA NGC TTA GAG CAA GTG AGG AA        27 mer (4mix)
       T NCG AAT CTC GTT CAC TCC TTCTAG    25 mer (4mix)
```

(N being G, A, T or C).

This linker DNA contains that DNA portion which codes for the 14 amino acids of hG-CSF from the 10th amino acid Pro to the 23rd amino acid Lys. Such portion is missing in the hG-CSF cDNA of pCfAA1.

First, the 27-mer, 25-mer (two kinds) and 23-mer single-strand DNAs were synthesized by the ordinary phosphotriester method. The 27-mer and 25-mer DNAs complementary to each other and the 25-mer and 23-mer DNAs complementary to each other were dissolved in pairs, and each in an amount of 20 picomoles, in a total volume of 40 µl of T4 kinase buffer; 6 units of T4 polynucleotide kinase (Takara Shuzo) was added to each solution, and the phosphorylation reaction was performed at 37° C. for 60 minutes.

Then, 0.1 µg of the pCfAA1-derived XhoI-BglI fragment (about 3 kb) obtained as described above and 0.1 µg of the pCfT95K19-derived BglI-Sau3A fragment (about 350 bp) obtained as described in the previous section were dissolved in 30 µl of T4 DNA ligase buffer, and 2 picomoles each of the above DNA linker portions were added to the mixture solution. Further, 6 units of T4 DNA ligase was added, and the ligation reaction was conducted at 4° C. for 18 hours.

The reaction mixture was used to transform *E. coli* HB101 and Ap' colonies were obtained. From these colonies, the plasmid DNAs were recovered by the above-mentioned method of Birnboim et al. There were thus obtained pCfAB5 and pCfAB14 shown in FIG. 6. Determination of the base sequence of the DNA linker moiety of pCfAB5 and of pCfAB14 by the above-mentioned dideoxy sequencing method revealed that the first base of the codon coding for the 17th amino acid is A in pCfAB5 and T in pCfAB14, hence said codon in for Ser (AGC) in the former and for Cys (TGC) in the latter, leading to substitution of Ser for the 17th amino acid Cys of mature hG CSF in pCFAB5, but no substitution in pCfAB14.

EXAMPLE 6

(1) Construction of pCfBA8 and pCfBA32 (cf. FIG. 7)

In 40 µl of Y 100 buffer was dissolved 3 µg of pCfAB5 obtained as described in the previous section, 5 units each of the restriction enzymes AvaI and BglII were added, and the digestion reaction was conducted at 37° C. for 1 hour. From the reaction mixture, there was obtained, by the LGT method, about 1 µg of a tryptophan promoter portion- and lpp terminator portion containing DNA fragment of about 2.8 kb (AvaI-BglII fragment).

Separately, 6 µg of pCfWD1 obtained as described in section 1 was dissolved in 50 µl of Y-100 buffer, 5 units of the restriction enzyme BglII was added, and the digestion reaction was carried out at 37° C. for 1 hour. Agarose gel electrophoresis confirmed that the cleavage with BglII was complete. Thereafter, 3 units of the restriction enzyme AvaI was added, and partial cleavage was effected at 37° C. for 20 minutes. From the reaction mixture, there was obtained, by the LGT method, 0.4 µg of a DNA fragment (about 1.3 kb) containing most of the hg-CSF (BglII-AvaI fragment).

Then, 0.1 µg of the pCfAB5-derived AvaI-BglII fragment (about 2.8 kb) and 0.3 µg of the pCfWD1-derived BglII-AvaI fragment (about 1.3 kb), each obtained as described above, were dissolved in 25 µl of T4 DNA ligase was added, and the ligation reaction was carried out at 4° C. for 18 hours.

The reaction mixture was used to transform *E. coli* HB101 and an Ap' colony was obtained. From this colony, the plasmid DNA was recovered by the above-mentioned method of Birnboim et al. Thus was obtained pCfBA8.

The amino acid sequence of the hG-CSF derivative encoded by pCfBA8 contains Asn in place of the 6th amino acid Ala of mature hG-CSF and Ser in place of the 17th amino acid Cys thereof. Hereinafter, this derivative is referred to as hG-CSF[NA8].

On the other hand, 3 µg of pCfAB14 obtained as described in the previous section was dissolved in 40 µl of Y-100 buffer, 5 units each of the restriction enzyme AvaI and BglII were added, and the digestion reaction was performed at 37° C. for 1 hour. From the reaction mixture, there was obtained, by the LGT method, about 1 µg of a tryptophan promoter portion- and lpp terminator portion-containing DNA fragment of about 2.8 kb (AvaI-BglII fragment).

Separately, 6 µg of pCfWD1 obtained as described in section 1 was dissolved in 50 µl of Y-100 buffer, 5 units of the restriction enzyme BglII was added, and the digestion reaction was carried out at 37° C. of 1 hour. After confirmation of the completeness of the BglII cleavage by agarose gel electrophoresis, 3 units of the restriction enzyme AvaI was added, and partial cleavage was effected at 37° C. for 20 minutes. From the reaction mixture, there was obtained, by the LGT method, 0.4 µg of a DNA fragment (about 1.3 kb) containing most of the hG-CSF cDNA (BglII-AvaI fragment).

Then, 0.1 µg of the pCfAB14-derived AvaI-BglII fragment (about 2.8 kb) and 0.3 µg of the pCfWD1-derived BglII-AvaI fragment (about 1.3 kb), each obtained as described above, were dissolved in 25 µl of T4 DNA ligase buffer, 3 units of T4 DNA ligase was added, and the ligation reaction was performed at 4° C. for 18 hours.

The reaction Mixture was used to transform E. coli HB101 and an Ap[r] colony was obtained and, from this colony, the plasmid DNA was recovered by the above-mentioned method of Birnboim et al. Thus was obtained pCfBA32 shown in FIG. 7.

The amino acid sequence of the hG-CSF derivative encoded by pCfBA32 contains Asn in lieu of the 6th amino acid Ala of mature hG-CSF.

(2) Construction of pCfBB101

In 50 μl of Y-100 buffer was dissolved 6 μg of pCfBA8 obtained as described in the previous section, 10 units of the restriction enzyme BanIII (Toyobo), 8 units of BglII and 8 units of XhoI were added, and the digestion reaction was conducted at 37° C. for 1 hour. From the reaction mixture, there were obtained, by the LGT method, about 0.6 μg of an hG-CSF cDNA-containing DNA fragment of about 1.4 kb (XhoI-BglII fragment) and about 0.8 μg of a tryptophan promoter portion-containing DNA fragment of about 2.7 kb (BanIII-BglII fragment).

Separately, the following DNA linker was synthesized:

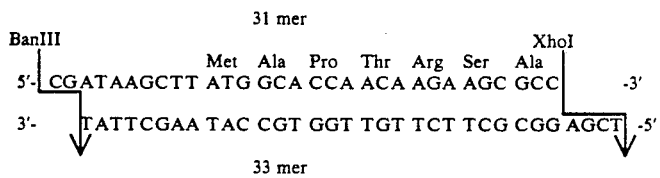

First, the 31-mer and 33-mer single-strand DNAs were synthesized by the ordinary phosphotriester method. The 31-mer and 33-mer (each 2 μg) were dissolved in a total of 40 μl of T4 kinase buffer, 30 units of T4 polynucleotide kinase (Takara Shuzo) was added, and the phosphorylation reaction was conducted at 37° C. for 60 minutes.

Then, 0.1 μg of the pCfBA8-derived BanIII-BglII fragment (about 2.7 kb fragment) and 0.1 μg of the pCfBA8-derived XhoI-BglII fragment (about 1.4 kb fragment), each - obtained as described above, were dissolved in 25 μl of T4 DNA ligase buffer, and about 2 picomoles of the above DNA linker was added to the mixture solution. After further addition of 6 units of T4 DNA ligase, the ligation reaction was carried out at 4° C. for 18 hours.

The recombinant plasmid mixture thus obtained was used to transform E. Coli HB101 and an Ap[r] colony was obtained. From cultured cells derived from this colony, there was recovered the plasmid DNA. Thus was obtained pCfBB101 shown in FIG. 7. The amino acid sequence of the hG-CSF derivative encoded by pCfBB101 contains Ala, Thr, Arg, Ser and Ser in lieu of the first amino acid Thr, third amino acid Leu, fourth amino acid Gly, fifth amino acid Pro and 17th amino acid Cys of mature hG-CSF, respectively. Hereinafter, this derivative is referred to as hG-CSF[NB101].

(3) Construction of pCfBC42B1, pCfBC45, pCfBC52, pCfBC59, pCfBC76, pCfBC77, pCfBC93, pCfBC95 and pCfBC97 (Cf. FIG. 8)

First, the following DNA linker was synthesized:

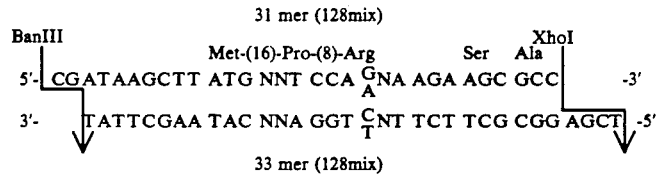

(N being one of G, A, T and C).

In this synthetic DNA linker, the three bases each represented by N are each independently one of G, A, T and C and one base is G or A (in the case of 31-mer) or C or T (in the case of 33-mer) and therefore this linker is obtained as a mixture of a total of 128 DNA linkers. As a result, the design of this linker is such that, in the N-terminal hG-CSF amino acid sequence encoded by this linker, 16 different amino acids are possible as the amino acid next to Met and 8 different amino acids are possible as the amino acid next to Pro, hence 128 amino acid sequences in total are possible.

First, the 31-mer and 33-mer single-strand DNAs were synthesized by the ordinary phosphotriester method. The 31-mer and 33-mer (each 2 μg) were dissolved in a total volume of 40 μl of T4 kinase buffer, 30 units of T4 polynucleotide kinase (Takara Shuzo) was added, and the phosphorylation reaction was conducted at 37° C. for 60 minutes.

Then, 0.1 μg of the pCfBA8-derived BanIII-BglII fragment (about 2.7 kb fragment) and 0.1 μg of the pCfBA8-derived XhoI-BglII fragment (about 1.4 kb fragment), each obtained in Example 6, were dissolved in 25 μl of T4 DNA ligase buffer, and about 2 picomoles of the above DNA linker was added to the mixture solution. After further addition of 6 units of T4 DNA ligase, the ligation reaction was carried out at 4° C. for 18 hours.

The recombinant plasmid mixture thus obtained was used to transform E. coli HB101 and Ap[r] colonies were obtained. From cultured cells of these colonies, the plasmid DNAs were recovered. Thus were obtained pCfBC42B1, pCfBC45, pCfBC52, pCfBC59, pCfBC76, pCfBC77, pCfBC93, pCfBC95 and pCfBC97. Determination of the base sequence in each DNA linker moiety by the above-mentioned dideoxy sequencing method revealed that the base sequences on the N-terminal side of hG-CSF derivatives are as follows:

| pCfBC42B1 | Met Thr Pro Glu Lys Ser Ala |
| | ATG ACT CCA GAA AAA AGC GCC |
| pCfBC45 | Met Val Pro Ile Arg Ser Ala |

-continued

| | | |
|---|---|---|
| pCfBC52 | Met Cys Pro Ile Arg Ser Ala | ATG GTT CCA ATA AGA AGC GCC |
| | | ATG TGT CCA ATA AGA AGC GCC |
| pCfBC59 | Met Tyr Pro Ile Arg Ser Ala | ATG TAT CCA ATA AGA AGC GCC |
| pCfBC76 | Met Arg Pro Thr Arg Ser Ala | ATG CGT CCA ACA AGA AGC GCC |
| pCfBC77 | Met Thr Pro Thr Arg Ser Ala | ATG ACT CCA ACA AGA AGC GCC |
| pCfBC93 | Met Asn Pro Glu Arg Ser Ala | ATG AAT CCA GAA AGA AGC GCC |
| pCfBC95 | Met Ile Pro Thr Arg Ser Ala | ATG ATT CCA ACA AGA AGC GCC |
| pCfBC97 | Met Ser Pro Thr Arg Ser Ala | ATG AGT CCA ACA AGA AGC GCC |

The substituent amino acid residues in the hG-CSF derivatives encoded by these plasmids as respectively compared with mature hG-CSF are as follows:

| | Position of amino acid substitution (amino acid of hG-CSF) | | | | |
|---|---|---|---|---|---|
| Plasmid | 1st (Thr) | 3rd (Leu) | 4th (Gly) | 5th (Pro) | 17th (Cys) |
| pCfBC42B1 | —* | Glu | Lys | Ser | Ser |
| pCfBC45 | Val | Ile | Arg | Ser | Ser |
| pCfBC52 | Cys | Ile | Arg | Ser | Ser |
| pCfBC59 | Tyr | Ile | Arg | Ser | Ser |
| pCfBC76 | Arg | Thr | Arg | Ser | Ser |
| pCfBC77 | —* | Thr | Arg | Ser | Ser |
| pCfBC93 | Asn | Glu | Arg | Ser | Ser |
| pCfBC95 | Ile | Thr | Arg | Ser | Ser |
| pCfBC97 | Ser | Thr | Arg | Ser | Ser |

*No substitution

The hG-CSF derivatives encoded by pCfBC42B1, pCfBC45, pCfBC52, pCfBC59, pCfBC76, pCfBC77, pCfBC93, pCfBC95 and pCfBC97 are hereinafter referred to as hG-CSF[NC42B1], hG-CSF[NC45], hG-CSF[NC52], hG-CSF[NC59], hG-CSF[NC76], hG-CSF[NC77], hG-CSF[NC93], hG-CSF[NC95] and hG-CSF[NC97], respectively.

(4) Construction of pCfBD28, pCfBDD56 and pCfBD82

First, the following DNA linker was synthesized:

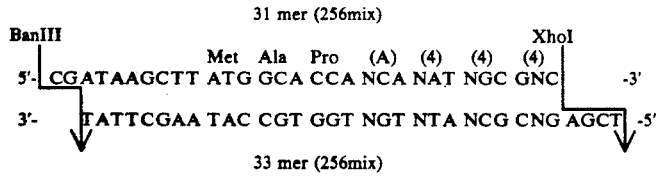

(N being one of G, A, T and C)

In this DNA linker, the four bases represented by N are each independently G, A, T or C and, accordingly, the linker is obtained as a mixture of a total of 256 different DNA linkers. As a result, the design of this DNA linker is such that, in the N-terminal hG-CSF amino acid sequence encoded by the DNA linker, four amino acids are possible in each of the four positions in question, hence totally 256 different amino acid sequences are possible.

First the 31-mer and 33-mer single-strand DNAs were synthesized by the ordinary phosphotriester method. In a total of 40 μl of T4 kinase buffer, there were dissolved 2 μg each of the 31-mer and 33-mer, 30 units of T4 polynucleotide kinase (Takara Shuzo) was added, and phosphorylation reaction was performed at 37° C. for 60 minutes.

Then, 0.1 μg of the pCfBA8-derived BanIII-BglII fragment (about 2.7 kb fragment) and 0.1 μg of the pCfBA8-derived XhoI-BglII fragment (about 1.4 kb fragment), each obtained in Example 6, were dissolved in 25 μl of T4 DNA ligase buffer, and about 2 picomoles of the above DNA linker was added to the mixture solution. After further addition of 6 units of T4 DNA ligase, the ligation reaction was conducted at 4° C. for 18 hours.

The recombinant plasmid mixture obtained was used to transform E. coli HB101, and Ap' colonies were obtained. From cultured cells of these colonies, the plasmids were respectively recovered. Thus were obtained pCfBD28, pCfBD56 and pCfBD82. Determination of the base sequence in the DNA linker moiety by the above-mentioned dideoxy sequencing method revealed that the base sequences on the N-terminal side of the hG-CSF derivatives are as follows:

| | | |
|---|---|---|
| pCfBD28 | Met Ala Pro Thr Tyr Arg Ala | ATG GCA CCA ACA TAT CGC GCC |
| pCfBD56 | Met Ala Pro Ser Asn Ser Ala | ATG GCA CCA TCA AAT AGC GCC |
| pCfBD82 | Met Ala Pro Pro Asn Arg Gly | ATG GCA CCA CCA AAT CGC GGC |

The replacing amino acid residues in the hG-CSF derivatives encoded by these plasmids as compared with mature hG-CSF are as follows;

| Position of amino acid substitution (amino acid of hG-CSF) | Plasmid | | |
|---|---|---|---|
| | pCfBD28 | pCfBD56 | pCfBD82 |
| 1st (Thr) | Ala | Ala | Ala |
| 3rd (Leu) | Thr | Ser | Pro |
| 4th (Gly) | Tyr | Asn | Asn |
| 5th (Pro) | Arg | Ser | Arg |
| 6th (Ala) | —* | —* | Gly |
| 17th (Cys) | Ser | Ser | Ser |

*No substitution.

The hG-CSF derivatives encoded by pCfBD28, pCfBD56, and pCfBD82 are hereinafter referred to as hG-CSF[ND28], hG-CSF[ND56] and hG-CSF[ND82], respectively. An E. coli strain harboring pCfBD56, E. coli ECfBD56, and an E. coli strain harboring pCfBD28, E. coli ECfBD28, have been deposited at the Fermentation Research Institute under the deposit numbers FERM BP-1221 and FERM BP-1479, respectively in accordance with the Budapest treaty.

(5) Construction of pCfTNS7 (cf FIG. 14)

The following DNA linker was synthesized.

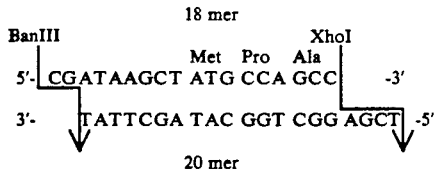

According to the design of this DNA linker, the four amino acids from the 1st amino acid Thr to the 4th amino acid Gly of the N-terminal amino acid sequence of hG-CSF are missing in the N-terminal amino acid sequence encoded by the linker.

First, the 18-mer and 20-mer single-strand DNAs were synthesized by the ordinary phosphotriester method. The 18-mer and 20-mer (each 2 μg) were dissolved in a total of 40 μl of T4 kinase buffer, 30 units of T4 polynucleotide kinase (Takara Shuzo) was added, and the phosphorylation reaction was performed at 37° C. for 60 minutes.

Then, 0.1 μg of the pCfBA8-derived BanIII-BglII fragment (about 2.7 kb fragment) and 0.1 μg of the pCfBA8-derived XhoI-BglII fragment (about 1.4 kb), each obtained in Example 6, were dissolved in 25 μl of T4 DNA ligase buffer, about 2 picomoles of the above DNA linker was added to the mixture solution, and the ligation reaction was conducted at 4° C. for 18 hours.

The recombinant plasmid mixture thus obtained was used to transform E. coli HB101, and an Ap$^r$ colony was obtained. From cultured cells of this colony, there was recovered the plasmid. Thus was obtained pCfTNS7. The hG-CSF derivative encoded by pCfTNS7 is hereinafter referred to as hG-CSF[Δ1-4S].

(6) Construction of pCfTAArg4S (cf. FIG. 14)

The following DNA linker was synthesized:

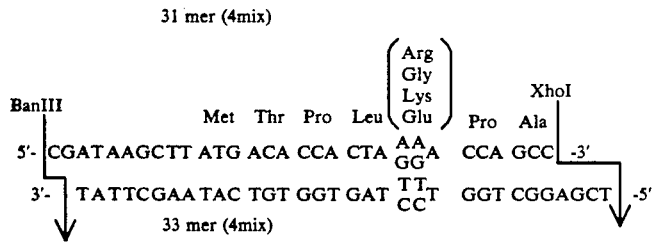

In this DNA linker, two bases each independently is A or G, hence said linker is obtained as a mixture of a total of four DNA linkers. Accordingly, the design of this DNA linker is such that four amino acids are possible as the 4th amino acids in the N-terminal hG-CSF amino acid sequence encoded by said linker.

First, the 31-mer and 33-mer single-strand DNAs were synthesized by the ordinary phosphotriester method. The 31-mer and 33-mer (each 2 μg) were dissolved in a total volume of 40 μl of T4 kinase buffer, 30 units of T4 polynucleotide kinase (Takara Shuzo) was added, and the phosphorylation reaction was carried out at 37° C. for 60 minutes.

Then, 0.1 μg of the pCfBA8-derived BanIII-BglII fragment (about 2.7 kb fragment) and 0.1 μg of the pCfBA8-derived XhoI-BglII fragment (about 1.4 kb fragment), each obtained as described in section (1), were dissolved in 25 μl of T4 DNA ligase buffer, and about 2 picomoles of the above DNA linker was added to the mixture solution. After further addition of 6 units of T4 DNA ligase, the ligation reaction was performed at 4° C. for 18 hours.

The recombinant plasmid mixture thus obtained was used to transform E. coli HB101, and an Ap$^r$ colony was obtained. From cultured cells of this colony, there was recovered the plasmid. Thus was obtained pCfTAArg4S. Determination of the base sequence of the DNA linker moiety by the above-mentioned dideoxy sequencing method revealed that the N-terminal base sequence of the hG-CSF derivative is as follows:

| pCfTAArg4S | Met Thr Pro Leu Arg Pro Ala |
|---|---|
|  | ATG ACA CCA CTA AGA CCA GCC |

The hG-CSF derivative encoded by pCfTAArg4S is hereinafter referred to as hG-CSF[Arg$^4$,Ser$^{17}$].

(7) Construction of pCfTN205 (cf. FIG. 15)

In 40 μl of K-150 buffer (same as Y-100 buffer except for replacement of 150 mM KCl for 100 mM NaCl), there was 3 μg of pCfTNS7 obtained in section 5, 5 units each of the restriction enzymes PvuI and XhoI, and the digestion reaction was conducted at 37° C. for 1 hour. From the reaction mixture, there was obtained, by the LGT method, about 0.5 μg of a tryptophan promoter portion-containing DNA fragment of about 1.0 kb (PvuI-XhoI fragment).

Separately, 3 μg of pCfBA32 obtained in section 1 was dissolved in 40 μl of K-150 buffer, 5 units each of the restriction enzymes PvuI and XhoI were added, and the digestion reaction was carried out at 37° C. for 1 hour. From the reaction mixture, there was obtained, by the LGT method, 2 μg of an about 3.0 kb DNA fragment (XhoI-PvuI fragment) containing most of the hG-CSF cDNA.

Then, 0.1 μg of the pCfTNS7-derived PvuI-XhoI fragment (about 1.0 kb) and 0.3 μg of the pCfBA32-derived XhoI-PvuI fragment (about 3.0 kb), each obtained in the above manner, were dissolved in 25 μl of T4 DNA ligase buffer, 3 units of T4 DNA ligase was added, and the ligation reaction was conducted at 4° C. for 18 hours.

The reaction mixture was used to transform E. coli HB101, and Ap$^r$ colony was obtained, and the plasmid DNA was recovered from this colony by the above-mentioned method of Birnboim et al. Thus was obtained pCfTB205 shown in FIG. 15.

In the amino acid sequence of the hG-CSF derivative encoded by pCfTN205, the 1st to 4th amino acids of mature hG-CSF are missing. Hereinafter, this derivative is referred to as hG-CSF[Δ1-4].

(8) Construction of pCfTAArg4 (cf. FIG. 15)

In 40 µl of K-150 buffer, there was dissolved 3 µg of pCfTAArg4S obtained in section 6, 5 units each of the restriction enzymes PvuI and XhoI were added, and the digestion reaction was performed at 37° C. for 1 hour. From the reaction mixture, there was obtained by the LGT method, about 0.5 µg of a tryptophan promoter portion-containing DNA fragment of about 1.0 kb (PvuI-XhoI fragment).

Separately, 3 µg of pCfBA32 obtained in section 1 was dissolved in 40 µl of K-150 buffer, 5 units each of the restriction enzymes PvuI and XhoI were added, and the digestion reaction was conducted at 37° C. for 1 hour. From the reaction mixture, there was obtained, by the LGT method, 2 µg of an about 3.0 kb DNA fragment (XhoI-PvuI fragment) containing most of the hG-CSF cDNA.

Then, 0.1 µg of the pCfTAArg4S-derived PvuI-XhoI fragment (about 1.0 kb) and 0.3 µg of the pCfBA32-derived XhoI-PvuI fragment (about 3.0 kb), each obtained in the above manner, were dissolved in 25 µl of T4 DNA ligase buffer, 3 units of T4 DNA ligase was added, and the ligation reaction was carried out at 4° C. for 18 hours.

The reaction mixture was used to transform *E. coli* HB101, Ap$^r$ colony was obtained, and the plasmid DNA was recovered from this colony by the abovementioned method of Birnboim et al. Thus was obtained pCfTAArg4 shown in FIG. 15.

The fourth amino acid in the amino acid sequence of the hG-CSF derivative encoded by pCfTAArg4 is Arg in lieu of Gly in mature hG-CSF. Hereinafter, this derivative is called hG-GSF[Arg4].

(9) Construction of pCfTNS301 (cf. FIG. 16)

In 50 µl of Y-100 buffer, there was dissolved 6 µg of pCfBA8 obtained in section 1, 10 units of the restriction enzyme HindIII and 8 units of BglII were added, and the digestion reaction was carried out at 37° C. for 1 hour. From the reaction mixture, there was obtained, by the LGT method, about 0.6 µg of an hG-CSF cDNA-containing DNA fragment of about 1.4 kb (HindIII-BglII fragment).

Then, the following DNA linker was synthesized:

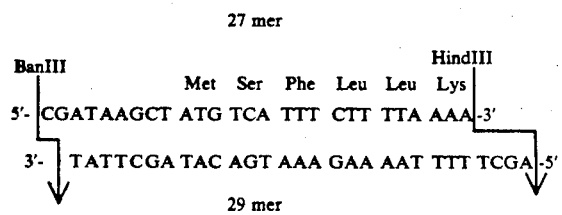

The design of this DNA linker is such that the 11 amino acids from the first amino acid Thr to the 11th amino acid Gln of hG-CSF are missing in the N-terminal amino acid sequence encoded by said linker.

First, the 27-mer and 29-mer single strand DNAs were synthesized by the ordinary phosphotriester method. The 27-mer and 29-mer (each 2 µg) were dissolved in a total of 40 µl of T4 kinase buffer, 30 units of T4 polynucleotide kinase (Takara Shuzo) was added, and the phosphorylation reaction was conducted at 37° C. for 60 minutes.

Then, 0.1 µg of the pCfBA8-derived BanIII-BglII fragment (about 2.7 kb fragment) and 0.1 µg of the pCfBA8-derived HindIII-BglII fragment (about 1.4 kb fragment), each obtained as mentioned hereinabove, were dissolved in 25 µl of T4 DNA ligase buffer, and about 2 picomoles of the above DNA linker was added to the mixture solution. After further addition of 6 units of T4 DNA ligase, the ligation reaction was carried out at 4° C. for 18 hours.

The recombinant plasmid mixture thus obtained was used to transform *E. coli* HB101, and an Ap$^r$ colony was obtained. From cultured cells of this colony, there was recovered the plasmid DNA. Thus was obtained pCfTNS301. The hG-CSF derivative encoded by pCfTNS301 is hereinafter called hG-CSF[Δ1-11S].

(10) Construction of pCfTNS401 (cf. FIG. 16)

The following DNA linker was synthesized:

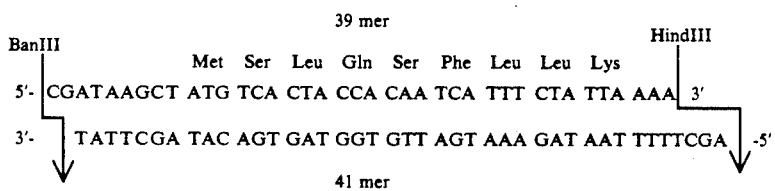

The design of this DNA linker is such that the 7 amino acids from the first amino acid Thr to the 7th amino acid Ser of hG-CSF are missing in the N-terminal amino acid sequence encoded by the linker.

First, the 39-mer and 41-mer single-strand DNAs were synthesized by the ordinary phosphotriester method. The 39-mer and 41-mer (each 2 µg) were dissolved in a total of 40 µl of T4 kinase buffer, 30 units of T4 polynucleotide kinase (Takara Shuzo) was added, and the phosphorylation reaction was performed at 37° C. for 60 minutes.

Then, 0.1 µg of the pCfBA8-derived BanIII-BglII fragment (about 2.7 kb fragment) and 0.1 µg of the pCfBA8-derived HindIII-BglII fragment (about 1.4 kb fragment), each obtained as described above, were dissolved in 25 µl of T4 DNA ligase buffer, and about 2 picomoles of the above-mentioned DNA linker was added to this mixture solution. After further addition of 6 units of T4 DNA ligase, the ligation reaction was conducted at 4° C. for 18 hours.

The recombinant plasmid mixture thus obtained was used to transform *E. coli* HB101, and Ap$^r$ colony was obtained. The plasmid DNA was recovered from this colony. Thus was obtained pCfTNS401. The hG-CSF derivative encoded by pCfTNS401 is hereinafter called hG-CSF[Δ1-7S].

(11) Construction of pCfTNS501 (cf. FIG. 12)

In 40 µl of Y-100 buffer, there was dissolved pCfBA8-obtained in section 1, 10 units of the restriction enzyme XhoI was added, and the digestion reaction was carried out at 37° C. for 1 hour. The DNA recovered by phenol-chloroform extraction and ethanol precipitation was dissolved in 30 μl of Klenow buffer, 2 units of DNA polymerase I Klenow fragment was added, and the reaction was carried out at 17° C. for 30 minutes. The DNA polymerase I Klenow fragment was inactivated by 10-minute treatment at 68° C., KCl was added to a concentration of 150 mM, 8 units of the restriction enzyme PvuI was added, and the digestion reaction was conducted at 37° C. for 1 hour. From the reaction mixture, there was obtained, by the LGT method, about 2 μg of an hG-CSF cDNA-containing DNA fragment of about 3 kb [XhoI(blunt)-PvuI].

Separately, 5 μg of the ATG vector pTrS20 (3.8 kb) obtained by the procedure of Reference Example 4 was dissolved in 50 μl of Y-0 buffer (Y-100 buffer minus 100 mM NaCl), 16 units of the restriction enzyme SacI was added, and the cleavage reaction was carried out at 37° C. for 3 hours. The DNA recovered by phenol-chloroform extraction and ethanol precipitation was dissolved in 30 μl of Klenow buffer, 2 units of DNA polymerase I Klenow fragment was added, and the reaction was conducted at 17° C. for 30 minutes. The DNA polymerase I Klenow fragment was inactivated by treatment at 68° C. for 10 minutes, KCl was added to a concentration of 150 mM, 8 units of the restriction enzyme PvuI was added, and the digestion reaction was performed at 37° C. for 1 hour. From the reaction mixture, there was obtained, by the LGT method, about 0.5 μg of a Ptrp-containing DNA fragment of about 1 kb [SacI(blunt)-PvuI].

Then, 0.1 μg of the pCfBA8-derived XhoI(blunt)-PvuI fragment (about 3 kb) and 0.2 μg of the pTrS20-derived SacI(blunt)-PvuI fragment (about 1 kb) were dissolved in 25 μl of T4 DNA ligase buffer, 3 units of T4 DNA ligase was added, and the ligation reaction was carried out at 4° C. for 18 hours.

The reaction mixture was used to transform *E. coli* HB101, an Ap$^r$ colony was obtained, and the plasmid DNA was recovered by the above-mentioned method of Birnboim et al. Thus was obtained pCfTNS501 shown in FIG. 12.

In the hG-CSF derivative encoded by pCfTNS501, the 1st to 6th N-terminal amino acids of mature hG-CSF are missing and the 17th amino acid is Ser in place of Cys. The hG-CSF derivative encoded by pCfTNS501 is hereinafter called hG-CSF(Δ1-6S].

EXAMPLE 7

(1) Construction of pCfCB101, pCfCC52, pCfCC59, pCfCF28 and pCfCD56 (cf. FIG. 8)

First, 3 μg of pBR322 [Bolivar et al.: Gene, 2, 95 (1977)] was dissolved in 40 μl of Y-100 buffer, 5 units of the restriction enzyme PstI was added, and the digestion reaction was conducted at 37° C. for 1 hour. The DNA recovered by phenol-chloroform extraction and ethanol precipitation was dissolved in 20 μl of a solution containing 33 mM Tris-acetic acid (pH 7.9), 66 mM potassium acetate, 10 mM magnesium acetate, 5 mM dithiothreitol, and dATP, dCTP, dGTP and dTTP (each 0.4 mM) (hereinafter referred to as "T4 DNA polymerase buffer"), 1 unit of T4 DNA polymerase (Takara Shuzo) was added, and the reaction was carried at 37° C. for 30 minutes. The DNA recovered by phenol-chloroform extraction and ethanol precipitation was dissolved in 20 μl of T4 DNA ligase buffer. To this was added about 8 picomoles of the BglII linker DNA [Takara Shuzo; d(pC-A-G-A-T-C-T-G)]. After further addition of 6 units of T4 DNA ligase, the ligation reaction was performed at 4° C. for 18 hours. The DNA recovered by phenol-chloroform extraction and ethanol precipitation was dissolved in 40 μl of Y-100 buffer, 10 units of the restriction enzyme EcoRI and 8 units of BglII were added, and the digestion reaction was conducted at 37° C. for 1 hour. From the reaction mixture, there was obtained, by the LGT method, about 0.9 μg of a tetracycline resistance gene portion-containing DNA fragment of about 3.6 kb (EcoRI-BglII fragment).

Separately, 3 μg of pCfBB101 obtained in Example 6-(2), pCfBC52 or pCfBC59 obtained in Example 6-(3) or pCfBD28 or pCfBD56 obtained in Example 6-(4) was dissolved in 10-fold concentrated Y-100 buffer, 5 units of the restriction enzyme EcoRI and 6 units of BglII were added, and the digestion reaction was performed at 37° C. for 1 hour. From the reaction mixture, there was obtained, by the LGT method, about 0.4 μg of an hG-CSF cDNA portion-containing DNA fragment of about 1.8 kb (EcoRI-BglII fragment) in each case.

Five tubes each containing a solution of about 0.05 μg of the pBR322-derived EcoRI-BglII fragment (about 3.6 kb) obtained as described above in 20 μl of T4 DNA ligase buffer were prepared. To the tubes were added about 0.1 μg of the pCfBB101-, pCfBB52-, pcfBC59-, pCfD28- or pCfBD56-derived EcoRI-BglII fragment (about 1.8 kb fragment) and, following further addition of 4 units of T4 DNA ligase, the ligation reaction was conducted at 4° C. for 18 hours.

The recombinant plasmid mixtures obtained were used to transform *E. coli* HB101, and Tc$^r$ colonies were obtained. From cultured cells of each of these colonies, the plasmid DNA was recovered. Thus, were obtained pCfCB101, pCfCC52, pCfCC59, pCfCD52 and pCfCD56, each shown in FIG. 8. The amino acid sequences of the hG-CSF derivatives encoded by these plasmids are identical with the amino acids of the hG-CSF derivatives encoded by pCfBB101, pCfBC52, pCfBC59, pCfBC28 and pCfBD56, respectively.

EXAMPLE 8

Production and purification of hG-CSF derivatives *E. coli* W3110 strA-derived transformants (called EcfTL23, ECfTL35, ECfTL38, ECfTL41, ECfTM14, ECfTM17, ECfTM113, ECfBB101, ECfBC42B1, ECfBC45, ECfBC52, ECfBC59, ECfBC76, ECfBC77, ECfBC93, ECfBC95, ECfBC97, ECfBD28, ECfBD56, ECfBD82, ECfTNS7, ECfTAArg4S, ECfTNS301, ECfTNS401, ECfTNS501, ECfBD28A17 and ECfBD28T17) harboring the recombinant plasmids (obtained in Examples 3, 4, 6 and 7) pCfTL23, pCfTL35, pCfTL38, pCfTL41, pCfTM14, pCfTM17, pCfTM113, pCfBB101, pCfBC42B1, pCfBC45, pCfBC52, pCfBC59, pCfBC76, pCfBC77, pCfBC93, pCfBC95, pCfBC97, pCfBD28, pCfBD56, pCfBD82, pCfTNS7, pCfAArg4S, pCfTNS301, pCfTN401, pCfTNS501, pCfBD28A17 and pCfBD28A17, respectively were each cultivated in LG medium (prepared by dissolving 10 g of Bactotryptone, 5 g of yeast extract, 5 g of NaCl and 1 g of glucose in 1 liter of water and adjusting the pH to 7.0 with NaOH) at 37° C. for 18 hours. A 5-ml portion of the culture broth was inoculated into 100 ml of MCG medium (0.6% Na$_2$HPO$_4$, 0.3% KH$_2$PO$_4$, 0.5% NaCl, 0.5% casamino acids, 1 mM MgSO$_4$, 4 μg/ml vitamin B$_1$, pH 7.2) containing 25

μg/ml tryptophan and 50 μg/ml ampicillin. After incubation at 30° C. for 4-8 hours, 10 μg/ml 3β-indoleacrylic acid (hereinafter IAA), a tryptophan inducer, was added, and incubation was continued for further 2-12 hours. Cells were harvested by subjecting the culture broth to centrifugation at 8,000 rpm for 10 minutes, and washed with 30 mM NaCl-30 mM Tris-HCl buffer (pH 7.5). The washed cells were suspended in 30 ml of the above-mentioned buffer and then disrupted by ultra-sonication at 0° C. (BRANSON SONIC POWER COMPANY'S SONIFIER DISRUPTOR 200, Output Control 2, 10 minutes). Centrifugation at 9,000 rpm for 30 minutes gave a cell residue mass. Using the method of Marston et al. [F. A. O. Marston et al.: BIO/TECHNOLOGY, 2, 800 (1984)], the hG-derivative was extracted from the cell residue mass, purified, solubilized and regenerated. The protein quantity was determined by using Nippon Bio-Rad laboratories' protein assay kit (standard assay method) {M. M. Bradford: Anal. Biochem., 72, 248 (1976)].

The G-CSF activity was determined in the following manner. Bone marrow cells were aseptically collected from the femur of male C3H/He mice of 8-12 weeks of age (Shizuoka Laboratory Animal Center) and suspended in α-MEM supplemented with 10% fetal bovine serum (FBS). Nylon wool (Wako Pure Chemical Industries; Nylon Fiber 146-04231) (0.3 g) packed in a column was impregnated with 1.5 ml of this cell suspension (about $5 \times 10^7$ cells), and the reaction was allowed to proceed in a 5% $CO_2$ incubator at 37° C. for 90 minutes. Then, α-MEM warmed to 37° C. in advance was passed through the column, and bone marrow cells unadsorbed on the nylon wool were obtained as an effluent fraction. These cells were washed once with α-MEM and adjusted to a predetermined concentration.

Then, the myelopoietic stem cell colony forming ability was determined by the method of Okabe et al. [Okabe, T. et al.: Cancer Research, 44, 4503-4506 (1986)]. Thus, 0.2 ml of the marrow cells suspension prepared as above ($2 \times 10^6$ cells/ml) was admixed with a mixture of 0.2 ml of α-MEM, 0.4 ml of FBS and 0.2 ml of each $2^2$-diluted sample. An equal volume (1.0 ml) of 0.6% agar (Difco, Agar purified #0560-01) warmed to 42° C. was admixed with the mixture, and the whole mixture was distributed in 0.5-ml portions into dishes of a 24-dish plate (Munc's Multidish #143982) ($5 \times 10^4$ cells/dish, n=3). After incubation in a 5% $CO_2$ incubator at 37° C. for 7 days, colonies each comprising not less than 40 cells were counted under a microscope (Olympus X40). After colony counting, cells were taken out onto a slide glass with care and fixed with an acetone formalin mixed solution for 30 seconds. After esterase double stain of the cells by the method of Kubota et al. [Kubota, K. et al.: Exp. Hematology, 8, 339-344 (1980)], each colony was identified.

The potency of each sample was calculated on the basis of the result of counting for the 2-fold dilution in the colony formation assay, as follows. The activity which gives half of the maximum colony formation value for intact G-CSF used as the standard was defined as 50 units. The potency (in units) was calculated by multiplying by 20, inclusive of the dilution factor for each sample, for conversion to the activity per milliliter. The specific activity was expressed in terms of potency per unit weight (mg) of protein, hence in units/mg.

The potencies of intact G-CSF and G-CSF derivatives are shown in Table 4.

TABLE 4

| Strain | Plasmid borne | Plasmid-encoded product | Specific activity (units/mg) | Specific activity ratio |
|---|---|---|---|---|
| ECfTA1 | pCfTA1 | G-CSF (intact) | $2.2 \times 10^8$ | 1.0 |
| ECfTL38 | pCfTL38 | G-CSF (Ser$^1$) | $4.0 \times 10^8$ | 1.8 |
| ECfTL41 | pCfTL41 | G-CSF (Arg$^1$) | $3.7 \times 10^8$ | 1.7 |
| ECfTL23 | pCfTL23 | G-CSF (Gly$^1$) | $3.1 \times 10^8$ | 1.4 |
| ECfTL35 | pCfTL35 | G-CSF (Cys$^1$) | $2.9 \times 10^8$ | 1.3 |
| ECfBB101 | pCfBB101 | G-CSF (NB101) | $7.9 \times 10^8$ | 3.6 |
| ECfBC42B1 | pCfBC42B1 | G-CSF (NC42B1) | $5.1 \times 10^8$ | 2.3 |
| ECfBC45 | pCfBC45 | G-CSF (NC45) | $7.0 \times 10^8$ | 3.2 |
| ECfBC52 | pCfBC52 | G-CSF (NC52) | $6.2 \times 10^8$ | 2.8 |
| ECfBC59 | pCfBC59 | G-CSF (NC59) | $5.9 \times 10^8$ | 2.7 |
| ECfBC76 | pCfBC76 | G-CSF (NC76) | $6.2 \times 10^8$ | 2.8 |
| ECfBC77 | pCfBC77 | G-CSF (NC77) | $7.7 \times 10^8$ | 3.5 |
| ECfBC93 | pCfBC93 | G-CSF (NC93) | $9.2 \times 10^8$ | 4.2 |
| ECfBC95 | pCfBC95 | G-CSF (NC95) | $9.5 \times 10^8$ | 4.3 |
| ECfBC97 | pCfBC97 | G-CSF (NC97) | $8.6 \times 10^8$ | 3.9 |
| ECfBD28 | pCfBD28 | G-CSF (ND28) | $7.9 \times 10^8$ | 3.6 |
| ECfBD56 | pCfBD56 | G-CSF (ND56) | $5.1 \times 10^8$ | 2.3 |
| ECfBD82 | pCfBD82 | G-CSF (ND82) | $4.6 \times 10^8$ | 2.1 |
| ECfTM14 | pCfTM14 | G-CSF (Ser$^1$, Cys$^3$) | $3.1 \times 10^8$ | 1.4 |
| ECfTM17 | pCfTM17 | G-CSF (Ser$^1$, Arg$^3$) | $3.7 \times 10^8$ | 1.7 |
| ECfTM113 | pCfTM113 | G-CSF (Ser$^1$, Ser$^3$) | $2.9 \times 10^8$ | 1.3 |
| ECfTNS7 | pCfTNS7 | G-CSF (Δ1-4S) | $7.7 \times 10^8$ | 3.5 |
| ECfTAArg4S | pCfTAArg4S | G-CSF (Arg$^4$, Ser$^{17}$) | $5.7 \times 10^8$ | 2.6 |
| ECfTNS301 | pCfTNS301 | G-CSF (Δ1-11S) | $3.1 \times 10^8$ | 1.4 |
| ECfTNS401 | pCfTNS401 | G-CSF (Δ1-7S) | $5.5 \times 10^8$ | 2.5 |
| ECfTNS501 | pCfTNS501 | G-CSF (Δ1-6S) | $4.4 \times 10^8$ | 2.0 |
| ECfBD28A17 | pCfBD28A17 | G-CSF (ND28A17) | $6.8 \times 10^8$ | 3.1 |
| ECfBD28T17 | pCfBD28T17 | G-CSF (ND28T17) | $5.9 \times 10^8$ | 2.7 |
| ECfTN205 | pCfTN205 | G-CSF (Δ1-4) | $4.2 \times 10^8$ | 1.9 |

EXAMPLE 9

Measurement of activation of hG-CSF derivatives against human bone marrow cells

The marrow fluid was collected from the iliac bone of normal humans of 20-30 years age. An equal volume of α-MEM was added to and mixed with the marrow fluid. A 4-ml of the above bone marrow fluid was layered onto 3 ml of Ficoll-Paque solution (Pharmacia Fine Chemicals, specific gravity 1.077) and, after centrifugation at 400×g for 30 minutes, the cells occurring in the intermediate layer were separated. The cells were washed twice with PBS (prepared by dissolving 8 g of NaCl, 0.2 g of KCl, 1.15 g of $Na_2HPO_4$ and 0.2 g of $KH_2PO_4$ in water to make 1 liter of solution) and then suspended in α-MEM supplemented with 10% of fetal bovine serum (FBS), and the cell Concentration was adjusted to at most $2 \times 10^6$ cells /ml. A 10-ml portion of the cell suspension was placed in a plastic dish (Falcon 3003) and incubated in a 5% $CO_2$ incubator at 37° C. for 90 minutes. Cells unadsorbed in the plastic dish were recovered, washed once with α-MEM and, after adjustment of the concentration to a predetermined level, subjected to human myelopoietic stem cell growth promoting activity and colony formation tests. Thus, 10% FBS-supplemented α-MEM was distributed in 100-μl portions into wells of a 96-well flat microplate (NUNC, 167008). Then, samples of the hG-CSF and hG-CSF derivatives obtained by the method of Example 8 were added in 100-μl portions into wells of the first row. After thorough mixing, 100 μl of each mixture was transferred to a well of the second row for preparing a 2-fold dilution. Doubling dilution was continued in the same manner until the 12th row (n=3). In a group, α-MEM alone was used as a negative control.

Then, 100 μl ($5 \times 10^4$ eukaryotic cells) of the bone marrow cell suspension prepared as described above was sowed into each well. Incubation was carried out in a 5% $CO_2$ incubator at 37° C. for 3 days. During the 20-hour period preceding the last 18 hours, 10 μl of 6-$^3$H-thymidine (Amersham Japan, code TRK61, 107 mci/mg) was added. Cells were recovered onto a glass filter using a cell harvester(Labo-Science), dried, and measured for the radioactivity taken up by the cells using a liquid scintillation counter (Packard, Tricarb 3320).

On the other hand, the human myelopoietic stem cell colony formation assay and colony identification were performed as described in Example 8.

For calculating the potency of each sample, the activity capable of causing formation of one colony was defined as 1 unit. Thus, the Half Max value (half of the maximum take-up value) was determined based on the dose-response curve showing linearity for the results of counting in the doubling dilution series, and the potency of each sample was calculated.

The specific activity was expressed in terms of potency per unit weight (mg) of protein, i.e., in units/mg.

The potencies of the intact hG-CSF and hG-CSF derivatives are shown in Table 5.

TABLE 5

| Strain | Plasmid borne | Plasmid-encoded product | Specific activity (units/mg) | Specific activity ratio |
|---|---|---|---|---|
| ECfTA1 | pCfTA1 | G-CSF (intact) | $2.8 \times 10^8$ | 1.0 |
| ECfBC59 | pCfBC59 | G-CSF (NC59) | $7.7 \times 10^8$ | 2.8 |
| ECfBC93 | pCfBC93 | G-CSF (NC93) | $7.0 \times 10^8$ | 2.5 |
| ECfBC95 | pCfBC95 | G-CSF (NC95) | $9.5 \times 10^8$ | 3.4 |
| ECfBD28 | pCfBD28 | G-CSF (ND28) | $10.4 \times 10^8$ | 3.7 |
| ECfTAArg4 | pCfTAArg4 | G-CSR (Arg4) | $5.3 \times 10^8$ | 1.9 |
| ECfTNS501 | pCfTNS501 | G-CSF (Δ1-6S) | $6.2 \times 10^8$ | 2.2 |

EXAMPLE 10

Production of hG-CSF derivative lacking the N-terminal 1st to 7th amino acids and having serine as the 17th amino acid (hereinafter referred to as M-7S)

To 50 ml of 10 mM Tris-HCl-100 mM NaCl solution (pH 8.0) containing the derivative (a) shown in Table 2 (132 μg/ml) as obtained by cultivating the E. coli strain (ECfBC59) carrying the recombinant plasmid pCfBC59 obtained in Example 6, followed by purification, there was added 0.7 μg of subtilisin BPN' (8.5 units/mg protein) (Sigma), and incubation was performed at 25° C. for 40 hours. After 3-fold dilution with 10 mM Tris-HCl (pH 8.0), the incubation mixture was applied to a DEAE-Toyopearl 650 m (Toyo Soda Manufacturing) columns (1.7 cm×4.4 cm) filled with 10 mM Tris-HCl (pH 8.0) at a flow rate of 10 ml/hour. Then, 20 ml of 10 mM Tris-HCl (pH 8.0) was passed through the column at a flow rate of 5 ml/hour. Thereafter, elution was conducted with a buffer system of 10 mM Tris-HCl showing a linear NaCl concentration gradient from 0 M to 0.4 M at the same flow rate (total eluent volume 50 ml). The M-7S derivative was eluted at NaCl concentrations of 100–150 mM (yield 0.7 mg, or 10%). The purity was not less than 90%.

EXAMPLE 11

Production of M-7S

To 50 ml of a 10 mM Tris-HCl-100 mM NaCl solution (pH 8.0) containing the derivative (b) shown in Table 2 (132 μg/ml) as obtained by cultivating the E. coli strain (ECfBC59) carrying the recombinant plasmid pCfBC59 obtained in Example 6, followed by purification, there was added 0.7 μg of subtilisin BPN' (8.5 units/mg protein) (Sigma), and incubation was performed at 25° C. for 14 hours. After 3-fold dilution with 10 mM Tris-HCl (pH 8.0), the incubation mixture was applied to DEAE-Toyoperal 650 M (Toyo Soda Manufacturing) column (1.7 cm×4.4 cm) filled with 10 mM Tris-HCl (pH 8.0) at a flow rate of 10 ml/hour. Then, 20 ml of 10 mM Tris-HCl (pH 8.0) was passed through the column at a flow rate of 5 ml/hour. Thereafter, elution was conducted from 0 M to 0.4 M at the same flow rate (total eluent volume 50 ml). The M-7S derivative was eluted at NaCl concentrations of 100–150 mM (yield 4.2 mg, or 63%). The purity was not less than 90%.

EXAMPLE 12

Production of M-7S

To 50 ml of a 10 mM Tris-HCl-100 mM NaCl solution (pH 8.0) containing the derivative (d) shown in Table 2 (132 μg/ml) as obtained by cultivating then E. coli strain (ECfTAArg4) carrying the recombinant plasmid pCfTAArg4 obtained in Example 6, followed by purification, there was added 0.7 μg of subtilisin BPN' (8.5 units/mg protein) (Sigma), and incubation was performed at 25° C. for 40 hours. After adjustment of the NaCl concentration to 0.5 M, the incubation mixture was applied to a Zn chelate-Sepharose (Pharmacia Fine Chemicals) column (1.7 cm×2.6 cm) filled with 10 mM Tris-HCl (pH 8.0)-0.5 M NaCl at a flow rate of 6 ml/hour. Then, 12 ml of 10 mM Tris HCl (pH 8.0)-0.5 M NaCl was passed through the column at a flow rate of 3 ml/hour. Thereafter, elution was carried out with a total volume of 30 ml of 10 mM Tris-HCl-0.5 M NaCl buffer on a linear pH gradient of from 8.0 to 6.0 at the same rate of flow. The M-7S derivative was eluted in the neighborhood of pH 7.0 (yield 0.6 mg, or 9%). The purity was not less than 90%.

EXAMPLE 13

Production of hG-CSF derivative lacking the N-terminal 1st to 6th amino acids and having serine as the 17th amino acid (hereinafter referred to as M-6S)

To 50 ml of a solution of the derivative (a) shown in 2 (132 µg/ml) in 10 mM Tris-HCl-100 mM NaCl (pH 8.0), there was added 0.7 µg of subtilisin BPN' (8.5 units/mg protein) (Sigma), and incubation was carried out at 25° C. for 2 hours. After 3-fold dilution with 10 mM Tris-HCl (pH 8.0), the incubation mixture was applied to a DEAE-Toyopearl 650M (Toyo Soda) column (1.7 cm×4.4 cm) filled with 10 mM Tris-HCl (pH 8.0) at a flow rate of 10 ml/hour. Then, 20 ml of 10 mM Tris-HCl (pH 8.0) was passed through the column at a flow rate of 5 ml/hour. Thereafter, elution was carried out with a total volume of 50 ml of a buffer system of 10 mM Tris-HCl (pH 8.0) showing a linear NaCl concentration gradient from 0 M to 0.4 M at the same rate of flow. The M-6S derivative was eluted at NaCl concentrations of 100–150 mM (yield 2.6 mg, or 40%). The purity was not less than 90%.

EXAMPLE 14

Production of M-6S

To 50 ml of a 10 mM Tris-HCl-100 mM NaCl solution (pH 8.0) containing the derivative (a) shown in Table 2 (132 µg/ml), there was added 0.7 µg of Epolozyme (4120 units/mg protein) (Kyowa Hakko Kogyo), and incubation was NaCl concentration to 0.5 M, the incubation mixture was applied to a Zn chelate-Sepharose (Pharmacia Fine Chemicals) column (1.7 cm×2.6 cm) filled with 10 mM Tris-HCl (pH 8.0)-0.5 M NaCl at a flow rate of 6 ml/hour. Then, 12 ml of 10 mM Tris-HCl (pH 8.0)-0.5 M NaCl was passed through the column at a flow rate of 3 ml/hour. Thereafter, elution was carried out with a total volume of 30 ml of 10 mM Tris-HCl-0.5 M NaCl buffer on a linear pH gradient of from 8.0 to 6.0 at the same rate of flow. The M-6S derivative was eluted in the neighborhood of pH 7.0 (yield 2.5 mg, or 38%). The purity was not less than 90%.

EXAMPLE 15

Production of M-6S

To 50 ml of a 10 mM Tris-HCl-100 mM NaCl solution (pH 8.0) containing the derivative (b) shown in Table 2 (132 µg/ml), there was added 0.7 µg of subtilisin amylosacchalyticus, and incubation was carried out at 25° C. for 20 hours. After adjustment of the NaCl concentration to 0.5 M, the incubation mixture was applied to a Zn chelate-Sepharose (Pharmacia Fine Chemicals) column (1.7 cm×2.6 cm) filled with 10 mM Tris-HCl (pH 8.0)-0.5 M NaCl at a flow rate of 6 ml/hour. Then, 12 ml of 10 mM Tris-HCl (pH 8.0)-0.5 M NaCl was passed through the column at a flow rate of 3 ml/hour. Thereafter, elution was carried out with a total volume of 30 ml of 10 mM Tris-HCl (pH 8.0)-0.5 M NaCl buffer on a linear pH gradient of from 8.0 to 6.0 at the same rate of flow. The M-6S derivative was eluted in the neighborhood of pH 7.0 (yield 2.5 mg, or 38%). The purity was not less than 90%.

EXAMPLE 16

Production of M-6S

To 50 ml of a 10 mM Tris-HCl-100 mM NaCl solution (pH 8.0) containing the derivative (d) shown in Table 2 (132 µg/ml), there was added 0.7 µg of subtilisin Carlsberg (0.034 unit/mg protein) (NOVO), and incubation was carried out at 25° C. for 20 hours. After adjustment of the NaCl concentration to 0.5 M, the incubation mixture was applied to a Zn chelate-Sepharose (Pharmacia Fine Chemicals) column (1.7 cm×2.6 cm) at a flow rate of 6 ml/hour. Then, 10 mM Tris-HCl (pH 8.0)-0.5 M NaCl was passed through the column at a flow rate of 3 ml/hour. Thereafter, elution was carried out with a total volume of 30 ml of a buffer system of 10 mM Tris-HCl-0.5 M NaCl showing a linear pH gradient of from 8.0 to 6.0 at the same rate of flow. The M-6S derivative was eluted in the neighborhood of pH 7.0 (yield 3 mg, or 45%). The purity was not less than 90%.

EXAMPLE 17

Production of M-6S

To 50 ml of a 10 mM Tris-HCl-100 mM NaCl solution (pH 8.0) containing the derivative (a) shown in Table 2 (132 µg/ml), there was added 0.7 µg of proteinase K (0.027 unit/mg protein) (Sigma), and incubation was carried out at 25° C. for 40 hours. After 3-fold dilution with 10 mM Tris-HCl (pH 8.0), the incubation mixture was applied to a DEAE-Toyopearl 650M (Toyo Soda) column (1.7 cm×4.4 cm) filled with 10 mM Tris-HCl (pH 8.0) at a flow rate of 10 ml/hour. Then, 20 ml of 10 mM Tris-HCl (pH 8.0) was passed through the column at a flow rate of 5 ml/hour. Thereafter, elution was carried out with a total volume of 50 ml of a buffer system of 10 mM Tris-HCl (pH 8.0) showing a linear NaCl concentration gradient of from 0 M to 0.4 M at the same rate of flow. The M-6S derivative was eluted at NaCl concentrations of 100-150 mM (yield 2.6 mg, or 39%). The purity was not less than 90%.

EXAMPLE 18

Production of hG-CSF derivative lacking the N-terminal 1st to 5th amino acids and having serine as the 17th amino acid (hereinafter referred to as M 5S)

To 50 ml of a 10 mM Tris-HCl-100 mM NaCl solution (pH 8.0) containing the derivative (b) shown in Table 1 (132 µg/ml), there was added 0.5 µg of trypsin (267 units/mg protein) (Sigma), and incubation was carried out at 25° C. for 10 hours. After adjustment of the NaCl concentration to 0.5 M, the incubation mixture was applied to a Zn chelate-Sepharose (Pharmacia Fine Chemicals) column (1.7 cm×2.6 cm) filled with 10 mM Tris-HCl (pH 8.0)-0.5 M NaCl at a flow rate of 6 ml/hour. Then, 12 ml of 10 mM Tris-HCl (pH 8.0)-0.5 M NaCl was passed through the column at a flow rate of 3 ml/hour. Thereafter, elution was carried out with a total volume of 30 ml of a buffer system of 10 mM Tris-HCl (pH 8.0)-0.5 M NaCl showing a linear imidazole concentration gradient of from 0 M to 0.3 M at the same rate of flow. The M-5S derivative was eluted at 0.1 M imidazole (yield 2.7 mg, or 41%). The purity was not less than 90%.

EXAMPLE 19

Production of hG-CSF derivative lacking the N-terminal 1st to 4th amino acids and having serine as the 17th amino acid (hereinafter referred to as M-4S)

To 50 ml of a 10 mM Tris-HCl-100 mM NaCl solution (pH 8.0) containing the derivative (d) shown in Table 1 (132 μg/ml), there was added 5 μg of trypsin (267 units/mg protein) (Sigma), and incubation was carried out at 25° C. for 20 hours. After adjustment of the NaCl concentration to 0.5 M, the incubation mixture was applied to a Zn chelate-Sepharose (Pharmacia Fine Chemicals) column (1.7 cm×2.6 cm) filled with 10 mM Tris-HCl (pH 8.0)-0.5 M NaCl at a flow rate of 6 ml/hour. Then, 12 ml of 10 mM Tris-HCl (pH 8.0)-0.5 M NaCl was passed through the column at a flow rate of 3 ml/hour. Thereafter, elution was carried out with a total volume of 30 ml of a buffer system of 10 mM Tris-HCl (pH 8.0)-0.5 M NaCl showing a linear imidazole concentration gradient of from 0 M to 0.3 M at the same rate of flow. The M-4S derivative was eluted at 0.1 M imidazole (yield 2.7 mg, or 41%). The purity was not less than 90%.

EXAMPLE 20

Production of M-4S

To 50 ml of a 10 mM Tris-HCl-100 mM NaCl solution (pH 8.0) containing the derivative (d) shown in Table 2 (132 μg/ml), there was added 5 μg of α-chymotrypsin (267 units/mg protein) (Sigma), and incubation was carried out at 25° C. for 20 hours. After adjustment of the NaCl concentration to 0.5 M, the incubation mixture was applied to a Zn chelate-Sepharose (Pharmacia Fine Chemicals) column (1.7 cm×2.6 cm) filled with 10 mM Tris-HCl (pH 8.0) 0.5 M NaCl at a flow rate of 6 ml/hour. Then, 12 ml of 10 mM Tris-HCl (pH 8.0)-0.5 M NaCl was passed through the column at a flow rate of 3 ml/hour. Thereafter, elution was carried out with a total of 30 ml of a buffer system of 10 mM Tris-HCl (pH 8.0)-0.5 M NaCl showing a linear imidazole concentration gradient of from 0 M to 0.3 M at the same rate of flow. The M-4S derivative was eluted at 0.1 M imidazole (yield 2.3 mg, or 35%). The purity was not less than 90%.

EXAMPLE 21

As seen in Examples 10-20 there can be obtained those hG-CSF derivatives which have serine as a substitute for the 17th amino acid and are lacking in 4 (M-4S), 5 (M-5S), 6 (M-6S) and 7 (M-7S) N-terminal amino acids. The use of recombinant DNA technology generally results in addition of methionine to the N terminus, and this is one of the disadvantageous features of recombinant products. On the contrary, the use of the enzymatic cleavage technique according to the invention is advantageous since such products can be produced without addition of methionine to the N terminus.

The derivatives obtained in this manner were assayed for G-CSF activity for comparison. The results obtained are shown in Table 6.

TABLE 6

| Activity comparison among G-CSF derivatives formed by the enzymatic cleavage technique | |
|---|---|
| hG-CSF Derivative | Relative Activity (derivative/intact) |
| Intact | 1.0 |
| M-4S | 4.0 |
| M-5S | 3.5 |
| M-6S | 3.0 |
| M-7S | 3.3 |

From the results shown in Table 6, it was found that, in the above in vitro evaluation, the derivatives lacking in 4–7 N-terminal side amino acids have a 2- to 4-fold higher activity as compared with the intact hG-CSF.

Therefore, the derivatives lacking in N-terminal side amino acids that can be produced in accordance with the present invention have no methionine added to the N terminus and are 2- to 4-fold higher in activity than the intact product.

The following examples illustrate the acquisition of reactivity (susceptibility) to cleavage by hydrolytic enzymes as a result of mutation in the N-terminal portion.

TEST EXAMPLE 1

Comparison in reactivity with subtilisin Carlsberg between intact hG-CSF and N-terminal mutants of hG-CSF The derivatives shown in Table 2 and intact hG-CSF were each incubated in the presence of $3.6 \times 10^{-4}$ units/mg G-CSF of subtilisin Carlsberg (NOVO) at 25° C. for 14 hours in the same manner as in Example 16. While the derivatives shown in Table 2 gave the M-6S derivative, the intact hG-CSF remained unreacted. Furthermore, even when this enzyme was used in a 100-fold increased amount ($3.6 \times 10^{-2}$ units/mg G-CSF), the intact product failed to produce M-6S but preferentially underwent global decomposition reactions.

TEST EXAMPLE 2

Comparison in reactivity with trypsin between intact hG-CSF and N-terminal mutants of hG-CSF The derivative (a) shown in Table 2 and intact hG-CSF were each incubated in the presence of 0.22 units/mg G-CSF of trypsin (Sigma) at 25° C. for 20 hours. While the derivative (a) shown in Table 2 gave the M-4S derivative, the intact hG-CSF remained unreacted. Furthermore, even when the enzyme was in a 100-fold increased amount (22 units/mg G-CSF), the intact hG-CSF did not give M-4S but preferentially underwent global decomposition reactions.

TEST EXAMPLE 3

Heat stability of hG-CSF derivatives

A 20-μg portion of each of the various derivatives, shown in Table 6, of the invention was dissolved in 1 ml of phosphate-buffered physiological saline (PBS) (pH 7.2) or α-MEM supplemented with 10% fetal bovine serum (FBS). Incubation was carried out at 56° C., and samples were collected at timed intervals and assayed for CSF activity by colony formation testing using mouse bone marrow cells (the above-mentioned method of Okabe et al.).

Each sample was diluted by the doubling dilution technique from 40 ng/ml to give 10 dilution levels. For each level, activity assay was performed, and the residual activity was determined by comparing the activity at a certain concentration at which good dose-response with that before heating (0 minute).

The residual activity (corresponding to thermal stability) data obtained in PBS and in 10% FBS-supplemented α-MEM are shown in Table 7(A) and Table 7(B), respectively.

TABLE 7 (A)

| Sample | Residual Activity (%) | | |
|---|---|---|---|
| | 30 min. | 60 min. | 120 min. |
| Intact G-CSF | 45.2 | 16.4 | 12.7 |
| NC93 | 98.0 | 93.3 | 90.6 |
| ND28 | 68.7 | 52.8 | 33.0 |
| Arg4 | 33.8 | 15.0 | 12.9 |
| M-7S | 84.8 | 72.0 | 57.0 |
| 1-4S | 89.7 | 72.4 | 61.6 |

TABLE 7 (B)

| Sample | Residual activity (%) | | |
|---|---|---|---|
| | 30 min. | 60 min. | 120 min. |
| Intact G-CSF | 9.1 | 6.7 | 8.9 |
| ND28 | 55.6 | 46.5 | 32.4 |
| NC59 | 45.1 | 35.6 | 24.9 |

EXAMPLE 22

Construction of pCfBD28A17 and pCfBD28T17 using site-specific mutagenesis (cf. FIG. 17)

(a) Construction of single-strand template DNA (single-strand pt19BD28N)

In 50 μl of Y-100 buffer, there was dissolved 3 μg of pCfBD28 obtained by the procedure of Example 6-(4), 10 units each of the restriction enzymes BanIII (Toyobo) and PstI were added, and the cleavage reaction was carried out at 37° C. for 2 hours. From the reaction mixture, there was obtained by the LGT method, about 0.1 μg of an about 210 bp DNA fragment (BanIII-PstI fragment) coding for the N-terminal portion of the hG-CSF derivative (ND28).

Separately, 1 μg of the M13 phage vector M13mp19RF DNA (Takara Shuzo) was dissolved in a total of 50 μl of Y-50 buffer, 10 units of the restriction enzyme AccI (Toyobo) was added, and the cleavage reaction was carried out at 37° C. for 2 hours. Thereafter, NaCl was added to an NaCl concentration of 100 mM, 10 units of the restriction enzyme PstI was added, and the cleavage reaction was conducted at 37° C. for 2 hours. From the reaction mixture, there was obtained, by the LGT method, about 0.8 μg of a DNA fragment of about 7.24 kb (AccI-PstI fragment).

In 50 μl of T4 DNA ligase buffer, there were dissolved 0.2 μg of the BanIII-PstI fragment (about 210 bp) and 0.05 μg of the AccI-PstI fragment (about 7.24 kb), each obtained as described above. T4 DNA ligase (10 units) was added to the mixture solution, and the ligation reaction was performed at 12° C. for 16 hours.

Then, the above reaction mixture was used to transfect E. coli JM105 by a known method. Thus was obtained a recombinant phage. From cultured cells of an E. coli JM105-derived transformant infected with the recombinant phage, there was recovered the recombinant M13 phage RF DNA. The structure of this RF DNA (hereinafter referred to as pt19BD28N) was confirmed by cleavage with PstI, EcoRI, AvaI and XhoI followed by polyacrylamide gel electrophoresis. Then, the single-strand pt19BD28N was recovered from the recombinant phage by a known method and used as an template.

(b) Construction of gapped duplex DNA

In 30 μl of Y-100 buffer, there was dissolved 3 μg of the M13mp19 RF DNA (Takara Shuzo), 10 units each of the restriction enzymes EcoRI and HindIII were added, and the cleavage reaction was carried out at 37° C. for 2 hours. From the reaction mixture, there was obtained, by the LGT method, about 2.5 μg of a DNA fragment of about 7.2 kb (EcoRI-HindIII fragment).

This M13mp19 RF DNA-derived EcoRI-HindIII fragment (about 7.2 kb) and 1 μg of the single-strand template DNA pt19BD28N obtained as described in the preceding section were dissolved in 27 μl of Klenow buffer, and DNA denaturation was caused by boiling at 100° C. for 6 minutes. Thereafter, the mixture was allowed to stand at 65° C. for 10 minutes, at 37° C. for 40 minutes, at 4° C. for 40 minutes and in ice for 10 minutes to cause the annealing reaction to proceed, whereby a gapped duplex DNA was formed in which the G-CSF gene portion alone in the template was single-stranded. The thus-formed gapped duplex DNA was recovered by the LGT method.

(c) Mutagenesis (construction of pt19BD28NA17 and pt19BD28NT17)

A single-stranded DNA (D-1) required for substituting Ala for the 17th amino acid (from the N terminus), namely Ser, of the hG-CSF derivative [ND28] obtained in Example 6 and a single-strand DNA (D-2) required for substituting Thr for the Ser were synthesized by the ordinary phosphotriester method. The base sequences of D-1 (33-mer) and D-2 (33-mer) are shown below:

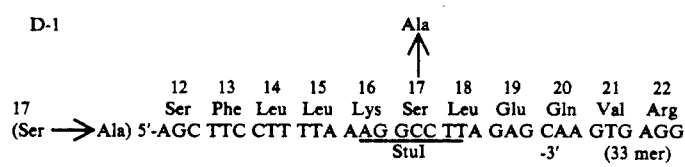

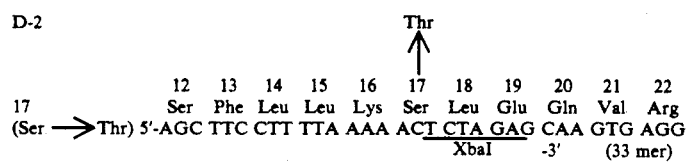

The designs of the above DNAs are such that mutagenesis using D-1 can cause formation of a new StuI site and mutagenesis using D-2 can give rise to a new XbaI site. Therefore, mutants can be identified by cleavage with these restriction enzymes.

D-1 and D-2 were each individually dissolved, in an amount of 1 μg, in 50 μl of T4 kinase buffer, 30 units of T4 polynucleotide kinase was added, and the phosphorylation reaction was carried out at 37° C. for 60 minutes.

Then, 0.2 μg of the phosphorylated D-1 or D-2 and 0.1 μg of the gapped duplex DNA obtained as described in the opening section were dissolved in 34 μl of buffer containing 6.5 mM Tris-HCl (pH 7.5), 8 mM MgCl₂, 1 mM 2-mercaptoethanol and 100 mM NaCl, the solution was allowed to stand at 65° C. for 60 minutes and then at room temperature for 30 minutes, whereby D-1 or D-2 was annealed with the gapped duplex DNA.

To the solution were added dATP, dTTP, dCTP and dGTP each to a concentration of 0.5 mM. Following further addition of 1.5 units of DNA polymerase I Klenow fragment and 10 units of T4 DNA ligase, the extension reaction was carried out at 4° C. for 16 hours.

The reaction mixture thus obtained were used to transfect *E. coli* JM105, and mutant phages were obtained. The RF DNAs were recovered from the mutant phage-infected *E. coli* JM105 transformants and identified by cleavage with AvaI, XhoI and StuI (when D-1 was used) or with XbaI (when D-2 was used), followed by polyacrylamide gel electrophoresis. The RF DNA with mutation introduced therein by means of D-1 is named pt19BD28NA17 and the RF DNA with mutation introduced therein by means of D-2 is named pt19BD28NT17. The base sequences of pt19BD28NA17 and pt19BD28NT17 in the vicinity of the StuI site and XbaI site, respectively, were confirmed by the dideoxy sequencing method using M13 phage to be as follows:

carried out at 37° C. for 2 hours. After confirmation of the completeness of the BglII cleavage by agarose gel electrophoresis, 5 units of the restriction enzyme AvaI was added, and partial cleavage was effected at 37° C. for 10 minutes. From the reaction mixture, there was obtained, by the LGT method, 0.4 μg of an about 1.29 kb DNA fragment (BglII-AvaI fragment) containing most of the mature hG-CSF cDNA with the lpp terminator portion.

Then, 0.1 μg of the pCfBD28-derived XhoI-BglII fragment (about 2.74 kb), the pCfBD28-derived BglII-AvaI fragment (about 1.29 kb) and 0.02 μg of the pt19BD28NA17-or pt19BD28NT17-derived AvaI-XhoI fragment (about 110 bp) were dissolved in 60 μl of T4 DNA ligase, 10 units of T4 DNA ligase was added, and the ligation reaction was conducted at 12° C. for 16 hours.

The reaction mixture thus obtained was used to transform *E. coli* HB101, and an Apʳ colony was obtained. The plasmid DNA was recovered from cultured cells of this colony. The plasmid constructed by using pt19BD28NA17 is named pCfBD28A17 and that constructed by using pt19BD28NT17 is named pCfBD28T17. The structure of pCfBD28A17 was confirmed by cleavage with AvaI, XhoI, BglII and StuI, followed by agarose gel electrophoresis. The structure of pCfBD28T17 was confirmed by cleavage with AvaI, XhoI, BglII and XbaI, followed by agarose gel electrophoresis.

The replacing amino acid residues in the hG-CSF derivatives encoded by these two plasmids as compared with mature hG-CSF are as follows:

pt19BD28NA17

| 12 | 13 | 14 | 15 | 16 | 17 | 18 | 19 | 20 | 21 | 22 |
|---|---|---|---|---|---|---|---|---|---|---|
| Ser | Phe | Leu | Leu | Lys | Ala | Leu | Glu | Gln | Val | Arg |
| AGC | TTC | CTT | TTA | AAG | G\|CC | TTA | GAG | CAA | GTG | AGG |

StuI pt19BD28NT17

| 12 | 13 | 14 | 15 | 16 | 17 | 18 | 19 | 20 | 21 | 22 |
|---|---|---|---|---|---|---|---|---|---|---|
| Ser | Phe | Leu | Leu | Lys | Thr | Leu | Glu | Gln | Val | Arg |
| AGC | TTC | CTT | TTA | AAA | ACT | CTA | GAG | CAA | GTG | AGG |

XbaI (d) Construction of pCfBD28A17 and pCfBD28T17

In 50 μl of Y-100 buffer, there was dissolved 3 μg of pt19BD28NA17 or pt19BD28NT17 obtained as described above, 10 units each of the restriction enzymes AvaI and XhoI were added, and the cleavage reaction was conducted at 37° C. for 2 hours. From the reaction mixture, there was obtained, by the LGT method, 0.05 μg of an about 110 bp DNA fragment containing the site of mutation introduced as described in the preceding section (AvaI-XhoI fragment).

Separately, 2 μg of pCfBD28 obtained in Example 6-(4) was dissolved in 50 μl of Y-100 buffer, 10 units each of the restriction enzymes XhoI and BglII were added, and the cleavage reaction was performed at 37° C. for 2 hours. From the reaction mixture, there was obtained, by the LGT method, about 1 μg of a tryptophan promoter portion-containing DNA fragment of about 2.74 kb (XhoI-BGlII fragment).

Further, separately, 2 μg of pCfBD28 was dissolved in 50 μl of Y-100 buffer, 10 units of the restriction enzyme BglII was added, and the cleavage reaction was

| Position of amino acid substitution | Plasmid | |
|---|---|---|
| (amino acid of hG-CSF) | pCfBD28A17 | pCfBD28T17 |
| 1st (Thr) | Ala | Ala |
| 3rd (Leu) | Thr | Thr |
| 4th (Gly) | Tyr | Tyr |
| 5th (Pro) | Arg | Arg |
| 17th (Cys) | Ala | Thr |

The hG-CSF derivatives encoded by pCfBD28A17 and pCfBD28T17 are hereinafter called hG-CSF[ND28A17] and hG-CSF[ND28T17], respectively.

REFERENCE EXAMPLE 1

Isolation of the hG-CSF cDNA-carrying plasmid pCSF1-2

(1) Preparation of poly(A) RNA from normal human peripheral blood macrophage

Macrophages, which are adherent cells, were isolated by culturing leukocytes obtained by centrifugation of normal human peripheral blood in a plastic bottle and removing nonadherent cells by washing. An RNA having poly(A) was prepared from the macrophages by the guanidine thiocyanate-lithium chloride method [Cathala et al.: DNA, 2, 329 (1983)], as follows.

Normal human peripheral blood (400 ml) was centrifuged on a Hitachi RPR10 rotor at 1,800 rpm for 20 minutes. The resultant blood cell precipitate was suspended in 50 ml of phosphate-buffered saline [8 g/liter NaCl, 0.2 g/liter KCl, 1.15 g/liter anhydrous $Na_2HPO_4$, 0.2 g/liter $KH_2PO_4$ (pH 7.2); hereinafter abbreviated as PBS]. A 25-ml portion of this suspension was layered on 25 ml of lymphocyte separation liquid (BIONETICS), and the whole was centrifuged on a Hitachi RPR10 rotor at 1,800 rpm for 30 minutes. Leukocytes in the middle layer were collected, washed with an equal volume of PBS (on a Hitachi RPR10 rotor at 1,500 rpm for 10 minutes), then suspended in 20 ml of RPMI 1640 medium (Nissui Seiyaku) containing 5% fetal bovine serum, and cultured using a tissue culture flask (Corning). After growing at 37° C. for 1.5 hours, the culture supernatant was removed together with nonadherent cells. A fresh 20-ml portion of the same medium and E. coli-derived lipopolysaccharide (LPS) (in an amount to give a concentration of 0.3 mg/ml) were added, and cultivation was continued at 37° C. for further 4 hours. Then, cells were harvested from the culture by centrifugation at 1,100×g at 4° C. for 10 minutes, washed with 80 ml of PBS and solubilized in 10 ml of a solution comprising 5 M guanidine thiocyanate, 10 mM EDTA, 50 mM Tris-HCl (pH 7) and 8% (v/v) 2-mercaptoethanol using a vortex mixer. This solubilization product was transferred to a centrifuge tube, 80 ml of 4 M LiCl was added, and the mixture was stirred, then allowed to stand at 4° C. for 20 hours and centrifuged on a Hitachi RPR10 rotor at 9,000 rpm for 90 minutes. Thereafter, an RNA precipitate was recovered. The RNA precipitate was suspended in 50 ml of a solution comprising 4 M urea and 2 M lithium chloride, and the suspension was centrifuged on a Hitachi RPR10 rotor at 9,000 rpm for 60 minutes, and an RNA precipitate was again recovered.

The RNA precipitate was dissolved in 10 ml of a solution comprising 0.1% sodium lauryl sulfate, 1 mM EDTA and 10 mM Tris-HCl (pH 7.5) and the RNA was recovered by phenol-chloroform extraction and ethanol precipitation. The RNA obtained (about 0.8 mg) was dissolved in 1 ml of a solution comprising 10 mM Tris-HCl (pH 8.0) and 1 mM EDTA. After incubation at 65° C. for 5 minutes, 0.1 ml of 5 M NaCl was added. The mixture was subjected to oligo(dT)-cellulose column (P-L Biochemicals) chromatography (column volume 0.5 ml). The adsorbed, poly(A)-containing mRNA was eluted with a solution comprising 10 mM Tris-HCl (pH 7.5) and 1 mM EDTA to give about 30 μg of poly(A)-containing mRNA.

(2) cDNA synthesis and insertion of the DNA into a vector

Figure 9:
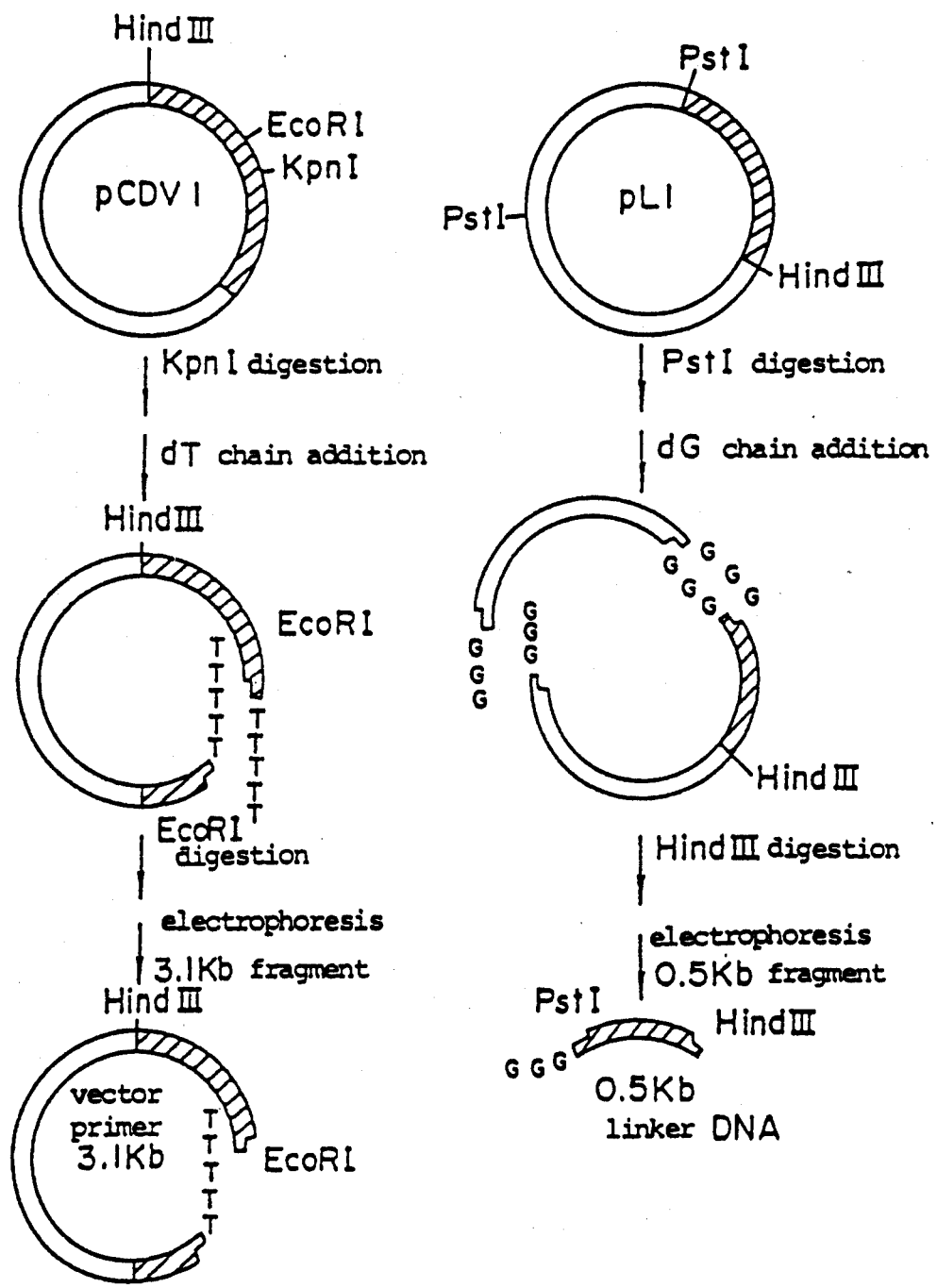
FIG. 9 (1) and (2) schematically show the processes involved in the Okayama-Berg method for cDNA synthesis and construction of a recombinant plasmid containing the DNA synthesized.
Figure 9:
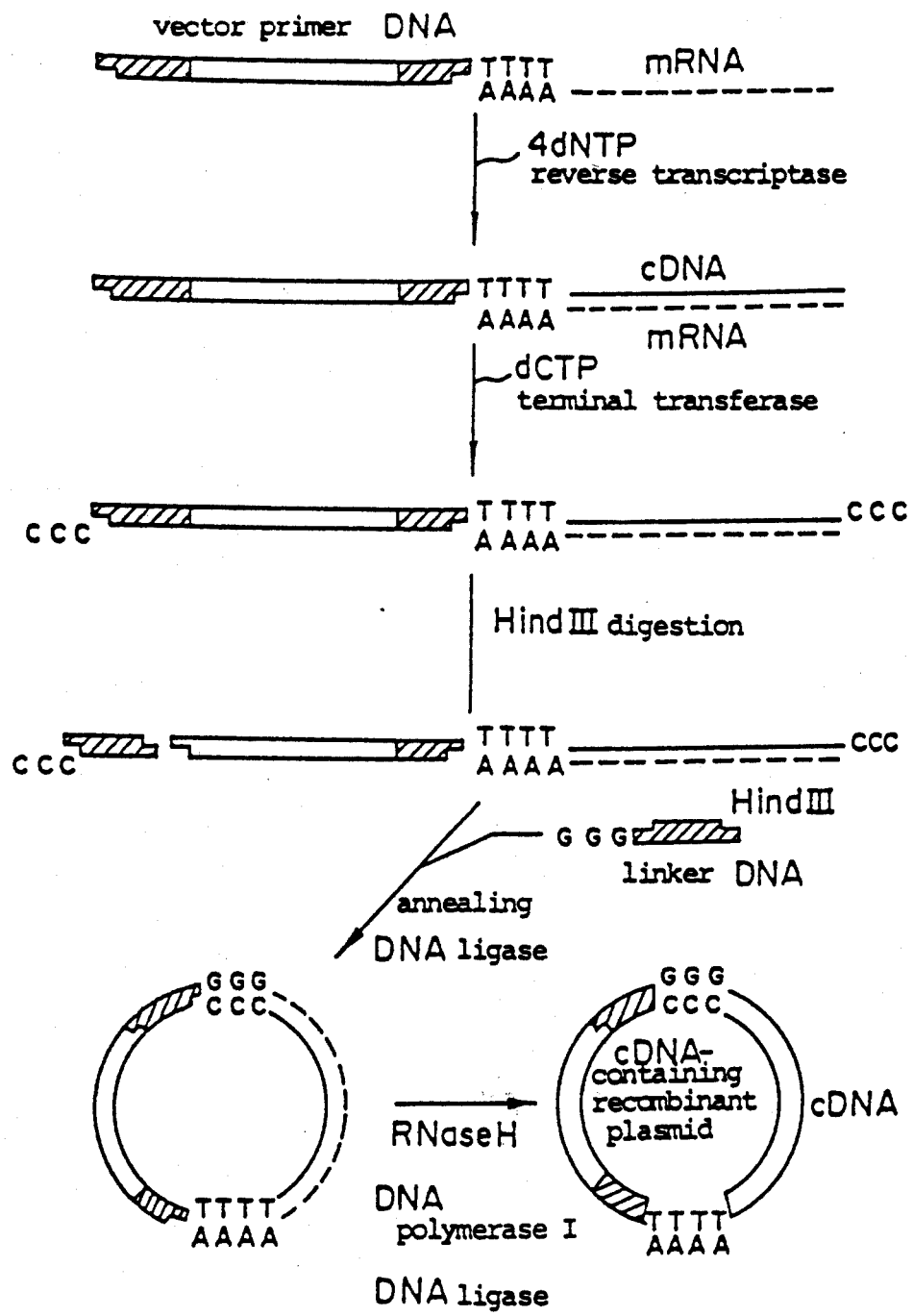
Figure 10:
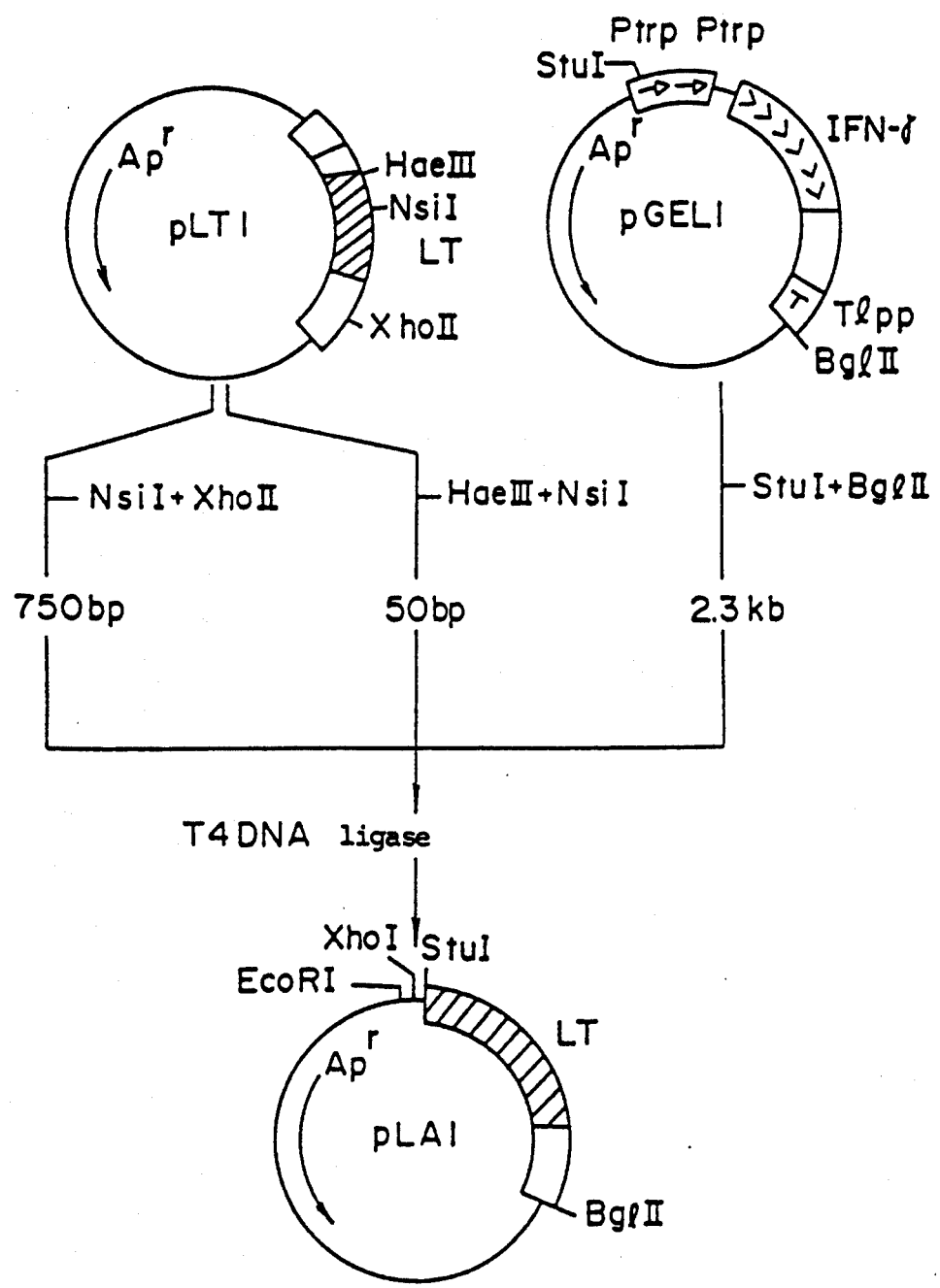
FIG. 10 shows a construction scheme for the plasmid pLA1.
Figure 11:
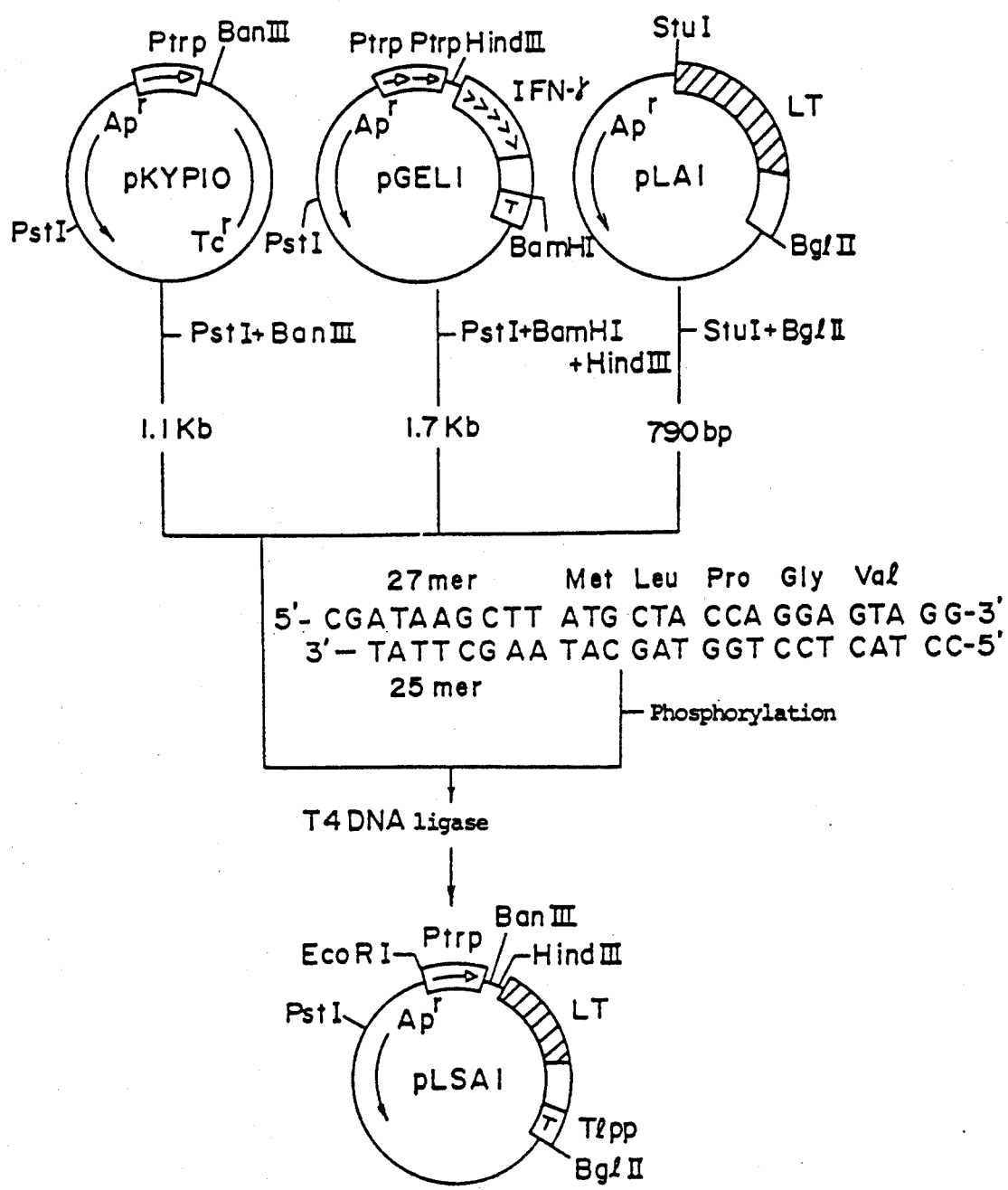
FIG. 11 shows a construction scheme for the plasmid pCfTNS501.

The Okayama-Berg method [Mol. Cell. Biol., 2, 161 (1982)] was used for cDNA synthesis and recombinant plasmid construction by insertion of the cDNA obtained. The processes therefor are outlined in FIG. 9.

To 300 μl of a solution comprising 10 mM Tris-HCl (pH 7.5), 6 mM $MgCl_2$ and 10 mM NaCl, there was added 400 μg of pCDV1 [Okayama & Berg: Mol. Cell. Biol., 3, 280 (1983)] and, after further addition of 500 units of KpnI, the reaction was carried out at 37° C. for 6 hours, whereby the plasmid was cleaved at the KpnI site. The DNA was recovered by phenol-chloroform extraction and ethanol precipitation. About 200 μg of the KpnI-cleaved DNA was added to 200 μl of a solution prepared by adding dTTP in a concentration of 0.25 mM to a buffer (hereinafter abbreviated as TdT buffer) comprising 40 mM sodium cacodylate, 30 mM Tris-HCl (pH 6.8), 1 mM $CaCl_2$ and 0.1 mM dithiothreitol (hereinafter abbreviated as DTT) and, after further addition of 81 units of terminal deoxynucleotidyl transferase (hereinafter abbreviated as TdT) (P-L Biochemicals), the reaction was carried out at 37° C. for 11 minutes, whereby a poly(dT) chain comprising about 67 dT residues was added to each KpnI cleavage site 3' end of pCDV1. About 100 μg of the poly(dT) chain-added pCDV1 DNA was recovered from the above reaction mixture by phenol-chloroform extraction and ethanol precipitation. The DNA was added to 150 μl of a buffer comprising 10 mM Tris-HCl (pH 7.5), 6 mM $MgCl_2$ and 100 mM NaCl, 360 units of EcoRI was further added, and the reaction was carried out at 37° C. for 2 hours. The reaction mixture was treated by the LGT method, and a DNA fragment of about 3.1 kb was recovered. Thus was obtained about 60 μg of the poly(dT) chain-tailed pCDV1. The DNA was dissolved in 500 μl of a solution comprising 10 mM Tris-HCl (pH 8.0) and 1 mM EDTA, the solution was incubated at 65° C. for 5 minutes and then cooled with ice, and 50 μl of 5 M NaCl was added. The mixture was subjected to oligo(dA)-cellulose column (Collaborative Research) chromatography. Molecules having a sufficient poly(dT) chain length were adsorbed on the column and they were eluted with a solution comprising 10 mM Tris-HCl (pH 8.0) and 1 mM EDTA. Thus was obtained 27 μg of the poly(dT) chain-tailed pCDV1 (hereinafter abbreviated as vector primer).

Then, a linker DNA was synthesized.

To 200 μl of a buffer comprising 10 mM Tris-HCl (pH 7.5), 6 mM $MgCl_2$ and 50 mM NaCl, there was added about 14 μg of pL1 [Okayama & Berg: Mol. Cell. Biol., 3, 280 (1983)], 50 units of PstI was further added, and the reaction was carried out at 37° C. for 4 hours, whereby the pL1 DNA was cleaved at the PstI site. The reaction mixture was subjected to phenol-chloroform extraction, followed by ethanol precipitation, whereby about 13 μg of the PstI-cleaved pL1 DNA was recovered. The DNA (about 13 μg) was added to 50 μl of TdT buffer supplemented with dGTP in a final concentration of 0.25 mM, 54 units of TdT (P-L Biochemicals) was further added, and the mixture was incubated at 37° C. for 13 minutes, whereby a (dG) chain containing about 14 dG residues was added to pL1 at each 3' end at the PstI cleavage site. The DNA was recovered by phenol-chloroform extraction followed by ethanol precipitation. The DNA was added to 100 μl of a buffer comprising 10 mM Tris-HCl (pH 7.5), 6 mM $MgCl_2$ and 60 mM NaCl, 80 units of HindIII was further added, and the mixture was incubated at 37° C. for 3 hours, whereby the pL1 DNA was cleaved at the HindIII site. The reaction mixture was fractionated by agarose gel electrophoresis, and a DNA fragment of about 0.5 kb was recovered by the DEAE-paper method [Dretzen et al.: Anal. Biochem., 112, 295 (1981)]. Thus was obtained the oligo(dG) chain-tailed linker DNA (hereinafter referred to simply as linker DNA).

In 22.3 μl of a solution comprising 50 mM Tris-HCl (pH 8.3), 8 mM $MgCl_2$, 30 mM KCl, 0.3 mM DTT, 2 mM dNTP (dATP, dTTP, dGTP and dCTP) and 10 units of ribonuclease inhibitor (P-L Biochemicals), there were dissolved about 3 μg of the poly(A) RNA and about 1.4 μg of the vector primer, each prepared as described above, 10 units of reverse transcriptase (Seikagaku Kogyo) was added, and the mRNA was caused to synthesize a DNA complementary thereto by incubating the mixture at 41° C. for 90 minutes. The reaction mixture was subjected to phenol-chloroform extraction and the vector primer DNA with the RNA-DNA double strand added thereto was recovered by ethanol precipitation. This DNA was dissolved in 20 μl of TdT buffer containing 66 μM dCTP and 0.2 μg of poly(A), 14 units of TdT (P-L Biochemicals) was added, and the mixture was incubated at 37° C. for 2 minutes, whereby a (dC) chain containing 20 dC residues was added to the 3' end of the cDNA. The reaction mixture was extracted with phenolchloroform, and the (dC) chain-tailed cDNA-vector primer DNA was recovered by ethanol precipitation. The DNA was dissolved in 400 μl of a solution comprising 10 mM Tris-HCl (pH 7.5), 6 mM MgCl$_2$ and 60 mM NaCl, 20 units of HindIII was added, and incubation was conducted at 37° C. for 2 hours to cause cleavage at the HindIII site. Phenol-chloroform extraction of the reaction mixture and the subsequent ethanol precipitation gave 0.5 picomole of the (dC) chain-tailed cDNA-vector primer DNA. In 100 μl of a solution comprising 10 mM Tris-HCl (pH 7.5), 0.1 M NaCl and 1 mM EDTA, there were dissolved 0.2 picomole of the DNA and 0.4 picomole of the above-mentioned linker DNA, and incubation was carried out at 65° C., 42° C. and 0° C. for 10 minutes, 25 minutes and 30 minutes, respectively. A total volume of 1,000 μl of a reaction mixture was prepared which had the following composition: 20 mM Tris HCl (pH 7.5), 4 mM MgCl$_2$, 10 mM (NH4)2SO$_4$, 0.1 M KCl and 0.1 mM β-NAD. To this reaction medium was added 25 units of *E. coli*-derived DNA ligase (New England Bio-Labs), and incubation was carried out at 11° C. for 18 hours. The reaction medium was supplemented with 40 μM each dNTP and with β-NAD to give a final concentration of 0.15 mM, 10 units of *E. coli* DNA ligase, 20 units of *E. coli* DNA polymerase I (P-L Biochemicals) and 10 units of *E. coli* ribonuclease H (P-L Biochemicals) were added, and incubation was carried out at 12° C. for 1 hour and then at 25° C. for 1 hour. The above reaction procedure caused circularization of the cDNA-containing recombinant DNA and substitution of the RNA portion of the RNA-DNA double strand by the corresponding DNA. Thus was formed the recombinant plasmid in the completely double-stranded DNA form.

(3) Selection of the hG-CSF cDNA-containing recombinant DNA

The recombinant plasmid obtained as described in (2) was used to transform *E. coli* C600SF8 by the method of Scott et al. [Katsuya Shigesada: Saibo Kogaku (Cell Technology), 2, 616 (1983)]. About 9,200 colonies obtained were fixed on a nitrocellulose filter. One strain capable of associating strongly at 60° C. with a probe prepared by labeling, with $^{32}$P, the 27-base synthetic DNA 5'-ACCCCCCTGGGCCCTGCCAGCTCCCTG-3' corresponding to the N-terminal 9 amino acids of the mature hG-CSF protein as isolated by Nagata et al [Nagata et al.: Nature, 319, 415 (1986)] was selected [the Grunstein-Hogness method; Proc. Natl. Acad. Sci. USA, 72, 3961 (1975)]. The whole base sequence of the cDNA contained in the plasmid pCSF1-2 carried by this strain was determined by the dideoxy sequencing method using M13 phage (Table 1). As a result, it was found that the cDNA contained in pCSF1-2 codes for hG-CSF.

This bacterial strain has been deposited with the FRI under the designation *E. coli* ECSF1-2 (FERM BP-1220), as mentioned hereinabove.

REFERENCE EXAMPLE 2

Isolation and purification of the plasmid pKYP26

A pKYP26-bearing *E. coli* strain [*E. coli* IKYP26 (FERM BP-863)] was cultured in 10 ml of L medium (1% Bacto-tryptone, 0.5% yeast extract, 1% NaCl, pH 7.5) containing 50 μg/ml of ampicillin at 37° C. for 18 hours. The whole culture was transferred to 1 liter of L medium containing 50 μg/ml of ampicillin, and cultured at 37° C. After 4 hours, chloramphenicol was added in a concentration of 170 μg/ml, and cultivation was continued at 37° C. for additional 16 hours. Cells were harvested by centrifugation (5,000 rpm, 10 minutes), washed with 0.8% NaCl and suspended in 20 ml of 50 mM Tris-HCl (pH 8.0), and the suspension was cooled with ice. Lysozyme (10 mg/ml, 8 ml) was added and, after standing in ice for 10 minutes, 9.6 ml of 0.5 M EDTA was added. After standing in ice for 10 minutes, 2.3 ml of 2% Triton X-100 (Wako Pure Chemical Industries) was added, followed by further standing in ice for 1 hour. Ultracentrifugation at 50,000×g at 4° C. for 1 hour gave about 40 ml of a supernatant. Then, this supernatant was adjusted to pH 12.5 by addition of 3 M NaOH and stirred gently at room temperature for 10 minutes. The pH was brought back to 8.5 by addition of 2 M Tris-HCl (pH 7.5), followed by further stirring for 3 minutes. At this timepoint, the liquid volume was about 55 ml. A 1/9 volume of 5 M NaCl was added and then phenol extraction was carried out. A 1/250 volume of 5 mg/ml RNase A (Sigma) was added, the RNA degradation reaction was conducted at 37° C. for 1 hour, a 1/5 volume of 5 M NaCl was then added, and a ⅓ volume of 30% PEG 6000 (Nakarai Chemicals) was added. The resultant mixture was allowed to stand at −20° C. for 2 hours. The resultant precipitate was collected by centrifugation and dissolved in 2 ml of a solution comprising 10 mM Tris-HCl (pH 7.5) and 1 mM EDTA, sodium dodecyl sulfate (SDS) was added in a concentration of 0.5%, proteinase K (Sigma) was added in a concentration of 50 μg/ml, and the proteolytic reaction was carried out at 37° C. for 1 hour. After three repetitions of phenol extraction, the DNA was recovered by chloroform extraction and ethanol precipitation, and dissolved in 1 ml of a solution comprising 10 mM Tris-HCl (pH 7.5) and 1 mM EDTA. In this way, 800 μg of pKYP26 could be obtained. The structure of pKYP26 was confirmed by cleavage with EcoRI, KpnI, BamHI, BglII and PstI, followed by agarose gel electrophoresis.

REFERENCE EXAMPLE 3

1) Isolation of the human LT cDNA-carrying plasmid pLT (1) Preparation of poly(A) RNA from LukII cells The guanidine thiocyanate-lithium chloride method [Cathala et al.: DNA, 2, 329 (1983)] was followed to prepare a poly(A)-carrying RNA from the human lymphoblastoid cell line LukII, as follows:

Human lymphoblastoid LukII cells [Berish Y. Rubin et al.: Proc. Natl. Acad. Sci. USA, 82, 6637 (1985)] were sowed into 1 liter of RPMI 1640 medium (Nissui Seiyaku) containing 5% fetal bovine serum and 1 mM N-2-hydroxyethylpiperazine-N'-ethanesulfonic acid (HEPES) in a cell concentration of $8 \times 10^5$ cells/ml and grown there. A spinner culture bottle was used for the culture. After cultivation at 37° C. for 48 hours, cells were collected by centrifugation and transferred to a fresh-liter portion or RPMI 1640 medium containing 5% fetal bovine serum and 1 mM HEPES, and cultivation was conducted at 37° C. for further 48 hours. Then cells were harvested from a portion (250 ml) of this cell suspension by centrifugation at $1,100 \times g$ at 4° C. for 10 minutes, washed with 80 ml of phosphate buffer, and solubilized in 10 ml of a solution comprising 5 M guanidine thiocyanate, 10 mM EDTA, 50 mM Tris-HCl (pH 7) and 8% (v/v) 2-mercaptoethanol using a vortex mixer. The solubilization product was transferred to a centrifuge tube, 80 ml of 4 M LiCl was added, and the mixture was stirred and then allowed to stand at 4° C. for 20 hours. After centrifugation on a Hitachi RPR10 rotor at 9,000 rpm for 90 minutes, an RNA precipitate was recovered. The RNA precipitate was suspended in 50 ml of a solution comprising 4 M urea and 2 M lithium chloride and, after centrifugation on a Hitachi RPR10 rotor at 9,000 rpm for 60 minutes, the RNA was again recovered as a precipitate the RNA precipitate was dissolved in 10 ml of a solution comprising 0.1% sodium lauryl sulfate, 1 mM EDTA and 10 mM Tris-HCl (pH 7.5), and the RNA was recovered by phenol-chloroform extraction followed by ethanol precipitation. About 2.5 mg of the thus-obtained RNA was dissolved in 1 ml of a solution comprising 10 mM Tris-HCl (pH 8.0) and 1 mM EDTA. After incubation at 65° C. for 5 minutes, 0.1 ml of 5 M NaCl was added. The mixture was subjected to oligo(dT)-cellulose column (P-L Biochemicals) chromatography (column volume 0.5 ml). The adsorbed, poly(A)-containing mRNA was eluted with a solution comprising 10 mM Tris-HCl (pH 7.5) and 1 mM EDTA. About 100 μg of the poly(A)-containing mRNA.

(2) cDNA synthesis and insertion of the DNA into a vector

The Okayama-Berg method [Mol. Cell. Biol., 2, 161 (1982)] was followed for cDNA synthesis and recombinant plasmid construction by insertion of the cDNA obtained. The processes therefor are outlined in FIG. 9.

To 300 μl of a solution comprising 10 mM Tris-HCl (pH 7.5), 6 mM $MgCl_2$ and 10 mM NaCl, there was added 400 μg of pCDV1 [Okayama & Berg: Mol. Cell. Biol., 3, 280 (1983)] and, after further addition of 500 units of KpnI, the reaction was carried out at 37° C. for 6 hours, whereby the plasmid was cleaved at the KpnI site. The DNA recovered by phenol-chloroform extraction followed by ethanol precipitation. About 200 μg of the KpnI-cleaved DNA was added to 200 μl of a solution prepared by adding dTTP in a concentration of 0.25 mM to TdT buffer and, after further addition of 81 units of TdT (P-L Biochemicals), the reaction was carried out at 37° C. for 11 minutes, whereby a poly(dT) chain (about 67 dT residues) was added to each 3' end of the KpnI cleavage site of pCDV1. About 100 μg of the poly(dT) chain tailed pCDV1 DNA was recovered from the solution by ethanol precipitation following phenol-chloroform extraction. The DNA was added to 150 μl of a solution comprising 10 mM Tris-HCl (pH 7.5), 6 mM $MgCl_2$ and 100 mM NaCl and, after further addition of 360 units of EcoRI, the reaction was carried out at 37° C. for 2 hours. The reaction mixture was treated by the LGT method, and a DNA fragment of about 3.1 kb was recovered. About 60 μg of the poly(dT) chain-tailed pCDV1 was thus obtained. The DNA was dissolved in and 1 mM EDTA, the solution was incubated at 65° C. for 5 minutes and then cooled with ice, and 50 μl of 5 M NaCl was added. The mixture was subjected to oligo(dA)-cellulose column (Collaborative Research) chromatography. Molecules having a sufficient poly(dT) chain length were adsorbed on the column and they were eluted with a solution comprising 10 mM Tris-HCl (pH 8.0) and 1 mM EDTA to give 27 μg of the poly(dT) chain-tailed pCDV1 (hereinafter referred to as vector primer).

Then, a linker DNA was prepared.

About 14 μg of pL1 [Okayama & Berg: Mol. Cell. Biol., 3, 280 (1983)] was added to 200 μl of a buffer comprising 10 mM Tris-HCl (pH 7.5), 6 mM $MgCl_2$ and 50 mM NaCl and, after further addition of 50 units of PstI, the reaction was carried out at 37° C. for 4 hours for cleavage of the pL1 DNA at the PstI site. The reaction mixture was subjected to phenol-chloroform extraction and about 13 μg of the PstI-cleaved pL1 DNA was recovered by ethanol precipitation. About 13 μg of the DNA was added to 50 μl of TdT buffer containing dGTP in a final concentration of 0.25 mM and, after further addition of 54 units of TdT (P-L Biochemicals), incubation was carried out at 37° C. for 13 minutes to cause addition of a (dG) chain (about 14 dG residues) to pL1 at each PstI cleavage site 3' end. After phenol-chloroform extraction, the DNA was recovered by ethanol precipitation. The DNA was added to 100 μl of a buffer comprising 10 mM Tris-HCl (pH 7.5), 6 mM $MgCl_2$ and 60 mM NaCl and, after further addition of 80 units of HindIII, incubation was carried out at 37° C. for 3 hours to cause cleavage of the pL1 DNA at the HindIII site. The reaction mixture was fractionated by agarose gel electrophoresis, and a DNA fragment of about 0.5 kb was recovered by the DEAE-paper method [Dretzen et al.: Anal. Biochem., 112, 295 (1981)]. Thus was obtained the oligo(dG) chain-tailed linker DNA (hereinafter referred to simply as linker DNA).

About 2 μg of the poly(A) RNA and about 1.4 μg of the vector primer dissolved in 22.3 μl of a solution comprising 50 mM Tris-HCl (pH 8.3), 8 mM $MgCl_2$, 30 mM KCl, 0.3 mM DTT, 2 mM dNTP (dATP, dTTP, dGTP and dCTP) and 10 units of ribonuclease inhibitor (P-L Biochemicals), 10 units of reverse transcriptase (Seikagaku Kogyo) was added, and incubation was carried out at 41° C. for 90 minutes to cause the mRNA to synthesize a DNA complementary thereto. The reaction mixture was subjected to phenol-chloroform extraction followed by ethanol precipitation, whereby the vector primer DNA with the RNA-DNA double strand added thereto was recovered. The DNA was dissolved in 20 μl of TdT buffer containing 66 μM dCTP and 0.2 μg of poly(A), 14 units of TdT (P-L Biochemicals) was added, and incubation was performed at 37° C. for 2 minutes to cause addition of a (dC) chain (20 dC residues) to the 3' end of the cDNA. The reaction mixture was subjected to phenol-chloroform extraction and then the (dC) chain-tailed cDNA-vector primer DNA was recovered by ethanol precipitation. The DNA was dissolved in 400 μl of a solution comprising 10 mM Tris-HCl (pH 7.5), 6 mM $MgCl_2$ and 60 mM NaCl, 20 units of HindIII was added, and incubation was carried out at 37° C. for 2 hours for cleavage at the HindIII site. Phenol-chloroform extraction of the reaction mixture and ethanol precipitation gave 0.5 picomole of the (dC) chain-tailed cDNA-vector primer DNA. The DNA (0.2 picomole) was dissolved in 100 μl of a solution comprising 10 mM Tris-HCl (pH 7.5), 0.1 M NaCl and 1 mM EDTA, and incubation was carried out at 65° C., 42° C. and 0° C. for 10 minutes, 25 minutes and 30 minutes, respectively, in that order. A total volume of 100 μl of a reaction medium was prepared according to the following composition: 20 mM Tris-HCl (pH 7.5), 4 mM MgCl$_2$, 10 mM (NH$_4$)SO$_4$, 0.1 M KCl and 0.1 mM β-NAD. To this reaction medium, there was added 25 units of $E.$ $coli$ DNA ligase (New England Bio-Labs), and incubation was performed at 11° C. for 18 hours. The reaction medium was supplemented with 40 μM each dNTP and with β-NAD in a final concentration of 0.15 mM and, after addition of 10 units of $E.$ $coli$ DNA ligase, 20 units of $E.$ $coli$ DNA polymerase I (P-L Biochemicals) and 10 units of $E.$ $coli$ ribonuclease H (P-L Biochemicals), incubation was carried out at 12° C. for 1 hour and then at 25° C. for 1 hour. The above reaction procedure caused circularization of the cDNA-containing recombinant DNA and substitution of the RNA portion of the RNA-DNA double strand by the corresponding DNA. Thus, the recombinant plasmid was formed in the form of a completely double-stranded DNA.

(3) Selection of the human LT cDNA-containing recombinant DNA

The recombinant plasmid obtained as described in (2) was used to transform $E.$ $coli$ C600SF8[Cameron: Proc. Natl. Acad. Sci. USA, 72, 3416 (1975)] by the method of Scott et al. [Katsuya Shigesada: Saibo Kogaku (Cell Technology), 2, 616 (1983)]. About 30,000 colonies obtained were fixed on a nitrocellulose filter. One strain capable of strongly associating, at 52° C., with a probe prepared by labeling, with $^{32}$P, the 17-base synthetic DNA 5'-GATCCCCGGCCTGCCTG-3' corresponding to the base sequence of part of the 5' nontranslational region of the human LT cDNA isolated by Genentech [Patrick W. Gray et al.: Nature, 312, 721 (1984)] was selected [Grunstein-Hogness method: Proc. Natl. Acad. Sci. USA, 72, 3961 (1975)]. The whole base sequence of the cDNA of the plasmid pLT1 carried by this strain was determined by the dideoxy sequencing method using M13 phage. As a result, it was found that the pLT1 DNA codes for human LT.

(4) Construction of the recombinant plasmid pLA1

In a total of 50 μl of a solution (hereinafter referred to as "Y-0 buffer") containing 10 mM Tris-HCl (pH 7.5), 7 mM MgCl$_2$ and 6 mM 2-mercaptoethanol, there was dissolved 5 μg of pLT1 (4.7 kb) obtained by the procedure described in the preceding section, 10 units of the restriction enzyme XhoII (Boehringer Mannheim) was added, and the cleavage reaction was conducted at 37° C. for 2 hours. Then, NaCl was added in a final concentration of 150 mM, 10 units of the restriction enzyme NsiI (New England Bio-Labs) was added, and the cleavage reaction was carried out at 37° C. for further 3 hours. From the reaction mixture, there was obtained, by the LGT method, about 0.3 μg of an about 750 bp DNA fragment (XhoII-NsiI fragment) containing most of the human LT DNA.

Separately, 20 μg of pLT1 was dissolved in 200 μl of Y-50 buffer, 40 units of the restriction enzyme HaeIII was added, and the cleavage reaction was performed at 37° C. for 2 hours. Then, NaCl was added in a final concentration of 150 mM, 40 units of NsiI was added, and the cleavage reaction was carried out at 37° C. for further 3 hours. Polyacrylamide gel electrophoresis of the reaction mixture gave about 40 ng of an about 50 bp DNA fragment (HaeIII-NsiI fragment) containing the N-terminal portion of human LT.

Further, separately, 3 μg of pGEL1 (3.4 kb) was dissolved in a total of 30 μl of Y-100 buffer, 6 units each of the restriction enzymes StuI and BglII were added, and the cleavage reaction was carried out at 37° C. for 3 hours.

From the reaction mixture, there was obtained, by the LGT method, about 1.0 μg of an Ap$^r$ gene-containing DNA fragment of about 2.3 kb (StuI-BglII fragment).

Then, 0.2 μg of the pLT1-derived XhoII-NsiI fragment (about 750 bp), 20 ng of the pLT1-derived HaeIII-NsiI fragment (about 50 bp) and 0.6 μg of the pGEL1-derived StuI-BglII fragment (about 2.3 kb) were dissolved in a total of 20 μl of T4 ligase buffer, 2 units of T4 DNA ligase (Takara Shuzo) was further added to this mixture solution, and the reaction was carried out at 4° C. for 18 hours.

The recombinant plasmid DNA thus obtained was used to transform $E.$ $coli$ KM430 by the method of Cohen et al., and an Ap$^r$ colony was obtained. The plasmid DNA was isolated and purified from this transformant by a known method, and the structure of the plasmid was analyzed by cleavage of said plasmid DNA with restriction enzymes such as StuI. As a result, it was confirmed that the desired plasmid had been obtained. This recombinant plasmid is named pLA.

(5) Construction of the LT expression plasmid pLSA1

An $E.$ $coli$ KM430 transformant harboring pLA1 (3.1 kb) obtained as described in the preceding section was cultured, and the pLA1 DNA was prepared from cultured cells thereof in the conventional manner. In 30 μl of Y-100 buffer, there was dissolved 3 μg of the pLA1 DNA obtained, 3 units each of StuI and BglII were added, and the cleavage reaction was conducted at 37° C. for 3 hours. From the reaction mixture, there was obtained, by the LGT method, about 0.5 μg of an about 790 bp DNA fragment (StuI-BglII fragment) containing most of the human LT gene.

Separately, 3 μg of pKYP10 prepared by the method described in U.S. Pat. No. 4,686, 191 was dissolved in 30 1 of Y-100 buffer, 6 units each of the restriction enzymes BanIII and PstI were added, and the cleavage reaction was carried out at 37° C. for 3 hours. From the reaction mixture, there was obtained, by the LGT method, a tryptophan promoter (Ptrp)containing DNA fragment of about 1.1 kb (BanIII-PstI fragment). Further, 2 μg of pGEL1 (3.4 kb) was dissolved in 20 μl of Y-100 buffer, 4 units each of the restriction enzymnes HindIII, BamHI and PstI were added, and the cleavage reaction was carried out at 37° C. for 3 hours. From the reaction mixture, there was obtained, by the LGT method, about 0.7 μg of a lipoprotein-derived terminator-containing DNA fragment of about 1.7 kb (PstI-BamHI fragment).

Separately, for such reasons as the necessity of providing the sequence from the N terminus of the mature human LT polypeptide, namely Leu (CTA) to the second base (GG) of the 5th amino acid Gly (GGC) as well as the initiation codon (ATG) required for expression and the necessity of adjusting the distance between the SD sequence downstream from Ptrp and ATG to an appropriate length of 6–18 bp, the following DNA linker was synthesized:

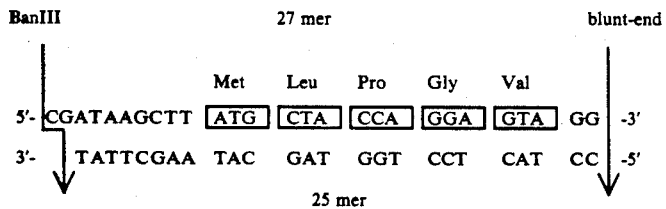

First, the 27-mer and 25-mer single-strand DNAs were synthesized by the ordinary phosphotriester method. The 27-mer and 25-mer (each 20 picomoles) were dissolved in a total of 40 μl of T4 kinase buffer, 6 units of T4 polynucleotide kinase (Takara Shuzo) was added, and the phosphorylation reaction was carried out at 37° C. for 60 minutes.

Then, 0.3 μg of the pLA1-derived StuI-BglII fragment (about 790 bp), 0.4 μg of the BanIII-PstI fragment (about 1.1 kb) of the expression vector pKYP10 and 0.6 μg of the pGEL1-derived PstI-BamHI fragment (about 1.7 kb), each obtained as described above, were dissolved in 25 μl of T4 ligase buffer, and about 1 picomole of the above DNA linker was added to this mixture solution. After further addition of 6 units of T4 DNA ligase to this mixture, the ligation reaction was conducted at 4° C. for 18 hours.

The recombinant plasmid-containing reaction mixture was used to transform E. coli KM430, and an Ap$^r$ colony was obtained. The plasmid DNA was recovered from cultured cells of this colony. The structure of the plasmid obtained was confirmed by cleavage with the restriction enzymes EcoRI, BanIII, PstI, HindIII and BglII followed by agarose gel electrophoresis. This plasmid is named pLSA1. The base sequence of pLSA1 in the vicinity of BanIII and HindIII was confirmed by the Maxam-Gilbert method [(A. M. Maxam et al.: Proc. Natl. Acad. Sci. USA, 74, 560 (1977)] to be as follows:

Separately, the following DNA linker was synthesized by the phosphotriester method for providing the initiation codon ATG downstream from Ptrp:

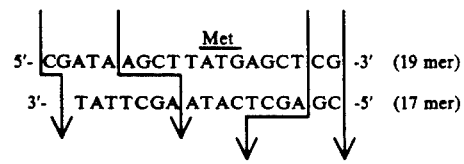

The 19-mer and 17-mer synthetic DNAs (each 10 picomoles) were dissolved in a total of 20 μl of a solution containing 50 mM Tris-HCl (pH 7.5), 10 mM MgCl$_2$, 5 mM dithiothreitol, 0.1 mM EDTAs and 1 mM ATP, 3 units of T4 polynucleotide kinase (Takara Shuzo) was added, and the phosphoryolation reaction was effected at 37° C. for 60 minutes.

Then, 0.1 μg of the pKYP10-derived BanIII-NruI fragment (about 3.8 kb) obtained as described above and about 0.5 picomole of the above DNA linker were dissolved in 20 μl of T4 ligase buffer, 2 units of T4 DNA ligase was further added, and the ligation reaction was carried out at 4° C. for 18 hours.

The recombinant plasmid mixture obtained was used to transform E. coli HB101 [Boliver et al.: Gene, 2, 75 (1977)], and an Ap$^r$ colony was obtained. From cultured cells of this colony, there was recovered the plasmid DNA . The structure of the plasmid obtained was confirmed by cleavage with the restriction enzymes EcoRI, BanIII, HindIII, SacI and NruI, followed by agarose gel electrophoresis. This plasmid was named pTrS20

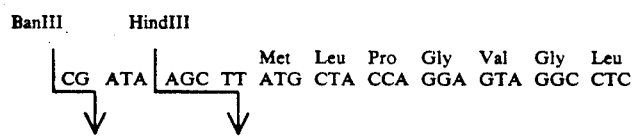

REFERENCE EXAMPLE 4

Construction of the ATG vector pTrS20

Figure 13:
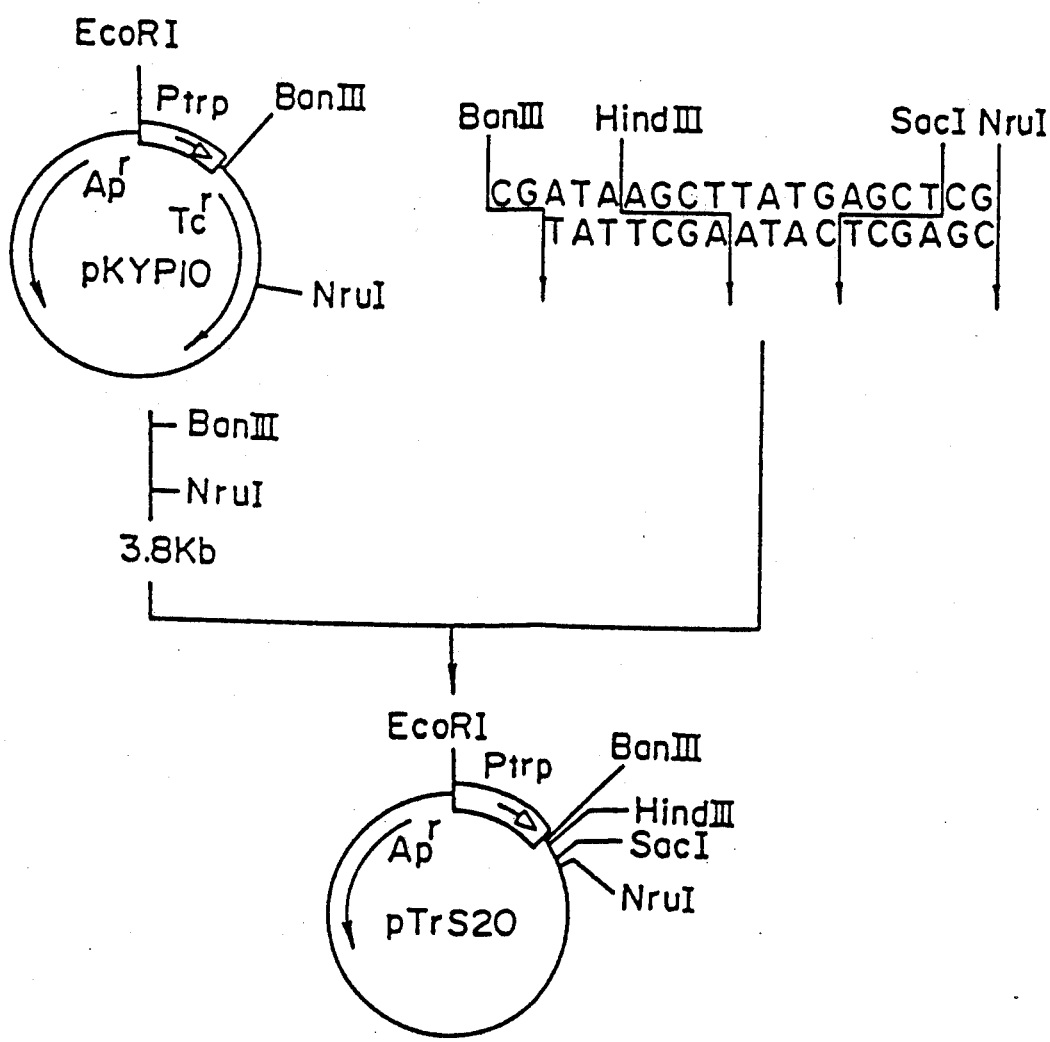
FIG. 13 shows a construction scheme for the plasmid pTrS20.

By following the procedure shown in FIG. 13, the ATG vector pTrS20 in which the distance between the SD sequence and the initiation codon ATG is 14 bases and which has an SacI site immediately behind the ATG codon was constructed.

First, 3 μg of pKYP10 prepared by the method described in U.S. Pat. No. 4,686,191 was dissolved in 30 μl of Y-100 buffer, 6 units each of the restriction enzymes BanIII and NruI (New England Bio-Labs) were added, and the cleavage reaction was conducted at 37° C. for 3 hours. From the reaction mixture, there was obtained, by the LGT method, about 0.5 μg of a Ptrp-containing DNA fragment of about 3.8 kb (BanIII-NruI fragment).

(FIG. 13). The base sequence of pTrS20 in the neighborhood of the BanIII and HindIII sites was confirmed by the dideoxy sequencing method using M13 phage to be as follows:

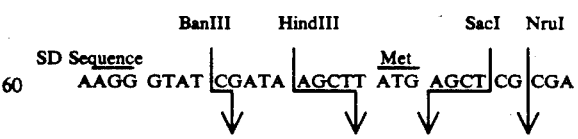

EXAMPLE 23

(1) Preparation of immunized mouse splenic cells

ND28 (100 μg/head) prepared in Example 8 was intraperitoneally administered to five head of BALB/c female mice 8 weeks old (Experimental Animal Agricultural Cooperative Association of Shizuoka Prefecture), together with 2 mg/head of aluminum hydroxide gel and $1 \times 10^9$ cells/head of purtussis vaccine (Chiba Serum Research Institute) as adjuvants to effect the first immunization. After that, 100 μg/head of ND28 was intraperitoneally administered at intervals of two weeks to effect the second and succeeding immunization. From the third immunization, blood samples were taken from the venous plexus at the eyeground five to seven days after each administration, and the anti-ND28 antibody titer of the serum was measured by the solid-phase enzyme immunoassay as described above.

An appreciable magnitude of antibody titer was observed with all the five mice after the third immunization, but immunization was repeated five times to effectively obtain a monoclonal antibody of the IgG class.

ND28 (100 μg/head) was further administered intraperitoneally (final immunization), and the spleen was extracted from each mouse to prepare splenic cells to be used for cell fusion.

(2) Preparation of mouse myeloma cells

Mouse myeloma cells resistant to 8-azaguanine (P3-U1) were cultured at 37° C. in the normal medium (RPMI-1640 medium supplemented with 1.5 mM glutamine, $5 \times 10^{31.5}$ M 2-mercaptoethanol, 10 μg/ml gentamycin and 0.1 ml/ml FCS), giving more than $2 \times 10^7$ cells four days later.

(3) Preparation of hybridoma

The splenic cells of immunized mice ($1 \times 10^8$) and the mouse myeloma cells P3-U1 ($2 \times 10^7$), both thoroughly washed with MEM medium (product of Nissui Seiyaku), were mixed together, and the mixture was subjected to centrifugation at 1,200 rpm for five minutes.

The mixture of the two types of cells thus obtained was thoroughly loosened, 0.5 ml of a solution prepared by mixing 2 g polyethylene glycol (PEG-1000), 2 ml MEM medium and 0.7 ml dimethyl sulfoxide was added with stirring at 37° C., and the resulting mixture was allowed to stand for one minute. MEM medium (1 ml) was then added five times at intervals of one minute, and finally MEM medium was added to make up a total volume of 50 ml. The resulting mixture was centrifuged at 900 rpm, the supernatant was discarded, the cell pellet thus obtained was gently loosened, 100 ml of the normal medium was added, and the mixture was gently treated with a 10-ml measuring pipette to suspend the cells.

This suspension was dispensed on a 24-well culture plate (Flow Laboratories, U.S.A.) in amounts of 1 ml/well and incubated at 37° C. for 24 hours in a 5%-$CO_2$ incubator. HAT medium (the above-mentioned normal medium supplemented with $10^{-4}$ M hypoxanthine, $1.5 \times 10^{-5}$ M thymidine and $4 \times 10^{-7}$ M aminopterin) was then added in amounts of 1 ml/well, and incubation was continued for 24 hours. After discarding 1 ml of supernatant from each well and supplying 1 ml of HAT medium, incubation was continued at 37° C. for 24 hours. After that, 1 ml of culture supernatant was again discarded from each well, 1 ml HAT medium was added, and incubation was continued at 37° C. for 10 to 14 days.

With the wells in which growth of fused cell colonies was observed, 1 ml of culture supernatant was discarded, 1 ml of HT medium (HAT medium with aminopterin removed therefrom) was supplied, and incubation was continued at 37° C. This medium replacement was repeated on the following two days, incubation was continued for four days, and a part of culture supernatant was taken out and measured to determine the anti-ND28 antibody titer by the enzyme immunoassay described above.

With the wells in which an appreciable magnitude of antibody titer was observed, cloning was repeated tow times by the limiting dilution method, and the cells that showed consistent values of antibody titer were selected as a hybridoma cell capable of producing anti-ND28 monoclonal antibody (hybridoma cell KM-498). This cell was deposited at the Fermentation Research Institute (Agency of Industrial Science and Technology) on Jan. 20, 1988, as murine B cell hybridoma KM-498 FERM BP-1665 in accordance with the Budapest Treaty.

(4) Partial purification of the monoclonal antibody

The hybridoma cell obtained above was intraperitoneally administered to BALB/c female mice of 8-weeks of age previously treated with pristane (intraperitoneal administration of 0.5 ml/head 2,6,10,14-tetramethylpenta-decane, followed by feeding for two weeks) in an amount of $4 \times 10^6$ cell/head. The hybridoma caused ascites carcinoma in 10 to 21 days. The ascites (4 to 10 ml) was taken out of each mouse, centrifuged to remove the solid matter, and subjected to ammonium sulfate precipitation (50% and 40% saturation), followed by dialysis against PBS (pH 7.2) for two days. The dialyzate thus obtained was recovered as crude monoclonal antibody KM-498.

Quantitative analysis of protein is made by Folin's method, the amount being calculated from the absorbance at 280 nm (1.4 ($OD_{280}$)=Immunoglobulin 1 mg/ml].

(5) Antigen specificity of the crude monoclonal antibody

The antigen specificity of the crude monoclonal antibody obtained above was measured by the solid-phase enzyme immunoassay. As antigens, there were used ND28, natural G-CSF [Nature, 319, 415 (1986); Science, 232, 61 (1986)], foreign proteins derived from host Escherichia coli, and bovine serum albumin (BSA; product of Seikagaku Kogyo Co., Ltd.). The results are shown in Table 8.

TABLE 8

| | | Avidity ($OD_{415}$) | | | |
|---|---|---|---|---|---|
| Antibody | concn. or dilution | ND28 | Natural G-CSF | BSA | Foreign proteins derived from E. coli |
| Normal mouse serum | $\times 10^{-2}$ | 0.020 | 0.015 | 0.010 | 0.060 |
| ND28-Immunized mouse serum | $\times 10^{-2}$ | 0.950 | 0.930 | 0.005 | 0.020 |
| Crude monoclonal | 10 μg/ml | 1.280 | 0.005 | 0.005 | 0.025 |

TABLE 8-continued

| Antibody | Avidity (OD$_{415}$) | | | |
|---|---|---|---|---|
| | concn. or dilution | ND28 | Natural G-CSF | BSA | Foreign proteins derived from E. coli |
| antibody KM-498 | | | | | |

The crude monoclonal antibody was purified by adsorption in a DEAE-Sepharose column, followed by elution and collection of the IgG fraction.

(6) Classification of the monoclonal antibody

As a result of our investigation of the isotype and subclass of the monoclonal antibody KM-498 according to the Ouchterlony method (Biochemical Experiment No. 15 (p74) in "A Guide to Experimental Immunology" published from Gakkai Shuppan Center in 1981), it was identified as belonging to the IgG$_1$ class.

EXAMPLE 24

A solution of 10 mg anti-ND28 monoclonal antibody KM-498 obtained in Example 23 in 10 ml PBS was allowed to react with 1 ml of CNBr-activated Sepharose-4B (Pharmacia Fine Chemicals) to immobilize the monoclonal antibody. This was charged in a column, and 5 ml of a culture extract containing 3 mg ND28 was passed through that column. It was found that 2.6 mg (87%) of the ND28 was adsorbed on the column.

After washing with PBS, elution with an aqueous solution containing 7 M urea and 1 M NaCl gave 2.10 mg ND28 (81% of the adsorbed substance) as a fraction. An approximately 5000-fold purification could be achieved by this single column treatment.

In contrast, natural G-CSF was not absorbed at all on the above column.

EXAMPLE 25

A 100 µg/ml solution of rabbit antiserum against natural G-CSF (prepared by immunizing rabbits with natural G-CSF) was dispensed as the first antibody on a 96-well EIA plate (Flow Laboratories, U.S.A.) in amounts of 50 µl/well, and allowed to stand at 4° C. for 24 hours to coat the bottom surface of each well with this first antibody. A 1% solution of bovine serum albumin in PBS was then dispensed in amounts of 200 ml/well to cover the rest of protein-binding radicals on the bottom of each well, and allowed to stand at 4° C. for 24 hours. After thorough washing with deionized water, 75 to 5 µg/ml solutions of ND28 were dispensed in amounts of 50 µl/well, and the plate was allowed to stand at 22° to 26° C. for two hours. After thorough washing with PBS, a 10 µg/ml solution of biotinized KM-498 was dispensed as a second antibody in amounts of 50 µg/well, and allowed to stand for 12 to 19 hours at 4° C. After washing with PBS, a 10 µg/ml solution of avidin-biotin-peroxidase (product of Vector Inc.) was added in amounts of 100 µl/well, and allowed to stand at for 22° to 26° C. for one hour. After washing with PBS, an ABTS substrate solution was added in amounts of 100 µl/well, the reaction was allowed to proceed at room temperature for 30 minutes and then terminated by addition of 5% SDS solution (100 µl/well), and the color was measured for each well by the use of an absorptionmeter (OD$_{415}$ nm).

Figure 18:
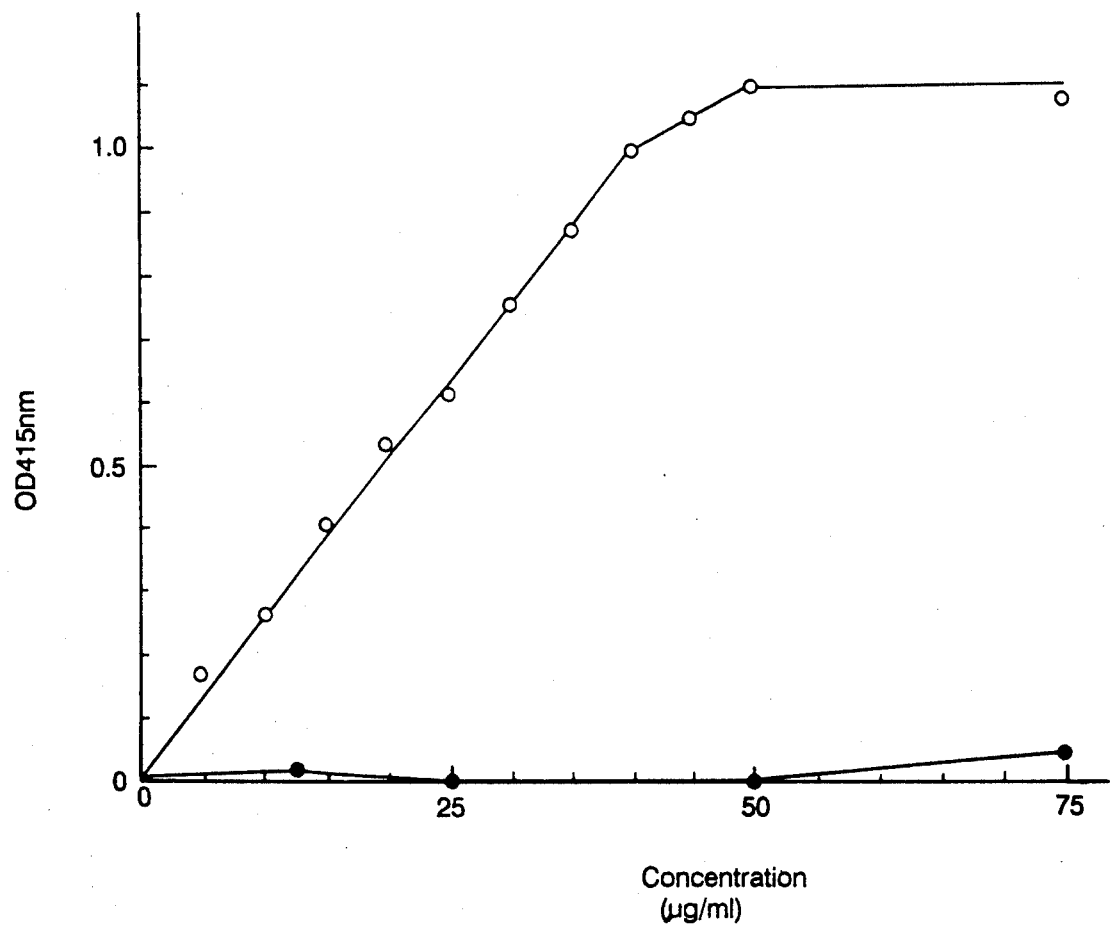
FIG. 18 shows the relationship between the last content of ND28 and absorbance at 415 nm, in which open circles represent the data for ND28 and closed circles represent the data for natural G-CSF.

It was demonstrated that, as shown in FIG. 18, ND28 can be quantitatively analyzed in the concentration range of 5 to 50 µg/ml. No reaction took place at all when natural G-CSF was used in place of ND28 in this reaction system.

EXAMPLE 26

To 3 ml of 0.1 M borate buffer (pH 10) containing 186 82 g/ml of hG-CSF with the amino acid sequence shown in Table 3 was added 56 mg of the chloro-compound prepared in Reference Example 5 which appears hereinafter and the reaction was carried out at 4° C. for 24 hours with stirring.

The unreacted chloro-compound was removed by ultrafiltration (cutoff molecular weight 30,000) and, then, using YMC-Pack AM-312ODS (Kurita Industries, Ltd.), reversed phase HPLC on a linear gradient of 0 to 70% acetonitrile was carried out. The chemically modified hG-CSF polypeptide was eluted in the fraction of about 50% acetonitrile (yield 30 µg, percent yield 5%). It was confirmed by SDS-polyacrylamide gel electrophoresis that this chemically modified hG-CSF polypeptide had one chloro-compound residue per molecule. The purity was in excess of 90%.

EXAMPLE 27

To 50 ml of 50 mM phosphate buffer (pH 7.2) containing 570 µg/ml of the same hG-CSF as used in Example 26 was added 240 mg of the active ester prepared in Reference Example 6 which appears hereinafter and the reaction was carried out at 4° C. for 6 hours.

After addition of 50 ml of 10 mM Tris-HCl buffer-0.7 M ammonium sulfate (pH 8.0), the reaction mixture was passed through a column (2.2 cm×26 cm) of butyl-Toyopearl 650 M (Tosoh) equilibrated with 10 mM Tris-HCl-0.35 M ammonium sulfate (pH 8.0) at a flow rate of 100 ml/hr. Then, the column was washed by passing 100 ml of 10 mM Tris-HCl-0.35 M ammonium sulfate (pH 8.0) at a flow rate of 100 ml/hr and, then, elution was carried out on a linear gradient with 200 ml of 10 mM Tris-HCl-0.35 M ammonium sulfate (pH 8.0) to 200 ml of 10 mM Tris-HCl buffer (pH 8.0) at a flow rate of 100 ml/hr. The object compound was eluted in fractions corresponding to 50 mM through 130 mM of ammonium sulfate. These fractions were collected (130 ml), subjected to ultrafiltration [cutoff molecular weight 10,000; membrane YM10 (Amicon)], and concentrated to 7 ml. The concentrate obtained was passed through a column (2.8 cm×70 cm) of Sephacryl S-200 (Pharmacia) equilibrated with 10 mM phosphate buffer-physiological saline (pH 7.2) (PBS) at a flow rate of 120 ml/hr, followed by passage of PBS at the same flow rate. The chemically modified hG-CSF polypeptide was eluted in fractions corresponding to 190 ml through 210 ml of PBS (yield 4.5 mg, percent yield 16%). It was verified by SDS-polyacrylamide gel electrophoresis that, in the resulting polypeptide, one molecule of the polyethylene glycol derivative carboxylic acid had been bound to each molecule of hG-CSF. The purity of the polypeptide was not less than 90%.

EXAMPLE 28

To 10 ml of 0.1 M borate buffer (pH 9) containing ND28 (570 µg/ml) obtained in Example 8 was added 54 mg of the active ester obtained in Reference Example 6 which also appears hereinafter and the reaction was conducted at 4° C. for 10 hours.

The unreacted active ester and its decomposition product were removed with an ultrafiltration membrane YM30 (Amicon) and, then, the internal fluid was substituted with 10 mM Tris-HCl buffer (pH 8) using the same membrane. The residual fluid was passed through a column (1.7 cm×4.4 cm) of DEAE-Toyopearl 650 M (Tosoh) equilibrated with 10 mM Tris-HCl buffer (pH 8.0) at a flow rate of 10 ml/hr. Then, the column was washed by passing 20 ml of 10 mM Tris-HCl buffer (pH 8) at a flow rate of 5 ml/hr and, then, elution was carried out on a linear gradient with 50 ml of 10 mM Tris-HCl buffer (pH 8) to 10 mM Tris-HCl-0.4 M NaCl (pH 8) at a flow rate of 5 ml/hr. The chemically modified hG-CSF polypeptide was eluted in fractions corresponding to 100 through 120 mM of NaCl (yield 0.85 mg; percent yield 15%). It was verified by SDS-polyacrylamide gel electrophoresis that, in the resulting polypeptide, one molecule of the polyethylene glycol derivative carboxylic acid had been bound to one molecule of the hG-CSF derivative. The purity of this polypeptide was not less than 90%.

REFERENCE EXAMPLE 5

Production of 2,4-bis(O-methoxypolyethylene glycol)-6-chloro-s-triazine

In 100 ml of dry toluene containing 10 g of anhydrous sodium carbonate was dissolved 20 g of monomethoxypolyethylene glycol having an average molecular weight of 4000 (Nippon Oil and Fats) and the solution was heated at 110° C. for 30 minutes. Then, 500 mg of cyanuric chloride was added and the mixture was heated at 110° C. for 24 hours. The reaction residue was filtered off, followed by addition of 300 ml of petroleum ether to cause precipitation. The precipitate was washed with several portions of petroleum ether to recover 10 g of 2,4-bis(O-methoxypolyethylene glycol)-6-chloro-s-triazine (yield 50%).

REFERENCE EXAMPLE 6

Synthesis of monomethoxypolyethylene glycol succinyl-N-hydroxysuccinimide ester

To 50 ml of dry toluene were added 20 g of thoroughly dehydrated monomethoxypolyethylene glycol having an average molecular weight of 5000 (Union Carbide) and 2 g of succinic anhydride and the mixture was refluxed at 150° C. for 5 hours. The toluene was distilled off under reduced pressure and the residue was thoroughly solubilized by addition of 30 ml of methylene chloride. To this was added 400 ml of dry ethyl ether to cause precipitation. The precipitate was recrystallized from methylene chloride-ethyl ether (volume ratio: 1:3) to recover 10 g (yield about 50%) of succinylated monomethoxypolyethylene glycol. A portion of this succinylated product (3.3 g) and 100 mg of N-hydroxysuccinimide were solubilized in 5 ml of dry methylene chloride, followed by addition of 200 mg of dicyclohexylcarbodiimide (DCC) with ice-cooling. The mixture was then stirred at room temperature for 20 hours. The byproduct dicyclohexylurea (DCU) was filtered off and ethyl ether was added to the filtrate to cause precipitation. The resulting precipitate was recrystallized from methylene chloride-ethyl ether (volume ratio: 1.3) to recover 2.5 g (yield 72%) of monomethoxypolyethylene glycol succinyl-N-hydroxysuccinimide ester.

TEST EXAMPLE 4

Specific activity and mouse leukemia cell NFS60 growth promoting activity of the chemically modified hG-CSF derivative In the same manner as Example 28, the hG-CSF derivative was reacted with the active ester and the unreacted active ester and its decomposition product were removed using an ultrafiltration membrane. Then, using the same membrane as above, the internal fluid was substituted with PBS and the G-CSF activity and NFS60 cell growth promoting activity [Proceedings of the National Academy of Sciences of the USA 82, 6687 (1985)] of the chemically modified hG-CSF derivative in the residual fluid were assayed. The results are shown in Table 9.

TABLE 9

| Sample | Specific activity (unit/mg protein) | NFS60 growth promoting activity |
|---|---|---|
| hG-CSF derivative | 100% | 100% |
| Chemically modified hG-CSF derivative | 12.9% | 6.9% |

It is evident from the above results that the chemically modified hG-CSF derivative retained CSF activity against mouse bone marrow stem cells. It is also clear that the same derivative had a growth promoting effect on NFS60 cells which are known to show G-CSF-dependent growth.

TEST EXAMPLE 5

Leukocyte (granulocyte) increasing effect

The same chemically modified hG-CSF derivative as used in Test Example 4 was subcutaneously administered to C3H/He mice (male, n=3) either once or once a day for 6 consecutive days. The blood was sampled at timed intervals and the white blood cells (WBC) in peripheral blood were counted. The results are shown in Table 10 (single administration) and Table 11 (repeated administration).

TABLE 10

| | The time course of WBC after single administration (s.c.) | | | | | | | |
|---|---|---|---|---|---|---|---|---|
| | Dosage[a] | WBC (% of normal control) Blood sampling interval (hr) | | | | | | |
| Sample | (μg/mouse) | 1 | 5 | 8 | 16 | 24 | 48 | 72 |
| hG-CSF derivative | 10 | 75.4 | 159.1 | 228.3 | 166.7 | 200.1 | 125.5 | 110.0 |
| Chemically modified hG-CSF derivative | 10 | 81.1 | 179.2 | 259.9 | 169.8 | 186.7 | 177.4** | 96.5 |

Notes
[a]The same weight as hG-CSF protein was administered.
**$P < 0.01$ (Student's t-test)

TABLE 11

The time course of WBC in 6-day repeated administration (s.c.)

| Sample | Dosage[a] (μg/mouse/day) | WBC (% of normal control) Blood sampling interval (Day) | | | | | |
|---|---|---|---|---|---|---|---|
| | | 1 | 2 | 3 | 4 | 5 | 6 |
| hG-CSF derivative | 1 | 79.3 | 95.5 | 85.1 | 91.2 | 79.1 | 116.8 |
| Chemically modified hG-CSF derivative | 1 | 131.1** | 185.4*** | 148.7*** | 125.9* | 124.4* | 143.4 |
| hG-CSF derivative | 10 | 163.0 | 221.5 | 220.3 | 289.3 | 273.0 | 284.0 |
| Chemically modified hG-CSF derivative | 10 | 120.9 | 181.3 | 171.5 | 273.1 | 355.4 | 442.3 |

Notes
[a]The same weight as hG-CSF protein was administered.
*$P < 0.05$, $P < 0.01$, *$P < 0.001$ (Student's t-test)

In single administration, increase in WBC peaking at 8 hours after administration was observed but whereas the counted declined thereafter to normal in 48 hours after administration in the case of the hG-CSF derivative, a significant increase in WBC was still observed even after 48 hours in the case of the chemically modified hG-CSF derivative.

In repeated administration, particularly in the low dose group, the chemically modified hG-CSF derivative showed a significant leukocyte increasing effect as compared with the hG-CSF derivative.

TEST EXAMPLE 6

Time course of plasma concentration

The same chemically modified hG-CSF derivative as used in Test Example 4 was subcutaneously administered to C3H/He mice (male, n=3) either once or once a day for 6 consecutive days. The blood was sampled at timed intervals and the plasma concentration of G-CSF was determined. The results are set forth in Table 12 (single administration) and Table 13 (repeated administration). In some experiments, a single dose of the same chemically modified hG-CSF derivative was intravenously administered (Table 14).

TABLE 12

| Sample | Dosage[a] (μg/mouse) | Single adiminstration (s.c.) Plasma concentration (Units/ml[b] plasma, ×10⁴) Blood sampling interval | | | | | | |
|---|---|---|---|---|---|---|---|---|
| | | 15 min | 30 min | 1 hr | 5 hr | 7.5 hr | 15 hr | 24 hr |
| hG-CSF derivative | 10 | 248.3 | 772.7 | 2744.5 | 214.0 | 163.3 | 49.7 | 6.2 |
| Chemically modified hG-CSF derivative | 10 | 29.8 | 44.6 | 208.3 | 1709.0 | 1146.7 | 89.6 | 21.6 |

Notes
[a]The same weight as hG-CSF protein was administered.
[b]Calculated from NFS 60 cell growth promoting activity (Half max = 50 U).

TABLE 13

| Sample | Dosage[a] (μg/mouse/day) | Repeated administration (s.c.) Plasma concentration[b] (Units/ml[c] plasma, ×10⁴) Blood sampling interval (Day) | | | | | |
|---|---|---|---|---|---|---|---|
| | | 0 | 1 | 2 | 3 | 4 | 5 |
| hG-CSF derivative | 10 | NT.[d] 4.8 | 1354.9 2.2 | 692.7 NT. | 915.3 —[e] | 768.8 — | 756.4 — |
| Chemically modified hG-CSF derivative | 10 | NT. 14.2 | 92.2 11.3 | 376.9 NT. | 235.9 4.7 | 53.7 2.2 | 53.9 2.2 |

Notes
[a]The same weight as G-CSF protein was administered.
[b]Upper row: plasma concentration at 1 hr after administration
Lower row: plasma concentration at 24 hr after administration
[c]calculated from NFS 60 cell growth promoting activity (Half max = 50 U)
[d]NT. (not tested)
[e]— below detection limit

TABLE 14

| Sample | Dosage[a] (μg/mouse) | Single administration (i.v.) Plasma concentration (Units/ml[b] plasma, ×10⁴) Blood sampling interval | | | | | |
|---|---|---|---|---|---|---|---|
| | | 3 min | 10 min | 30 min | 1 hr | 2 hr | 5 hr |
| hG-CSF derivative | 10 | 1307 | 1356 | 901 | 631.3 | 563 | 355.8 |
| Chemically modified hG-CSF derivative | 10 | 6883 | 6181 | 4320 | 3332 | 1621 | 905.6 |

Notes
[a]The same weight as G-CSF protein was administered.
[b]calculated from NFS 60 cell growth promoting activity (Half max = 50 U).

In the case of single subcutaneous administration, whereas the plasma concentration of the hG-CSF derivative reached a peak at 1 hour and declined rapidly thereafter, that of the chemically modified hG-CSF derivative showed a gradual increase in 5 to 7 hours after administration and maintained a comparatively high level even after 24 hours (Table 12). On the other hand, in repeated subcutaneous administration, the hG-CSF derivative showed a higher plasma concentration at 1 hour after administration but a lower level at 24 hours and was no longer detected on day 3. In contrast, the chemically modified hG-CSF derivative was detectable even at 24 hours and its concentration was higher than that of the hG-CSF derivative.

In intravenous administration, the chemically modified hG-CSF administration, the chemically modified hG-CSF derivative gave significantly higher plasma concentrations as shown in Table 14.

Thus, the chemically modified hG-CSF and chemically modified hG-CSF derivatives of this invention produce an enhanced peripheral leukocyte (granulocyte) increasing effect with improved stability and residence time in the blood and, as such, can be used advantageously in clinical medicines.

BEST MODE FOR CARRYING OUT THE INVENTION

While the invention has been described with respect to what is presently regarded as the most practical embodiments thereof, it will be understood by those of ordinary skill in the art that various alterations and modifications may be made which nevertheless remain within the scope of the invention as defined by the claims which follow.

What is claimed is:

1. A monoclonal antibody of the $IgG_1$ isotype which specifically binds to a derivative of human granulocyte colony stimulating factor having the amino acid sequence as shown in Table 3, but does not bind to a natural human granulocyte colony stimulating factor, said monoclonal antibody being secreted by hybridoma cell line FERM Deposit No. BP-1665.

* * * * *